US012747466B2

(12) United States Patent
Lo et al.

(10) Patent No.: US 12,747,466 B2
(45) Date of Patent: Sep. 29, 2026

(54) ANALYSIS OF NUCLEIC ACIDS ASSOCIATED WITH EXTRACELLULAR VESICLES IN PREGNANT FEMALES

(71) Applicant: Centre for Novostics, Shatin (HK)

(72) Inventors: Yuk-Ming Dennis Lo, Homantin (CN); Rossa Wai Kwun Chiu, Shatin (CN); Kwan Chee Chan, Jordan (CN); Peiyong Jiang, Pak Shek Kok (CN); Qing Zhou, Tai Po (CN)

(73) Assignee: Centre for Novostics, Shatin (HK)

( * ) Notice: Subject to any disclaimer, the term of this patent is extended or adjusted under 35 U.S.C. 154(b) by 649 days.

(21) Appl. No.: 18/195,207

(22) Filed: May 9, 2023

(65) Prior Publication Data

US 2023/0366007 A1 Nov. 16, 2023

Related U.S. Application Data

(60) Provisional application No. 63/340,316, filed on May 10, 2022.

(51) Int. Cl.

| | |
|---|---|
| ***C12Q 1/68*** | (2018.01) |
| ***C12Q 1/6806*** | (2018.01) |
| ***C12Q 1/686*** | (2018.01) |
| ***C12Q 1/6869*** | (2018.01) |
| ***C12Q 1/6883*** | (2018.01) |
| ***G16B 30/10*** | (2019.01) |

(52) U.S. Cl.

CPC ........... *C12Q 1/6806* (2013.01); *C12Q 1/686* (2013.01); *C12Q 1/6869* (2013.01); *C12Q 1/6883* (2013.01); *G16B 30/10* (2019.02)

(58) Field of Classification Search

CPC .................................................... C12Q 1/6869

See application file for complete search history.

(56) References Cited

U.S. PATENT DOCUMENTS

| | | | | |
|---|---|---|---|---|
| 8,620,593 | B2 | 12/2013 | Lo et al. | |
| 8,706,422 | B2 | 4/2014 | Lo et al. | |
| 9,892,230 | B2 | 2/2018 | Lo et al. | |
| 10,319,463 | B2 | 6/2019 | Lo et al. | |
| 10,643,738 | B2 | 5/2020 | Lo et al. | |
| 11,168,356 | B2 | 11/2021 | Lo et al. | |
| 11,242,520 | B2 | 2/2022 | Gao et al. | |
| 12,054,776 | B2 | 8/2024 | Lo et al. | |
| 2013/0230858 | A1 | 9/2013 | Cantor et al. | |
| 2018/0119210 | A1 | 5/2018 | Zeevi et al. | |
| 2020/0208213 | A1 | 7/2020 | Skog et al. | |
| 2021/0254136 | A1* | 8/2021 | Edelman | C12Q 1/6869 |
| 2021/0254142 | A1 | 8/2021 | Lo et al. | |
| 2021/0265007 | A1 | 8/2021 | Lo et al. | |
| 2024/0339220 | A1* | 10/2024 | Mcelrath | G16H 50/30 |

FOREIGN PATENT DOCUMENTS

| | | | |
|---|---|---|---|
| CN | 110191951 | A | 8/2019 |
| CN | 112391382 | A | 2/2021 |
| CN | 113151398 | A | 7/2021 |
| WO | 2021055338 | A1 | 3/2021 |

OTHER PUBLICATIONS

International Search Report and Written Opinion of the International Searching Authority mailed Aug. 18, 2023 in International Patent Application No. PCT/CN2023/092866. 9 pages.
Hromadnikova, I. et al.; "Quantification of Fetal and Total Circulatory DNA in Maternal Plasma Samples Before and After Size Fractionation by Agarose Gel Electrophoresis"; DNA and Cell Biology; 2006; vol. 25, No. 11; pp. 635-640 (7 total pages).
Zhang, Weiting et al.; "Detection of fetal trisomy and single gene disease by massively parallel sequencing of extracellular vesicle DNA in maternal plasma: a proof-of-concept validation"; BMC Medical Genomics; 2019; vol. 12, No. 151; pp. 1-11.
Extended European Search Report dated May 15, 2026 in EP Patent Application No. 23802871.6. 11 pages.
Campos, Camila D.M. et al.; "Analytical Technologies for Liquid Biopsy of Subcellular Materials"; Annual Reviews: Annual Review of Analytical Chemistry; 2021; vol. 14, No. 1; pp. 207-229.
Garcia-Romero, N. et al.; "Polyethylene glycol improves current methods for circulating extracellular vesicle-derived DNA isolation"; Journal of Translational Medicine; 2019; vol. 17, No. 75; pp. 1-11.
Snyder, Matthew W. et al.; "Noninvasive fetal genome sequencing: a primer"; Prenatal Diagnosis; 2013; vol. 33, No. 6; pp. 547-554.

* cited by examiner

*Primary Examiner* — Kenneth R Horlick

(74) *Attorney, Agent, or Firm* — Kilpatrick Townsend & Stockton LLP

(57) ABSTRACT

Cell-free nucleic acid from extracellular particles (EPs) is analyzed. A sample can be purified for the extracellular particles. As examples, the purification can include centrifuging, washing, and a nuclease treatment. To increase the fetal fraction, the purification can enrich a sample for a certain type of EPs (e.g., long EPs). In this manner, a desired population of particles can be selected for the analysis of their nucleic acids. As part of an analysis of the nucleic acid molecules (fragments) from an enriched sample, nucleic acid molecules greater than a certain size can be selected, which can increase genetic and/or epigenetic informativeness, without an adverse effect (e.g., the reduction of fetal DNA fraction). The long nucleic acid fragments can be analyzed in various ways, including using short read sequencing techniques that perform fragmentation before sequencing and using long read sequencing techniques.

33 Claims, 24 Drawing Sheets

FIG. 12A
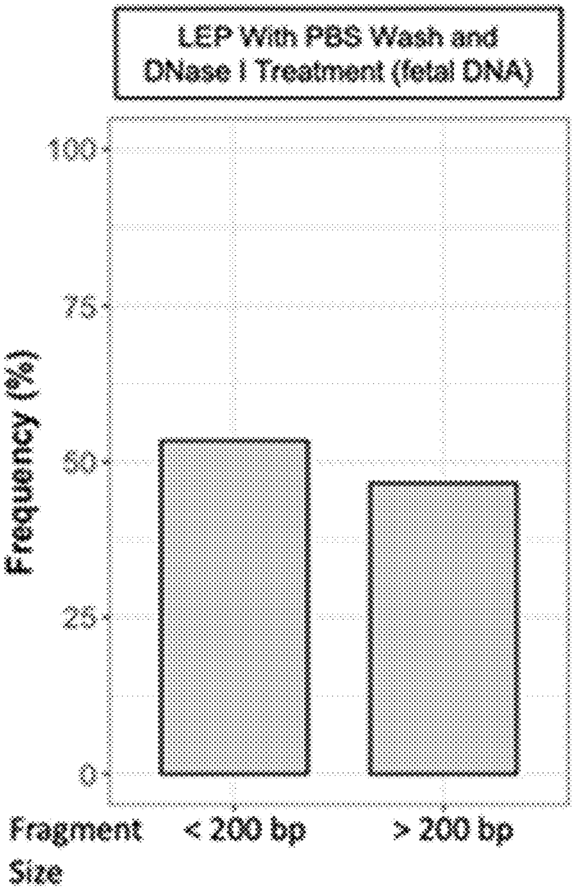
FIG. 12B
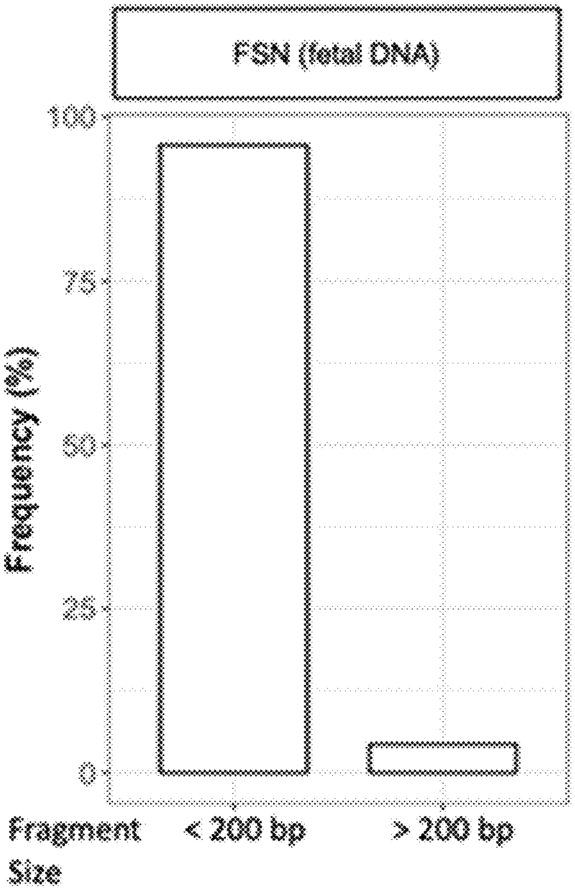
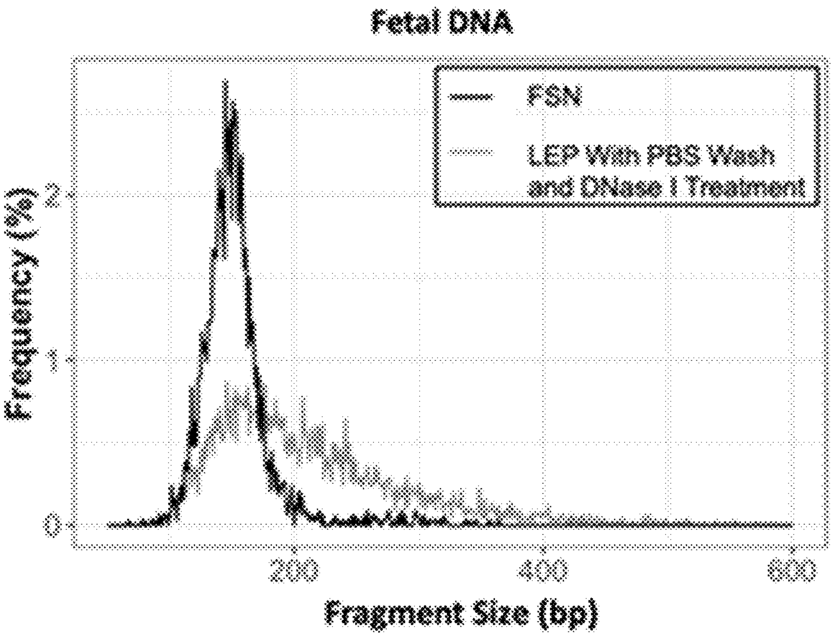
FIG. 12C

ANALYSIS OF NUCLEIC ACIDS ASSOCIATED WITH EXTRACELLULAR VESICLES IN PREGNANT FEMALES

CROSS-REFERENCES TO RELATED APPLICATIONS

The present application claims priority to U.S. Provisional Application No. 63/340,316, entitled "Analysis Of Nucleic Acids Associated With Extracellular Vesicles," filed on May 10, 2022, the entire contents of which are herein incorporated by reference for all purposes.

BACKGROUND

The revealing of circulating cell-free fetal DNA in maternal plasma has opened up a series of new avenues for non-invasive prenatal testing (NIPT), including chromosomal aneuploidy detection and diagnosis of monogenic diseases. The accuracy of NIPT is affected by the fractional concentration of fetal DNA in a maternal plasma sample, which is usually referred to as the fetal DNA fraction (Chiu et al. BMJ 2011; 342: c7401; Canick et al. Prenat. Diagn. 2013; 33: 667-674). Enhancements of the performance of NIPT are required when analyzing samples with a relatively low fetal DNA fraction for the following reasons.

For example, a higher chance of occurrence of test failures or no-call results when the fetal DNA fraction is low (Porreco et al. Am. J. Obstet. Gynecol. 2014; 211: 365. e1-365. e12). Secondly, low sensitivity of detecting fetal aneuploidies in low fetal DNA fraction pregnant subjects (Chiu et al. BMJ 2011; 342: c7401; Jiang et al. Bioinformatics 2012; 28: 2883-2890, npj Genomic Med. 2016; 1: 16013; Hui et al. Prenatal Diagnosis 2020; 40:155-163), which leads to a high false-negative rate. Simply repeating the assay still has a high chance of false calling or no calling. Previously, Canick et al. reported four false negatives among 212 cases with Down syndrome, all of which had a relatively low fetal DNA fraction of 4%-7% (Canick et al. Prenat. Diagn 2013; 33: 667-674). Lastly, the prevalence of fetal aneuploidies seems to vary in pregnancies with different fetal DNA fractions. For example, it was demonstrated that in patients with a fetal DNA fraction below 4%, the prevalence of aneuploidy was 4.7%, which was significantly higher compared with the prevalence of 0.4% in the overall cohort (Norton et al. N. Engl. J. Med. 2015; 372: 1589-1597). Thus, patients with low fetal DNA fraction cannot be ignored.

Therefore, it is desirable to provide improved techniques that address such problems.

BRIEF SUMMARY

In various examples, cell-free DNA from extracellular particles (EPs) is analyzed. A sample can be purified for the extracellular particles. As examples, the purification can include centrifuging, washing, and a nuclease treatment. To increase the fetal fraction, the purification can enrich a sample for a certain type of EPs (e.g., long EPs). In this manner, a desired population of particles can be selected for the analysis of their nucleic acids. As part of an analysis of the DNA molecules (fragments) from an enriched sample, DNA molecules greater than a certain size can be selected, which can increase genetic and/or epigenetic informativeness, without an adverse effect (e.g., the reduction of fetal DNA fraction). The long DNA fragments can be analyzed in various ways, including using short read sequencing techniques that perform fragmentation before sequencing and using long read sequencing techniques.

In one example, a method includes receiving a blood sample of a female having a pregnancy with a fetus. One or more purification steps can enrich for extracellular particles to produce an enriched sample. An extracellular particle can include cell-free nucleic acids (e.g., DNA and/or RNA) inside of a membrane. Membranes of the extracellular particles can be disrupted to expose cell-free nucleic acid molecules from the extracellular particles. An assay can be applied to cell-free nucleic acid molecules to obtain sequence reads. Cell-free nucleic acid molecules from inside an EP and/or bound to a surface of the EP may be assayed. Sizes of the cell-free nucleic acid molecules can be determined. As examples, the sequence reads can be used to determine sizes of the cell-free nucleic acid molecules, or physical techniques can be used, such as electrophoresis or PCR with different-sized amplicons. A set of cell-free nucleic acid molecules that are greater than a size threshold can be identified, e.g., where the size threshold being 200 bp or more. The sequence reads can be analyzed to determine a genomic characteristic of the fetus.

In another example, a blood sample of a female having a pregnancy with a fetus can include extracellular particles and particle-free nucleic acids. The extracellular particles can include cell-free nucleic acids inside of membranes. A physical separation technique can preferentially select at least a portion of the extracellular particles, thereby obtaining a particle-enriched sample, which can be treated using a treatment technique that removes excess particle-free nucleic acids, thereby obtaining a treated particle-enriched sample. The treatment technique can include washing the particle-enriched sample with an ionic solution and applying a nuclease to the particle-enriched sample. The treatment technique can increase a fractional concentration of fetal nucleic acids in the treated particle-enriched sample relative to the particle-enriched sample. Membranes of the extracellular particles can be disrupted to expose cell-free nucleic acids from the extracellular particles. An assay can be applied to cell-free nucleic acids to obtain sequence reads. Cell-free nucleic acid molecules from inside an EP and/or bound to a surface of the EP may be assayed. The sequence reads can be analyzed to determine a genomic characteristic of the fetus or of the pregnancy of the female.

In another example, a blood sample of a female having a pregnancy with a fetus can include extracellular particles and particle-free nucleic acids molecules. The extracellular particles can include cell-free nucleic acid molecules inside of membranes. One or more purification steps can enrich for extracellular particles to produce an enriched sample. Membranes of the extracellular particles can be disrupted to expose cell-free nucleic acid molecules from the extracellular particles. A sequencing technique can be applied the cell-free nucleic acid molecules to obtain sequence reads. Cell-free nucleic acid molecules from inside an EP and/or bound to a surface of the EP may be sequenced. At least a portion of the sequence reads can be more than 600 bp. The sequence reads can be analyzed to determine a genomic characteristic of the fetus or of the pregnancy of the female.

In another example, a blood sample of a female having a pregnancy with a fetus can include extracellular particles and particle-free nucleic acid molecules. The extracellular particles can include cell-free nucleic acid molecules inside of membranes. One or more purification steps can enrich for extracellular particles to produce an enriched sample. Membranes of the extracellular particles can be disrupted to expose cell-free nucleic acid molecules from the extracellular particles. At least a portion of the cell-free nucleic acid molecules from the extracellular particles are at least 600 bp. A fragmentation technique can be applied to the cell-free nucleic acid molecules. After applying the fragmentation technique, a sequencing technique can be applied to the cell-free nucleic acid molecules to obtain sequence reads. Cell-free nucleic acid molecules from inside an EP and/or bound to a surface of the EP may be sequenced. The sequence reads can be analyzed to determine a genomic characteristic of the fetus or of the pregnancy of the female.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

FIGS. 12A-12C show enrichment of long fetal DNA in LEP-associated DNA.

TERMS

Figure 1:
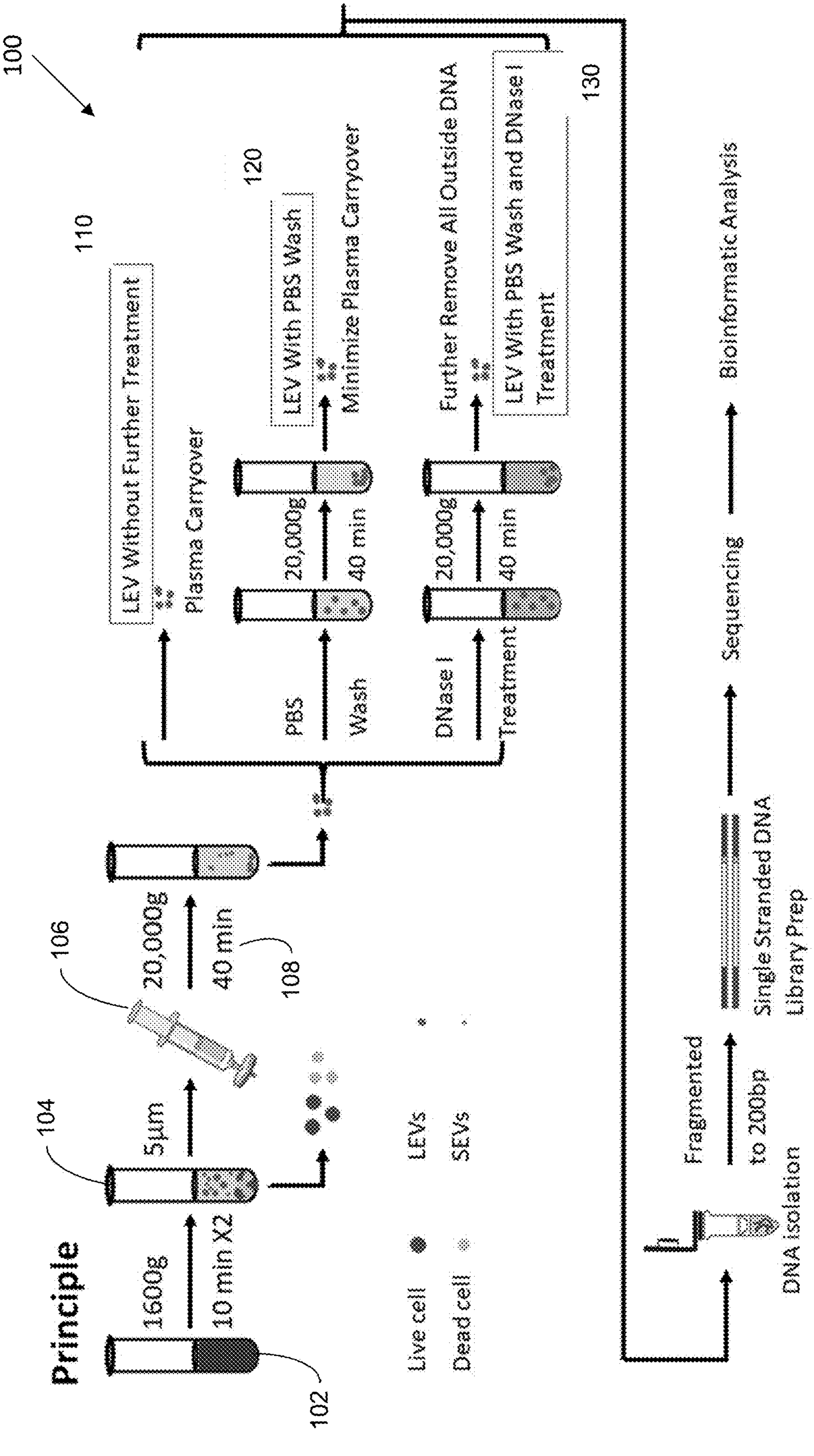
FIG. 1 shows a first example workflow of EP separation and analysis.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus). "Reference tissues" can correspond to tissues used to determine tissue-specific methylation patterns. Multiple samples of a same tissue type from different individuals may be used to determine a tissue-specific methylation patterns for that tissue type (e.g., fetal tissue).

A "biological sample" refers to any sample that is taken from a pregnant woman and contains one or more nucleic acid molecule(s) (e.g., DNA and/or RNA) of interest. The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), intraocular fluids (e.g., the aqueous humor), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. Other centrifuging protocols may be used, e.g., at various force (rotational speed) such as at least 1,600 g, 5,000 g, 10,000 g, 16,000 g, 20,000 g, 30,000 g, 40,000 g 50,000 g, 60,000 g, 70,000 g, 80,000 g, 90,000 g, 100,000 g, and 110,000 g, and for various times, e.g., at least 5 minutes, 10 minutes, 15 minutes, 20 minutes, 30 minutes, 40 minutes, one hour, or two hours which can be repeated. Other centrifugation protocols are described herein. As part of an analysis of a biological sample, a statistically significant number of cell-free DNA molecules can be analyzed (e.g., to provide an accurate measurement) for a biological sample. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed. At least a same number of sequence reads can be analyzed.

An "extracellular vesicle" (EV), also referred to as an "extracellular particle" (EP), refer to a small, localized particle with particular physical and/or chemical properties such as volume, density, mass, electronegativity, and permeability, which could be released from a cell and which may occur from a live cell or during cell death, such as apoptosis or necrosis. An EP may have a membrane within which genomic material resides, or may not have a membrane (e.g., a protein-nucleic-acid complex that is not membrane-bound). Such particles can include proteins, nucleic acids (DNA and/or RNA), lipids, metabolites, and organelles from the parent cell. EVs can be divided according to size and synthesis route, and may be referred to as exosomes, microvesicles and apoptotic bodies. In some context, exosomes are membrane-bound EVs that are produced in the endosomal compartment of most eukaryotic cells. Microvesicles (also called ectosomes or microparticles) are a type of extracellular vesicle (EV) that are released from the cell membrane. EVs can be referred to as small (SEV) or large (LEV) depending on size. As examples, EVs can have diameters from a few nanometres to a few micrometres. EVs can play a role in intercellular communication and can transport molecules such as mRNA, miRNA, and proteins between cells. Any of the above terms are exchangeable and refer to EVs or EPs. Example numbers of particles that can be analyzed include at least 100, 500, 1,000, 5,000, 10,000, 50,000, and 100,000 particles.

The term "fragment" (e.g., a DNA or an RNA fragment), as used herein, can refer to a portion of a polynucleotide or polypeptide sequence that comprises at least 3 consecutive nucleotides. A nucleic acid fragment can retain the biological activity and/or some characteristics of the parent polynucleotide. A nucleic acid fragment can be double-stranded or single-stranded, methylated or unmethylated, intact or nicked, complexed or not complexed with other macromolecules, e.g., lipid particles or proteins. A nucleic acid fragment can be a linear fragment or a circular fragment.

"Cell-free DNA" (cfDNA) can include DNA from an extracellular particle and DNA that is not from an extracellular particle. "Extracellular particle DNA," "EP DNA," and "EV DNA" (such terms may also use cfDNA instead of DNA) refer to cell-free DNA that is from extracellular particles. Such EP DNA can include DNA within a membrane of the particle as well as DNA bound to the surface of the EP. EP-associated DNA can also refer to such EP DNA from inside an EP and/or bound to the surface of EP. "Particle free DNA," "EP free DNA," and "EV-free DNA" refer to cell-free DNA that is not from extracellular particles. Such terms can also be used for RNA or nucleic acids more generally.

"Clinically-relevant DNA" can refer to DNA of a particular tissue source that is to be measured, e.g., to determine a fractional concentration of such DNA or to classify a phenotype of a sample (e.g., plasma). Examples of clinically-relevant DNA are fetal DNA in maternal plasma.

The term "assay" generally refers to a technique for determining a property of a nucleic acid or a sample of nucleic acids (e.g., a statistically significant number of nucleic acids), as well as a property of the subject from which the sample was obtained. An assay (e.g., a first assay or a second assay) generally refers to a technique for determining the quantity of nucleic acids in a sample, genomic identity of nucleic acids in a sample, the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art may be used to detect any of the properties of nucleic acids mentioned herein. Properties of nucleic acids include a sequence, quantity, genomic identity, copy number, a methylation state at one or more nucleotide positions, a size of the nucleic acid, a mutation in the nucleic acid at one or more nucleotide positions, and the pattern of fragmentation of a nucleic acid (e.g., the nucleotide position(s) at which a nucleic acid fragments). The term "assay" may be used interchangeably with the term "method". An assay or method can have a particular sensitivity and/or specificity (e.g., based on selection of one or more cutoff values), and their relative usefulness as a diagnostic tool can be measured using Receiver Operating Characteristic (ROC) Area-Under-the-Curve (AUC) statistics.

A "sequence read" refers to a string of nucleotides obtained from any part or all of a nucleic acid molecule. For example, a sequence read may be a short string of nucleotides (e.g., 20-150 nucleotides) sequenced from a nucleic acid fragment, a short string of nucleotides at one or both ends of a nucleic acid fragment, or the sequencing of the entire nucleic acid fragment that exists in the biological sample. A sequence read may be a long string of nucleotides (e.g., several hundreds or thousands of nucleotides) sequenced from a nucleic acid fragment. A sequence read may be obtained in a variety of ways, e.g., using sequencing techniques or using probes, e.g., in hybridization arrays or capture probes as may be used in microarrays, or amplification techniques, such as the polymerase chain reaction (PCR) or linear amplification using a single primer or isothermal amplification. Example sequencing techniques include massively parallel sequencing, targeted sequencing, Sanger sequencing, sequencing by ligation, ion semiconductor sequencing, and single molecule sequencing (e.g., using a nanopore, or single-molecule real-time sequencing (e.g., from Pacific Biosciences)). Such sequencing can be random sequencing or targeted sequencing (e.g., by using capture probes hybridizing to specific regions or by amplifying certain region, both of which enrich such regions). Example PCR techniques include real-time PCR and digital PCR (e.g., droplet digital PCR). As part of an analysis of a biological sample, a statistically significant number of sequence reads can be analyzed, e.g., at least 1,000 sequence reads can be analyzed. As other examples, at least 5,000, 10,000 or 50,000 or 100,000 or 500,000 or 1,000,000 or 5,000,000 sequence reads, or more, can be analyzed.

"Single-molecule sequencing" refers to sequencing of a single template DNA molecule to obtain a sequence read without the need to interpret base sequence information from clonal copies of a template DNA molecule. The single-molecule sequencing may sequence the entire molecule or only part of the DNA molecule. A majority of the DNA molecule may be sequenced, e.g., greater than 50%, 55%, 60%, 65%, 70%, 75%, 80%, 85%, 90%, 95%, or 99%. A sequence read (or reads from both ends) can be aligned to a reference genome. When both ends are aligned (e.g., as part of a read of the entire fragment or for paired-ends), greater accuracy can be achieved in the alignment and a length of the fragment can be obtained.

The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically include multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations. The term "haplotype" can refer to a combination of alleles or epigenetic markers (e.g., methylation) at multiple loci that are transmitted together on the same chromosome or chromosomal region. A haplotype may refer to as few as one pair of loci or to a chromosomal region, or to an entire chromosome or chromosome arm.

As used herein, the term "locus" or its plural form "loci" is a location or address of any length of nucleotides (or base pairs). A locus may have a variation across genomes.

The term "fractional fetal DNA concentration" is used interchangeably with the terms "fetal DNA proportion" and "fetal DNA fraction," and refers to the proportion of fetal DNA molecules that are present in a biological sample (e.g., maternal plasma or serum sample) that is derived from the fetus (Lo et al, *Am J Hum Genet.* 1998; 62:768-775; Lun et al, *Clin Chem.* 2008; 54:1664-1672).

The terms "size profile" and "size distribution" generally relate to the sizes of DNA fragments in a biological sample. A size profile may be a histogram that provides a distribution of an amount of DNA fragments at a variety of sizes. Various statistical parameters (also referred to as size parameters or just parameter) can distinguish one size profile to another. One parameter is the percentage of DNA fragment of a particular size or range of sizes relative to all DNA fragments or relative to DNA fragments of another size or range.

A "calibration sample" can correspond to a biological sample whose fractional concentration of clinically-relevant DNA (e.g., fetal-specific DNA fraction) or other measurable value is known or determined via a calibration method, e.g., using an allele specific to the tissue, such as in pregnancy whereby an allele present in the fetal genome but absent in the maternal genome can be used as a marker for the fetus. As another example, a calibration sample can correspond to a sample from which a calibration value of another property is determined, where such other property can be used to estimate the fractional concentration (or other measurable value).

A "calibration data point" includes a "calibration value" and a measured or known fractional concentration of the clinically-relevant DNA (e.g., DNA of particular tissue type). The calibration value can be determined from relative frequencies (e.g., an aggregate value) as determined for a calibration sample, for which the fractional concentration of the clinically-relevant DNA is known. The calibration data points may be defined in a variety of ways, e.g., as discrete points or as a calibration function (also called a calibration curve or calibration surface). The calibration function could be derived from additional mathematical transformation of the calibration data points.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

A "separation value" corresponds to a difference or a ratio involving two values, e.g., two fractional contributions, two size values/parameters, two methylation levels, or two counts.

A separation value is an example of a parameter. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and a ratio. A separation value can be compared to a threshold to determine whether the separation between the two values is statistically significant.

"DNA methylation" in mammalian genomes typically refers to the addition of a methyl group to the 5' carbon of cytosine residues (i.e., 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as N6-methyladenine, has also been reported.

A "methylation level" is an example of a relative abundance, e.g., between methylated DNA molecules (e.g., at particular sites) and other DNA molecules (e.g., all other DNA molecules at particular sites or just unmethylated DNA molecules). The amount of other DNA molecules can act as a normalization factor. As another example, an intensity of methylated DNA molecules (e.g., fluorescent or electrical intensity) relative to intensity of all or unmethylated DNA molecules can be determined. The relative abundance can also include an intensity per volume. A methylation level can be determined using a methylation-aware assay such as methylation-aware sequencing or PCR. Example methylation-aware sequencing can include bisulfite sequencing or single molecule techniques, e.g., using nanopores or single-molecule real-time sequencing, as is described in U.S. Publication No. 2021/0047679-A1.

A "methylation pattern" refers to a series of methylation statuses at multiple sites of a fragment, a genome, or a sample (e.g., including a particular tissue type). The methylation status at a site can be unmethylated (U) or methylated (M). For a sample or a genome, the methylation status can be a proportion. A reference methylation pattern can be designated as methylated when the methylation level at a site is greater than a specified threshold (e.g., 70%, 75%, 80%, 85%, 90%, 95%, or 99%). A reference methylation pattern can be designated as unmethylated when the methylation level at a site is less than a specified threshold (e.g., 30%, 25%, 20%, 15%, 10%, 5%, or 1%). Thus, a methylation pattern of a fragment (series of M and U at sites) can be compared and matched to a reference methylation pattern of fetal tissue. Optionally, the reference methylation patterns of various tissues can be obtained from single-molecule sequencing, expressing as methylation patterns across individual molecules, wherein the methylation status can be a binary value (0 or 1, respectively represents unmethylated and methylated status).

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts. A cutoff or threshold may be "a reference value" or derived from a reference value that is representative of a particular classification or discriminates between two or more classifications. A cutoff may be predetermined with or without reference to the characteristics of the sample or the subject. For example, cutoffs may be chosen based on the age or sex of the tested subject. A cutoff may be chosen after and based on output of the test data. For example, certain cutoffs may be used when the sequencing of a sample reaches a certain depth. As another example, reference subjects with known classifications of one or more conditions and measured characteristic values (e.g., a methylation level, a statistical size value, or a count) can be used to determine reference levels to discriminate between the different conditions and/or classifications of a condition (e.g., whether the subject has the condition). A reference value can be selected as representative of one classification (e.g., a mean) or a value that is between two clusters of the metrics (e.g., chosen to obtain a desired sensitivity and specificity). As another example, a reference value can be determined based on statistical simulations of samples. Any of these terms can be used in any of these contexts. Such a reference value can be determined in various ways, as will be appreciated by the skilled person. For example, metrics can be determined for two different cohorts of subjects with different known classifications, and a reference value can be selected as representative of one classification (e.g., a mean) or a value that is between two clusters of the metrics (e.g., chosen to obtain a desired sensitivity and specificity). As another example, a reference value can be determined based on statistical simulations of samples. A particular value for a cutoff, threshold, reference, etc. can be determined based on a desired accuracy (e.g., a sensitivity and specificity).

The term "sequence imbalance" or "aberration" as used herein means any significant deviation as defined by at least one cutoff value in a quantity of the clinically relevant chromosomal region from a reference quantity in maternal plasma DNA of a pregnant woman. A sequence imbalance can include chromosome dosage imbalance, allelic imbalance, mutation dosage imbalance, copy number imbalance, haplotype dosage imbalance, and other similar imbalances.

A "genomic characteristic of a fetus" can refer to properties of fetal DNA, e.g., of fetal DNA fragments and/or a fetal genome. The genomic characteristic can be genetic and/or epigenetic. As examples, the genomic characteristic can include a sequence imbalance, a genotype (e.g., an inherited allele), a haplotype (e.g., an inherited haplotype), a mutation (e.g., a mutated allele), and a methylation level (e.g., at a particular site, as may be inferred based on gene imprinting). Such characteristics can be determined by analyzing DNA in a biological sample of a pregnant female.

A "genomic characteristic of a pregnancy" can be a pregnancy-associated disorder. A "pregnancy-associated disorder" includes any disorder characterized by abnormal relative expression levels of genes in maternal and/or fetal tissue or by abnormal clinical characteristics in the mother and/or fetus. These disorders include, but are not limited to, high blood pressure, gestational diabetes, infections, preterm labour, pregnancy loss/miscarriage, fetal growth restriction (FGR), preeclampsia (Kaartokallio et al. Sci Rep. 2015; 5:14107; Medina-Bastidas et al. Int J Mol Sci. 2020; 21:3597), intrauterine growth restriction (Faxen et al. Am J Perinatol. 1998; 15:9-13; Medina-Bastidas et al. Int J Mol Sci. 2020; 21:3597), invasive placentation, pre-term birth (Enquobahrie et al. BMC Pregnancy Childbirth. 2009; 9:56), hemolytic disease of the newborn, placental insufficiency (Kelly et al. Endocrinology. 2017; 158:743-755), hydrops fetalis (Magor et al. Blood. 2015; 125:2405-17), fetal malformation (Slonim et al. Proc Natl Acad Sci USA. 2009; 106:9425-9), HELLP syndrome (Dijk et al. J Clin Invest. 2012; 122:4003-4011), systemic lupus erythematosus (Hong et al. J Exp Med. 2019; 216:1154-1169), and other immunological diseases of the mother.

The term "machine learning models" may include models based on using sample data (e.g., training data) to make predictions on test data, and thus may include supervised learning. Machine learning models often are developed using a computer or a processor. Machine learning models may include statistical models.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within embodiments of the present disclosure. The upper and lower limits of these smaller ranges may independently be included or excluded in the range, and each range where either, neither, or both limits are included in the smaller ranges is also encompassed within the present disclosure, subject to any specifically excluded limit in the stated range. Where the stated range includes one or both of the limits, ranges excluding either or both of those included limits are also included in the present disclosure.

Standard abbreviations may be used, e.g., bp, base pair(s); kb, kilobase(s); pi, picoliter(s); s or sec, second(s); min, minute(s); h or hr, hour(s); aa, amino acid(s); nt, nucleotide(s); and the like.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the embodiments of the present disclosure, some potential and exemplary methods and materials may now be described.

DETAILED DESCRIPTION

As explained above, NIPT can suffer problems due to low fetal fraction in some samples. Aside from the low fetal DNA fraction, the relatively fragmented nature of cell-free DNA would be another potential limitation of NIPT in certain circumstances. For example, the short DNA molecules make it technically challenging to directly construct a fetal genetic/epigenetic haplotype from maternal plasma. The length of cell-free DNA was revealed to be mostly below 200 bp (Lo et al. Sci Transl Med. 2010; 2:61ra91) by massively parallel short-read sequencing (Illumina). Sequencing short plasma cell-free DNA would not be efficient for analysing genetics and/or epigenetics in a haplotype manner. This is because single nucleotide polymorphisms (SNPs) or CpG sites are typically separated from their nearest SNP or CpG sites by hundreds or thousands of base pairs. Thus, NIPT also suffers from problems due to the short size of cell-free DNA fragments typically used. Typical NIPT analysis is of particle-free DNA. An improved approach would allow one to simultaneously obtain long DNA molecules and enrich fetal signals for the NIPT.

Instead of using cell-free DNA molecules that are floating free of any particle (vesicle), embodiments can use cell-free DNA molecules within a particle. The use of such a particular type of cell-free DNA in a particle (also referred to as particle cfDNA) allows for an ability to capture and use long fetal DNA fragments, and potentially to enrich a sample for long fetal DNA fragments, i.e., to increase the percentage of long DNA in the sample. The selection of particle DNA fragments having a size greater than a size threshold can increase the fetal DNA fraction.

Some embodiments can perform certain purification steps to enrich for the particle DNA, e.g., a physical separation (such as filtration or centrifuging), washing with an ionic solution (e.g., saline), and/or nuclease treatment. The purification by itself or in combination with selection of long DNA (i.e., greater than a size threshold) can result in an increase in the fetal DNA fraction, thereby allowing greater accuracy and/or a more efficient assay (e.g., a smaller sample can be used to achieve the same accuracy). This is possible since any statistical analysis (e.g., change from an expected/normal value) involving the fetal DNA can be detected more easily since the higher fetal fraction causes the change to be more pronounced.

The analysis of long DNA fragments can be enhanced or enabled by using long read sequencing techniques such as single molecule sequencing, including nanopore sequencing (e.g., Oxford Nanopore Technologies) and single-molecule real-time sequencing (e.g., Pacific Biosciences), synthetic long-read sequencing (Illumina), and linked-read technology (10× genomics, Tell-seq), the latter two involving linking a set of short DNA fragments as originating from a longer fragment. Additionally or alternatively, long DNA molecules can be analyzed by fragmenting them and then using a short-read sequencing technique.

I. Extracellular Particles

The existence of membrane-bound or nonmembrane-bound extracellular particles (EP) in bodily fluids (e.g., plasma) has been reported before (Malkin et al. Cell Death Dis. 2020; 11:584). Cells can release such extracellular particles in various ways. For example, during apoptosis, cells will release apoptotic bodies, a type of large extracellular vesicle. Some active release processes, such as secretion, will create microvesicles. Exosomes, the major contributor of small EPs, have a different way of forming membrane vesicles that use a intracellular membrane instead of the plasma membrane. Because of the different ways to form EVs, the size of them will be quite different.

Most studies on EPs have focused on mRNA and miRNA (Zhou et al. Sig Transduct Target Ther. 2020; 5:144). A practically meaningful approach based on EP-associated DNA in a clinical context regarding NIPT is still not available. The size of EPs varies widely, with a diameter from a few nanometres to a few micrometres. Those particles could broadly be classified into nanoparticles (e.g., exosomes), microparticles (microvesicle), and apoptotic bodies according to their diameter size. Nanoparticles are typically referred to as EPs smaller than 100 nm; microparticles are usually referred to as those ranging from 100 nm to 1 μm, and apoptotic bodies are usually referred to as those from 1 μm to 5 μm in diameter size. In a less precise manner, EPs can be roughly separated into two classes, i.e., large-sized EPs (>=200 nm) (LEPs) and small-sized EPs (<200 nm) (SEPs). The subcellular origin of LEPs and SEPs are different (e.g., LEPs are formed by using cell membrane, while SEPs are formed with intercellular membrane or proteins); thus, the genetic information associated with them can be treated differently.

A few groups attempted to test the possibility of using LEP-associated DNA in the plasma of pregnant women. In early studies, Bischoff et al. reported that the fetal DNA fraction showed some increase through analyzing DNA from nucleic acid positive non-cellular particle fraction sorted by flow cytometry (Bischoff et al. Hum Reprod Update 2005; 11:59-67). This study used real-time PCR to quantify DYS1 (ChrY) and GAPDH sequences for measuring fetal fraction of male pregnancies but did not perform any analysis using the positive non-cellular particle fraction.

Orozsco et al. (Orozco et al. Placenta. 2009; 30:10; Goswami et al. Placenta. 2006; 27:1.) demonstrated that DNA-associated LEPs of placental origin (leukocyte antigen G positive (HLA-G+) or placental alkaline phosphatase positive (PLAP+)) were significantly increased in maternal plasma of pregnant subjects compared to plasma from non-pregnant controls. Orozsco et al. used antibodies and PicoGreen (double-stranded DNA fluorescent dye) to detect placental LEPs but was not able to uncover genetic and epigenetic information of fetal DNA molecules. Moreover, both studies were based on flow cytometric sorting, which is only suitable for analyzing LEPs with a diameter size>1 μm, thus resulting in a low-resolution LEP separation.

However, a more recent report using sequencing to analyze aneuploidies showed inferior results for EP-associated DNA. This other report used massively parallel sequencing of EP-associated DNA in maternal plasma to try to detect fetal chromosomal aneuploidies and single-gene diseases (Zhang et al. BMC Med Genomic. 2019; 12:151). However, the analysis of EP-associated DNA was shown to be inferior to the analysis of normal cell-free DNA (i.e., particle-free cfDNA). The fetal DNA fraction in EP-associated DNA was 2-fold lower than that in plasma cell-free DNA (Zhang et al. BMC Med Genomic. 2019; 12:151). Moreover, the length of EP-associated DNA was shorter than cfDNA (median size: 152.4 bp vs 168.5 bp), so that each EP-associated DNA fragment would even give less information than cfDNA. Such results suggested that EPs were not beneficial for use of long DNA fragments and provided a lower fetal DNA fraction, and thus indicated EPs were not beneficial for performing NIPT.

More recently, Lucas Brandon Edelman disclosed a patent application regarding methods for analysing circulating microparticles (WO2020002862A1) which briefly discussed the potential application in NIPT without real examples and disclosed implementation steps. The techniques presented in Lucas Brandon Edelman's disclosure focused on barcoding DNA molecules inside microparticles, allowing for tracing whether the two or more DNA molecules would be derived from the same microparticle. The concept of technology is analogous to "linked-read technology" developed by 10× Genomics (Hui et al. Clin Chem. 2017; 63:513-524). However, the disclosure by Lucas Brandon Edelman did not select a particular subpopulation of microparticles based on microparticle physical and/or biological properties for enhancing the performance of NIPT or selection of a subpopulation of nucleic acid molecules.

Taken together, there is still a lack of practically meaningful approaches. This disclosure reports new methods that can selectively analyze a subset of extracellular particles that concurrently enrich DNA molecules of interest (e.g., fetal DNA molecules) and long DNA molecules, e.g., by selecting long DNA molecules, within which fetal DNA is enriched. Surprisingly, high fetal fraction, greater than 50%, can be achieved according to techniques disclosed herein. These methods included sequencing DNA molecules associated with extracellular particles and analyzing the genetic and/or epigenetic information, which could substantially enhance the diagnostic power for NIPT. The current disclosure would be beneficial to groups at risk for low fetal DNA fraction, which could be caused by, but not limited to, the high maternal body mass index (Hui et al. Prenatal Diagnosis 2020; 40:155-163). Our disclosed technology might also allow NIPT to be performed than is customarily recommended by many authorities, e.g., 10 weeks.

II. Workflow for EP Separation

This disclosure provides various techniques for obtaining EP DNA (e.g., DNA includes of an EP, as opposed to DNA bound to an outside of an EP) using one or more purification steps, which can provide particles of desirable size and content. Results in later sections shows that certain purification and/or in silico techniques provide surprising results for the ability to consistently increase the fetal fraction above 40% and to obtain long DNA fragments, which can enable new functionality, e.g., for determining haplotypes in more efficient, accurate ways. Various experimental procedures can be used to obtain extracellular particles (EPs), potentially of a particular size.

FIG. 1 shows a first example workflow 100 of EP separation and analysis. As shown, a blood sample 102 in a sample holder undergoes centrifuging at 1600 g for 10 mins, which is performed twice. This initial centrifuging step creates a pellet at the bottom of the vial, where the pellet includes live cells and dead cells. After removing the pellet of cells, an optional filtration step 106 can filter (e.g., using a 5 μm filter) the remaining substance (supernatant) to ensure no cells will go to the next step. This intermediate supernatant (plasma) after filtration includes LEV DNA but heavily diluted with vesicle-free and SEV DNA. Typical NIPT tests are based on the liquid fraction, i.e., supernatant from 1600 g×2 (twice) for 10 minutes each or 1600 g for 10 minutes+16,000 g for 10 minutes. If the plasma is collected at 1600 g for 10 minutes (e.g., to remove cells)+16,000 g for 10 minutes, then the LEV portion is largely removed, and the remaining plasma can be considered as LEV-free DNA. Other centrifuging protocols at difference force (rotational speed), time, and number of centrifuging steps can vary.

At centrifuging step 108, the filtered supernatant can be centrifuged at 20,000 g for 40 minutes and the pellet enriched for LEVs is collected. LEV pellets can be collected directly and include some plasma carry over, labeled as LEV without further treatment, corresponding to a sample 110. The remaining supernatant would include SEVs and particle-free DNA. As another example, an ionic wash (e.g., using phosphate buffered saline, PBS) can be used to provide LEV with wash, corresponding to sample 120. The wash can remove some particle-free DNA. After the ionic wash, the sample can be subjected to further centrifuging (e.g., 20,000 g at 40 minutes) to further separate out LEVs.

As a further treatment, after performing the ionic wash, a nuclease treatment (e.g., with DNase I) can be applied. The nuclease treatment can further breakdown nucleic acids that are not within a membrane of the LEVs, thereby allowing such particle-free DNA to be removed, resulting in a sample 130. Such DNA bound to an outside of an EV can be EV-associated DNA, but a goal of purification can be to remove such EV-associated DNA to obtain a sample that is highly enriched for DNA within a membrane of an EV. Thus, with more treatment, the outside DNA can be removed further and further. The DNA in any of the sample can be isolated for sequencing.

Typically, DNA in plasma is not subjected to a physical fragmentation since the DNA is naturally fragmented. However, it has been realized that long DNA can occur in the vesicles. In order to sequence such long DNA (e.g., above 600 bp) on certain platforms, e.g., Illumina or other short read sequencing platforms, some implementations can perform a physical fragmentation process so that such DNA can be sequenced. Example fragmentation techniques can include using mechanical shearing, enzymatic fragmentation such as Tn5 transposase based tagmentation, DNASE1, DNASE1L3, and/or DFFB treatments, light, sonication, or chemical DNA fragmentation using a combination of a divalent metal cations such as magnesium or zinc and heat to break nucleic acids. In some embodiment, bisulfite treatment could be used for fragmenting DNA molecules. The level of fragmentation can shorten an average fragment length to be below a specified size (e.g., 600 bp) such as down to 200 bp. In one implementation, long read sequencing techniques can be used, such as single molecule sequencing (e.g., using a nanopore, or single-molecule real-time sequencing (e.g., from Pacific Biosciences)). In addition or instead of sequencing, probe-based techniques, such as PCR, can be used.

The bioinformatic analysis can be of various types and include multiple stages. The analysis can be genetic and/or epigenetic. For example, the sequencing can provide sequence reads that are aligned to a reference genome to determine genomic locations of the reads. Such sequence reads can be analyzed for a variety of properties at certain positions, sites, or regions, such as counts, size of DNA fragments, methylation level(s), ending positions in a genome, amount of overhand (jaggedness) at ends of a fragment, and motifs at the end of fragments, e.g., 3-mers or 4-mers at the end of the DNA fragments. Such fragment end analysis may be preferably used when a separate physical fragmentation is not performed. Such properties can be used to detect various abnormalities, conditions, or disorders, including copy number aberrations, and sequence variants (including mutations, which may be single nucleotide or larger), haplotype inheritance.

Figure 2:
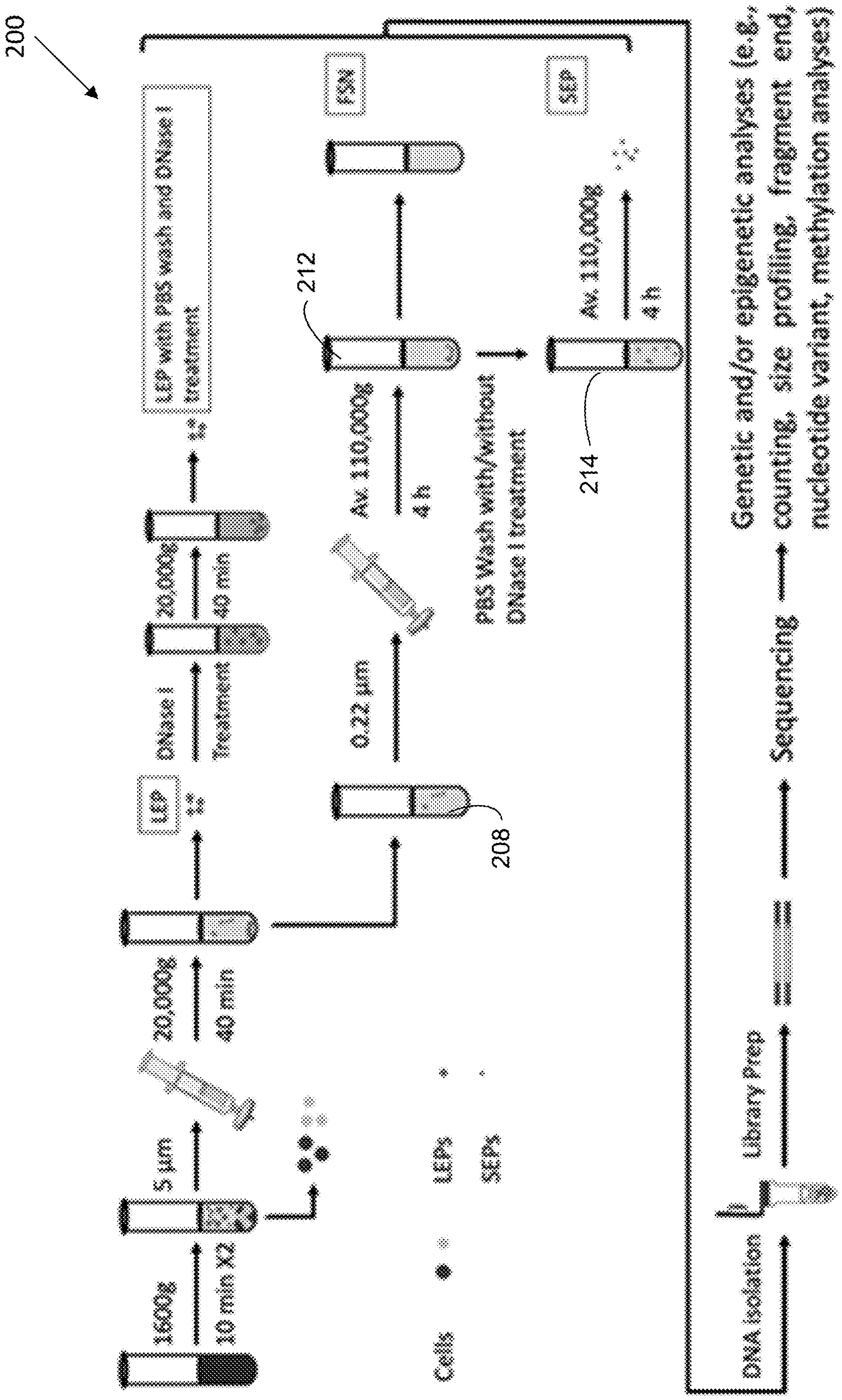
FIG. 2 shows a second example workflow of EP separation and analysis.

FIG. 2 shows a second example workflow 200 of EP separation and analysis. Workflow 200 is similar to workflow 100. The exemplary methods include, but are not limited to, two aspects: (1) selecting a desired subset of EPs that enrich DNA molecules of fetal origin and (2) performing the genetic and/or epigenetic analysis of those selected DNA molecules. For the first aspect, the selection of EPs could be carried out based on their diameter sizes, e.g., selecting EPs with a diameter of 200 nm to 5 μm (LEPs) and <200 nm (SEPs). As examples, such selection of EPs can be performed based on centrifugation and ultracentrifugation.

As shown, the procedure to obtain the LEP with wash and/or nuclease treatments is the same as for sample 120 and sample 130 for workflow 100. For the supernatant 208, including SEPs and particle-free DNA, a filtration (e.g., using 0.22 micrometer filters) is performed, followed by centrifuging at 110,000 g for four hours to obtain a sample 212. The liquid fraction of sample 212 can be used as the final supernatant (FSN) that includes mostly particle-free DNA. The pellet from sample 212 can be further treated (e.g., with an ionic wash and/or a nuclease treatment) to obtain a sample 214, which can be centrifuged at 110,000 g for four hours again. The remaining pellet can be enriched for SEPs, which can be extracted and analyzed, e.g., as described later.

A. Purifications of Sample for EPs

In various implementations, EPs can be separated into different size populations based on differential centrifugations or other physical separation techniques, such as filtration or flow cytometry. Such physical separations can be performed in any of the methods described herein. In one instance, the collected blood can be subjected to two runs of 1,600 g centrifugation for 10 minutes each to remove the cells. The obtained supernatant can be filtered through a filter (e.g., a 5 μm mesh polycarbonate filter) to minimize cell contamination. The filtered supernatant can then be centrifuged at 20,000 g for 40 minutes to collect LEPs. LEPs can be treated, e.g., with DNase I, preceded by or followed by an ionic wash (e.g., a PBS washing), thus eliminating the DNA molecules outside of particles. The treatment may only be the ionic wash. The DNase I and PBS treated materials can be further centrifuged at 20,000 g for 40 minutes. The remaining plasma can be filtered, e.g., using one or more 0.22 μm mesh polycarbonate filters, and centrifuged at 110,000 g for 4 hours to collect SEPs. SEPs can be further washed with an ionic solution, such as PBS, (with or without DNase I treatment) and re-centrifugated with 110,000 g for 4 hours to purify SEPs. DNA from both LEPs, SEPs, and particle-free cfDNA from the FSN can be subjected to DNA extraction and sequencing.

1. Size Separations

The diameter size selection of EPs can be conducted in various ways and may use multiple techniques, e.g., including but not limited to density gradient centrifugation, size exclusion chromatography, polymer-based precipitation (e.g., using ExoQuick), filtration (e.g., including washing filter to get EPs captured by the filter), ultrafiltration, tangential flow filtration, asymmetric flow field-flow fractionation, and affinity-based methods.

As the sedimentation rate of a particle would depend on the particle size at a certain centrifugal force and liquid viscosity, EPs collected at a certain centrifugal force and liquid viscosity would reflect the particle sizes. As shown in FIG. 2, after removing cells with 1,600 g centrifugation and 5 μm filter, EPs could be collected with 20,000 g centrifugation, followed by the DNase I treatment and phosphate buffered saline (PBS) washing. The DNase I and PBS treated materials can be further centrifugated with the previous 20,000 g centrifugation to collect LEPs. The remaining plasma can be filtered through the 0.22 μm filters (e.g., mesh polycarbonate filter) and centrifuged at 110,000 g to collect the supernatant (e.g., the final supernatant (FSN)), which is enriched for particle-free cfDNA molecules.

Particles from the previous 110,000 g centrifugation can be washed with anionic solution, such as PBS, (with or without DNase I treatment) and re-centrifuged with 110,000 g to collect SEPs. Therefore, one could obtain LEPs, SEPs and FSN as separate portions from the procedure mentioned above. The corresponding DNA molecules can be extracted by DNA extraction kits (e.g., QIAamp Circulating Nucleic Acid Kit (QIAGEN)), namely LEP-associated DNA, SEP-associated DNA, and particle-free cfDNA.

As various examples, the target diameter sizes of EPs could include, but not limited to, nm to 100 nm, 30 nm to 150 nm, 30 nm to 200 nm, 100 nm to 1 μm, 100 nm to 3 μm, 100 nm to 5 μm, 1 μm to 3 μm, 1 μm to 5 μm or other diameter combinations. Different centrifugal forces could be used according to the target diameter sizes of EPs, for example but limited to, 100 g, 200 g, 300 g, 400 g, 500 g, 600 g, 700 g, 800 g, 900 g, 1,000 g, 1,100 g, 1,200 g, 1,300 g, 1,400 g, 1,500 g, 2,000 g, 3,000 g, 4,000 g, 5,000 g, 10,000 g, 20,000 g, 40,000 g, 50,000 g, 100,000 g, 200,000 g, 300,000 g, 400,000 g, 500,000 g, etc or with different combinations. Different time durations of centrifugations could be used, for example, but not limited to 1 s, 5 s, 10 s, 20 s, 30 s, 40 s, 50 s, 1 min, 5 min, 10 min, 20 min, 30 min, 40 min, 50 min, 1 h, 2 h, 3 h, 4 h, 5 h, 10 h, 20 h, 1 d, 2 d, etc. Such example values can be used with any example techniques described herein.

As mentioned above, filtration can also be used. Example filter sizes are 2 um, 3 um, 4 um, 5 um, 6 um, 7 um, 8 um, 9 um, 10 um, etc, corresponding to different filtering strengths. In some implementations, the LEV of interest are less than 1 um, and potentially greater than 200 nm. Such example values can be used with any example techniques described herein.

The centrifugal force and filter size are two important parameters for obtaining the desired population of vesicles such as LEVs. In various embodiments, the centrifugal force for a second centrifugation (e.g., centrifuging step 108) could be, but not limited to, 10,000 g, 11,000 g, 12,000 g, 13,000 g, 14,000 g, 15,000 g, 16,000 g, 17,000 g, 18,000 g, 19,000 g, 20,000 g, etc. for precipitating and enriching the LEVs, following a first centrifugation with a centrifugal force of but not limited to 500 g, 600 g, 700 g, 800 g, 900 g, 1,000 g, 1,100 g, 1,200 g, 1,300 g, 1,400 g, 1,500 g, 1,600 g, 1,700 g, 1,800 g, 1,900 g, 2,000 g, 5,000 g, 10,000 g, etc., for precipitating and removing cells. One could add a first filter step to remove the unwanted particles between any two centrifugations, with a size of, but not limited to, 1 um, 2 um, 3 um, 4 um, 5 um, 6 um, 7 um, 8 um, 9 um, 10 um, etc. One could add a second filter step to further enrich the wanted particles between any two centrifugations, with a size of, but not limited to, 0.1 um, 0.2 um, 0.3 um, 0.4 um, 0.5 um, 0.6 um, 0.7 um, 0.8 um, 0.9 um, 1 um, etc. The time duration for centrifugation could be not limited to 1 s, 5 s, 10 s, 20 s, 30 s, 40 s, 50 s, 1 min, 5 min, 10 min, 20 min, 30 min, 40 min, 50 min, 1 h, 2 h, 3 h, 4 h, 5 h, 10 h, 20 h, 1 d, 2 d, etc. The order of centrifugations and filtrations can be variable. The purity of DNA associated with LEVs could be further enhanced using ionic buffer wash (PBS wash) and/or enzymatic digestion (e.g., DNASE1).

2. Enrichment

In certain embodiments, the desired population of EPs can be further enriched prior to, after or not combined with centrifugation. The enrichment can be DNA from a particular type of cell. For example, one can use protein markers (e.g., syncytin-1 and placental alkaline phosphatase (PLAP)) to sort out EPs originating from fetal tissue, such as syncytiotrophoblasts, using, but not limited to, immunoprecipitation-based, immunoaffinity-based, aptamer affinity-based, flow cytometry-based methods (e.g., fluorescence-activated cell sorting (FACS)), or microfluidics-based technologies. When performing NIPT, enrichment for syncytiotrophoblasts may be desired as such cells are specific to placenta and carry some surface protein marker (e.g., PLAP) facilitating the selection. For example, a fluorophore (e.g., PerCP) can be used to stain the PLAP via its specific antibody.

Such identification of particles that are derived from the fetus can be used to enrich a sample for fetal DNA. Further, DNA from a given particle can be identified (e.g., barcoded) so that after fragmentation, the small fragments from a same particle can be assembled back together to create a single long read. For example, the sequence reads can be aligned to a reference genome, and if two reads are adjacent to each other (e.g., within 1, 2, 3, 4, or 5 bases) and from a same particle, it can be assumed they came from the same long fragment, thereby providing a sequence read that is greater than 600 bp. Such a technique can be referred to as linked-read sequencing.

3. Treatments to Further Purify

Various treatments can be performed at various times, e.g., before or after physical separation techniques, such as centrifugation. Such treatments may be performed individually or together, e.g., serially, and may be applied more than once, potentially with other treatments or separation steps in between.

One treatment is an ionic wash. The washing buffer (e.g., phosphate-buffered saline) can have a similar osmolarity, ionic strength, and/or pH as plasma. Such a treatment can remove particle-free nucleic acids in a sample and/or bound to the outside of an EV. In other embodiments, other solutions can be used for washing a sample (e.g., of LEPs or SEPs), including but not limited to normal saline, HEPES (4-(2-hydroxyethyl)-1-piperazineethanesulfonic acid), MOPS (3-(N-morpholino) propanesulfonic acid), and TBS (Tris-buffered saline).

Another example treatment is a nuclease treatment, which can break down particle-free nucleic acids in a sample and/or bound to the outside of an EV. Once such nucleic acids are broken down and removed from the surface of an EV, they can be removed, e.g., by a wash or by a size selection process, such as centrifugation.

As examples of nuclease treatments, DNase I treatment could be applied during EPs' isolation to eliminate the DNA outside EPs. Other DNA nucleases could be used, including but not limited to TREX1 (Three Prime Repair Exonuclease 1), AEN (Apoptosis Enhancing Nuclease), EXO1 (Exonuclease 1), DNASE2 (Deoxyribonuclease 2), ENDOG (Endonuclease G), APEX1 (Apurinic/Apyrimidinic Endodeoxyribonuclease 1), FEN1 (Flap Structure-Specific Endonuclease 1), DNASE1L1 (Deoxyribonuclease 1 Like 1), DNASE1L2 (Deoxyribonuclease 1 Like 2) and EXOG (Exo/Endonuclease G).

B. Analysis

For the second aspect of this exemplary workflow in FIGS. 1 and 2, DNA isolated from different EP sources can be subsequently analyzed, e.g., using PCR (including real-time PCR or digital PCR) or sequencing platforms, to uncover genetic and/or epigenetic information inside. After procedures that isolate LEPs or SEPs, the membranes on the particles can be disrupted, thereby exposing the DNA fragments. The DNA fragmented can then be analyzed. Such analysis can take advantage of an enrichment in long DNA fragments and/or an increase in the fetal DNA fraction.

In this disclosure, EPs can be used for enriching long DNA molecules, as we envisioned that EPs' protective environment would prevent their associated long DNA molecules from nuclease degradation (e.g., reducing the accessibility of DNA nucleases). A long DNA molecule could be defined as a size of greater than a size threshold, such as but not limited to 200 bp, 300 bp, 400 bp, 500 bp, 600 bp, 700 bp, 800 bp, 900 bp, 1 kb, 2 kb, 3 kb, 4 kb, 5 kb, 10 kb, 20 kb, 30 kb, 40 kb, 50 kb, 100 kb, 500 kb, 1 Mb, etc.

DNA fragments of a desired size range can be selected physically (e.g., using electrophoresis) or in silico (e.g., by determining a length of a DNA fragment and selecting fragments within the size range). The electrophoresis can be performed before the genomic analysis, e.g., before sequencing or PCR analysis.

In order to analyze long DNA on a short read platform, DNA collected from selected EPs can be subjected to DNA shearing (e.g., physically, enzymatically, or chemically) so that long DNA molecules present in EPs could be sequenced by short-read sequencing technologies (e.g., Illumina). Alternatively, DNA collected from selected EPs can be subjected to long-read sequencing technologies, including, but not limited to, nanopore sequencing (e.g., Oxford Nanopore Technologies) and single-molecule real-time sequencing (e.g., Pacific Biosciences). Analyses for the DNA molecules could include but are not limited to counting, size profiling, fragment end analysis, nucleotide variant analysis, and epigenetic analysis, or other techniques described herein.

As shown and described herein, some techniques for analyzing EPs can allow for not only enriching DNA molecules of fetal origin but also long DNA molecules, thus facilitating the genetic and/or epigenetic analyses. Previous reports could not achieve these purposes, e.g., because of the following reasons: the separation of desired EPs enriching the tissue-specific DNA molecules had not been established; and long DNA molecules inside EPs had not been effectively analyzed. Techniques described herein can use long-read sequencing technologies for assessing long DNA inside EPs or artificially fragmented long DNA molecules inside EPs such that short-read sequencing can be suited to evaluate EP-associated long DNA molecules.

Additionally, certain methods do not efficaciously remove the contaminant DNA outside of EPs. Certain implementations can combine DNase I treatment with PBS washing followed by re-centrifugation to eliminate DNA outside of EPs. An improved efficiency can result from DNase I digestion being more efficient on naked DNA than histone-protected DNA; further saline (e.g., PBS) washing could remove remaining nucleosomes after DNase I treatment.

The significantly and surprisingly higher concentration can provide greater statistical accuracy, e.g., since the background noise of maternal DNA is reduced, possibly to a minority. Additionally or alternatively, any assay can be more efficient (e.g., using a smaller sample or using less reagents) since fewer DNA fragments are needed to analyze for a same level of accuracy. For example, with an increase in the fetal DNA fraction, sequence imbalance (or other genomic characteristic) can be detected sooner since a large portion of the DNA fragments will be from the fetal tissue that has the imbalance.

Further, the analysis can benefit from the use of long DNA fragments. Such long DNA fragments can be useful for haplotyping since heterozygous loci from multiple fragments will overlap. A fetal genome can be reconstructed in this manner. Additionally, the long DNA molecule would carry more CpG sites, facilitating the determination of plasma DNA molecules of placental origin based on their respective methylation patterns. A fetal methylome can be thus reconstructed using the methylation patterns along each long DNA molecule.

Additionally, since various subsamples can be generated (e.g., LEPs, SEPs, and FSN) from a single blood sample, measurements using all the samples can be combined or compared. For example, a measurement of a genomic and/or epigenetic characteristic can be performed with each sample and a majority or unanimity in the determination can be used to determine the classification. In this manner, the sensitivity and specificity can be improved.

C. General Results

Table 1 provides a summary of differently prepared LEP samples (different sample types) from a blood sample of a same patient in the 3rd trimester with a male fetus. Three different LEP DNA samples were collected as described before. In table 1, the DNA concentration refers to the initial DNA concentration after isolation, i.e., how much of a particular type of DNA was present per ml plasma (generated by centrifuging 1600 g 2×). The input refers to how much DNA was used in the library preparation. Total mapped reads refers to how many DNA fragments mapped to the human genome after sequencing.

TABLE 1

Results for three different sample types.

| Sample | DNA Con. (ng/ml) | Input (ng) | Total Mapped Reads |
|---|---|---|---|
| LEP Without Further Treatment | 2.11 | 4.2 | 5,479,732 |
| LEP With PBS Wash | 0.96 | 2.0 | 4,026,623 |
| LEP With PBS Wash and DNase I Treatment | 0.38 | 1.1 | 2,976,256 |

The DNA concentration decreases with further treatment of a PBS wash and further reductions with a DNase I treatment. This shows the reduction in DNA outside of the LEV. Surprisingly, the number of mapped reads does not decrease as much as the reductions in the DNA concentration and the input DNA for preparing the library. Thus, a higher percentage of usable DNA is in the final sample after washing and nuclease treatment.

According to some reports, mitochondrial DNA is quite enriched in LEPs. We analyzed the contribution of mitochondrial DNA and nuclear DNA in the LEP DNA for the three different types of samples. The major contributor is still the nuclear DNA across all three samples, but the amount does decrease with treatment (e.g., PBS wash treatment and the DNase I treatment). For LEP sample without further treatment, the nuclear DNA is about 98%, while mitochondrial DNA is about 2%. For the LEP sample with PBS wash, the nuclear DNA is about 92%, while mitochondrial DNA is about 8%. For the LEP sample with PBS wash and DNase I treatment, the nuclear DNA is about 87%, while mitochondrial DNA is about 13%. These results show an enrichment in the DNA from LEPs with the further treatments.

Table 2 shows the number of DNA fragments with a fetal-specific allele and the number of DNA fragments with a shared allele (i.e., shared between the mother and the fetus). The total number of fragments is over all loci, and not just ones with a fetal-specific allele. Table 2 shows that the fetal fraction increased. The fetal fraction increased from 18% to 44% and further to 75% for the three samples. As indicated with the differently treated samples, the more non-LEV associated DNA was removed, the more fetal DNA was obtained, which indicated that DNA within LEVs is largely fetal.

TABLE 2

Number of DNA fragments with fetal and shared allele.

| Sample | Fetal | Shared | Total |
|---|---|---|---|
| LEV without treatment | 4272 | 46124 | 5,416,476 |
| LEV + PBS | 7016 | 24897 | 3,754,477 |
| LEV + DNase I | 8201 | 13045 | 2,656,690 |

III. Example Technique to Determine Fetal Fraction

Data presented herein show an increase in the fetal DNA fraction using samples purified for LEPs, as well as increased fraction for long DNA fragments. Various techniques can be used to determine the fetal DNA fraction. For example, a fetal-specific marker can be used. Examples of a fetal-specific markers include an allele or an epigenetic marker, such as a methylation level. Another example for measuring the fetal DNA fraction is using size, e.g., as described in U.S. Patent Publication No. 2013/0237431.

In this disclosure, for illustration purposes, we sequenced DNA molecules obtained from LEP without PBS washing and DNase I treatment, LEP with PBS washing, LEP with PBS washing and DNase I treatment, SEP with PBS washing and DNase I treatment, and final supernatant (FSN). We collected blood from 4 pregnant women (third trimester: n=3; first trimester: n=1). According to the embodiments in this disclosure, cell-free DNA molecules from the FSN, DNA molecules from LEP and SEP were subjected to short-read sequencing (75 bp×2 paired-end mode, Illumina), with a median of 17.41 million paired-end sequencing reads (range: 6.01-48.67 million).

The maternal buffy coat and placenta tissue genotype were obtained using microarray-based genotyping technology (HumanOmni2.5 genotyping array Illumina), and informative SNPs were identified (i.e., where the mother was homozygous (denoted as AA genotype), and the fetus was heterozygous (denoted as AB genotype)). Fetal-specific DNA fragments were identified as DNA fragments that carried fetal-specific alleles at informative SNP sites. In this scenario, the B allele was fetal-specific, and the DNA fragments carrying the B allele were deduced to be originated from fetal tissues. The number of fetal-specific molecules (p) carrying the fetal-specific alleles (B) was determined. The number of molecules (q) carrying the shared alleles (A) was determined. The fetal DNA fraction across cell-free DNA molecules from the FSN, DNA molecules from LEP and SEP in third trimester cases would be calculated by $2p/(p+q)*100\%$.

For cases without the availability of the genotype information of placenta tissues, the non-maternal DNA fraction was used for inferring the fetal DNA fraction according to our previously published method (Jiang et al. NPJ Genom Med. 2016; 1:16013 and U.S. Publication No. 2017-0081720). The non-maternal DNA fraction was defined as the fraction of DNA molecules that carry alleles different from the maternal ones.

Figure 3:
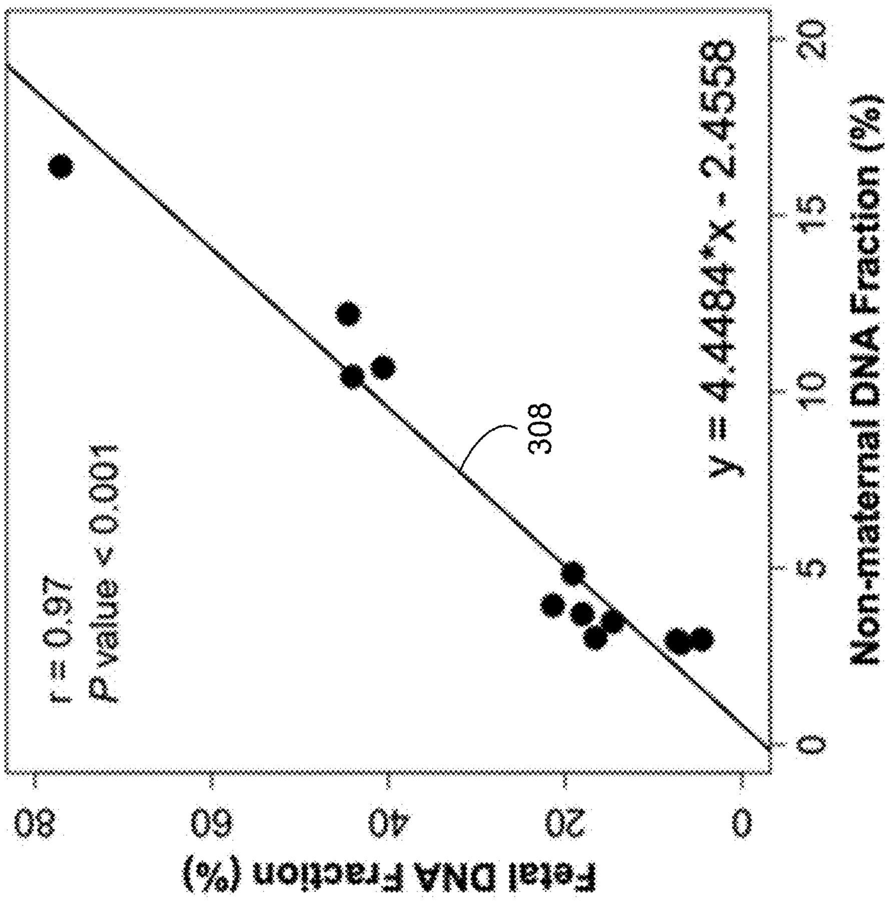
FIG. 3 shows a correlation between the fetal DNA fraction and the non-maternal DNA fraction.

FIG. 3 shows a correlation between the fetal DNA fraction and the non-maternal DNA fraction. Such a correlation can be used to determine the fetal DNA fraction when the availability of the genotype information of placenta tissues is not available, as then the non-maternal DNA fraction can be determined using the percentage of non-maternal alleles detected. For example, homozygous loci (AA) can be determined from maternal genotyping, and anything not A would be the non-maternal fraction. The fetal DNA fraction was determine using a fetal-specific marker.

To translate non-maternal DNA fraction to fetal DNA fraction, the calibration curve 308 between the fetal DNA fraction and non-maternal DNA fraction was determined using 12 third trimester samples. The formula for translating non-maternal DNA fraction to fetal DNA fraction is shown below:

$$F = X * 4.4484 - 2.4558.$$

where F represented the fetal DNA fraction and X represented the non-maternal DNA fraction.

When determining a fetal DNA fraction, various techniques can use one or more first calibration data points, which can be obtained from one or more calibration samples having a known/measured fetal DNA fraction and a determine calibration value (e.g., a size, methylation level, non-maternal fraction, etc.). In one implementation, one or more calibration data points can be obtained. Each calibration data point specifies a fractional concentration of clinically-relevant DNA corresponding to a calibration value of a parameter (e.g., relating to a size, methylation level, non-maternal fraction, etc.). A calibration function (curve) can be fit to a plurality of calibration data points (e.g., by minimizing a least squares error) such that a new measured calibration value can be input to the calibration function, which outputs an estimated fetal DNA fraction.

IV. Fetal Fraction Analysis of Extracellular Vesicles

Various procedures can be performed to purify samples for LEPs and SEPs, e.g., as described above to obtain different sample types (fractions) from a blood sample. The fetal fraction for the different sample types were determined. An analysis of fragment size was also performed. Surprisingly, long DNA was observed, counter to what had been seen in previous work. Further, an increase in fetal fraction among the long DNA was seen, which was also surprising. Various NIPT techniques can advantageously use the increased fetal DNA fraction and long DNA fragments, e.g., as described herein.

A. Enriched Fetal Fraction in LEPs

The fetal fractions in the different sample types were compared, and fetal fractions for different treatments to the LEP sample type were compared.

1. Fetal Fraction in Different Portions of EP-Associated DNA Samples

Figure 4:
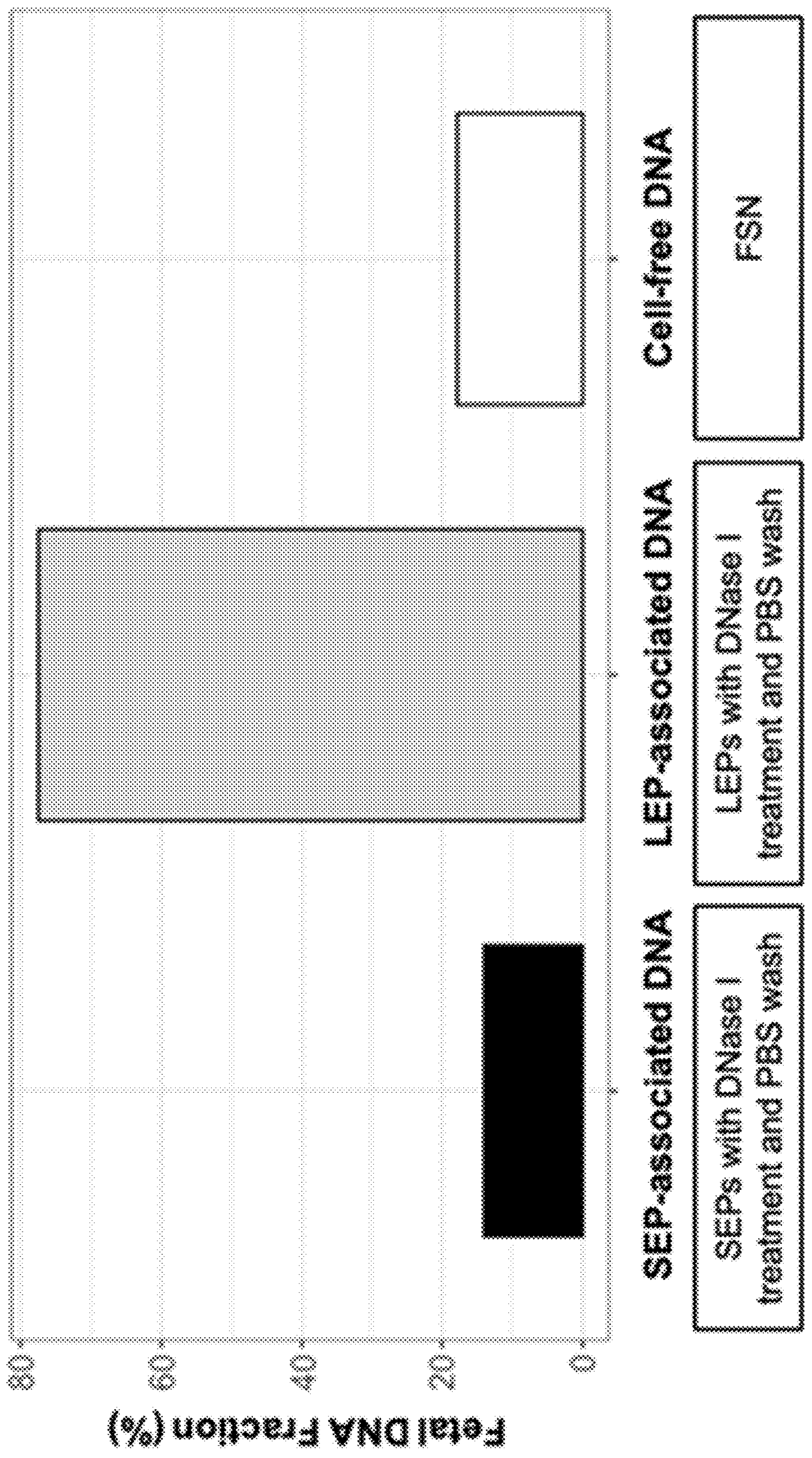
FIG. 4 shows the fetal DNA fraction in different EP-associated DNA samples.

FIG. 4 shows the fetal DNA fraction in different EP-associated DNA samples. This plot illustrates fetal DNA contributions in different EP-associated DNA samples. As indicated here, LEP-associated DNA shows substantial enrichment in DNA molecules of fetal origin, while the fetal DNA fraction of SEP-associated DNA is slightly lower than FSN. Both the SEP and LEP samples were treated with a PBS wash and a DNase I treatment.

As shown in FIG. 4, the fetal DNA fraction was 77.00% in DNA molecules obtained from LEP (i.e., LEP with PBS washing and DNase I treatment), which exhibited 5.50-fold enrichment compared to that from SEP (i.e., SEP with PBS washing and DNase I treatment; fetal DNA fraction: 14.01%). These data suggested that extracellular particles separated by a certain centrifugation setting could enrich fetal DNA molecules. In this case, DNA molecules obtained from LEP even had a higher fetal DNA fraction than that of cell-free DNA (fetal DNA fraction: 17.98%) obtained from the FSN. FSN was believed to resemble plasma DNA usually prepared for NIPT. Such a high increase shows that embodiments of this disclosure can simultaneously analyze a series of diameter size ranges of extracellular particles (e.g., LEP and SEP), thus determining the optimal diameter size ranges of particles for enriching target molecules (e.g., fetal DNA).

2. Increased Fetal Fraction in LEPs with Wash and DNase Treatment

We further demonstrated that removing the DNA outside LEPs helped enrich the fetal DNA. Such DNA outside the LEP can be removed using a saline wash and/or a nuclease treatment.

Figure 5A:
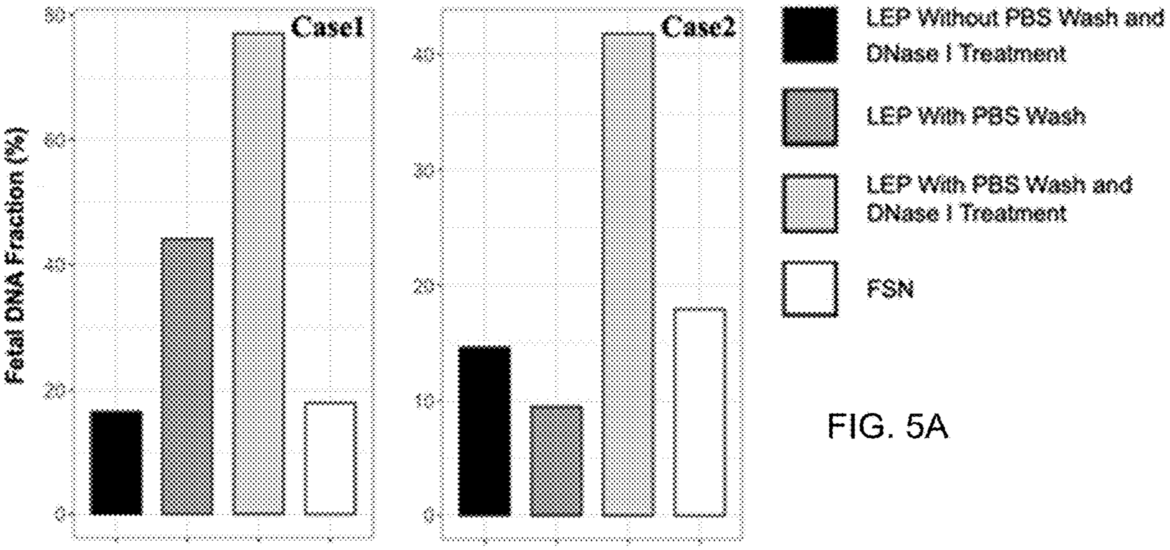
FIGS. 5A-5B show enrichment of fetal DNA in LEP-associated DNA in third trimester pregnant women.
Figure 5B:
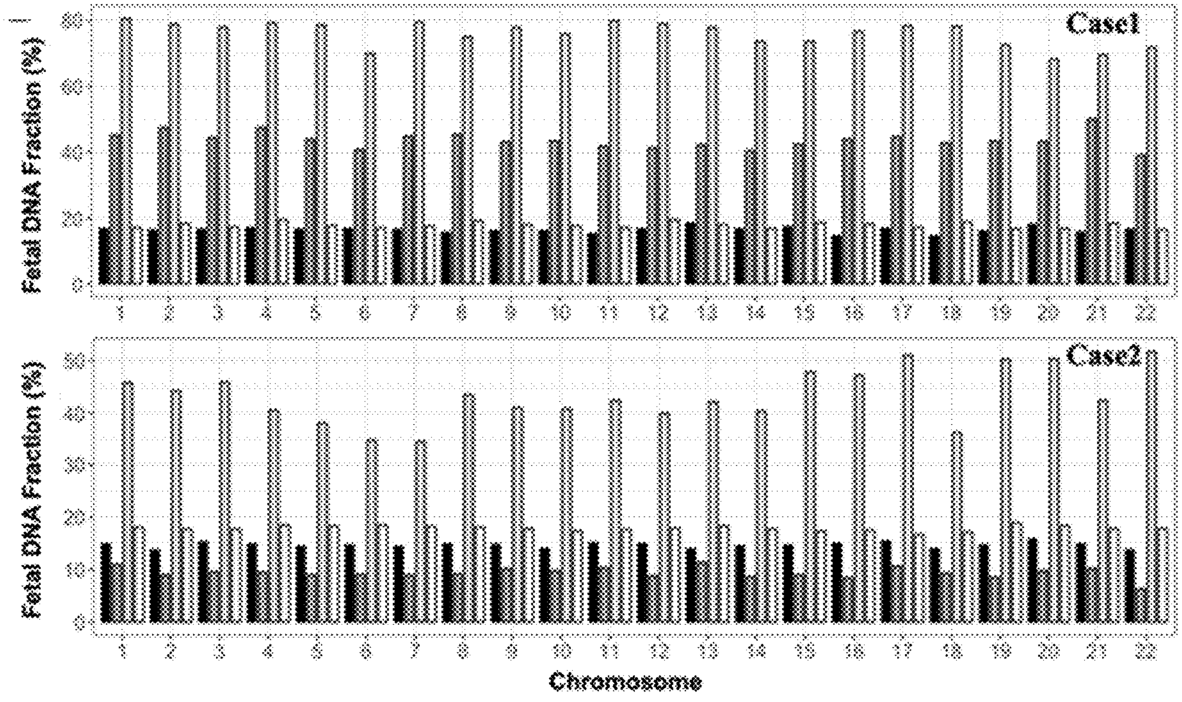

FIGS. 5A-5B show enrichment of fetal DNA in LEP-associated DNA in third trimester pregnant women. FIG. 5A shows the overall fetal DNA fractions among (1) LEP without PBS wash and DNase I treatment, (2) LEP with PBS wash, (3) LEP with PBS wash and DNase I treatment, and (4) cell-free DNA obtained from the FSN in Case 1 and Case 2. FIG. 5B shows fetal DNA fractions across different chromosomes among (1) LEP without PBS wash and DNase I treatment, (2) LEP with PBS washing, (3) LEP with PBS washing and DNase I treatment, and (4) cell-free DNA obtained from FSN in Case 1 and Case 2.

As shown in FIG. 5A, we analyzed the plasma samples from two third trimester pregnant women. The fetal DNA fractions in LEP with PBS washing and DNase I treatment sample was 77.00% and 41.83% for Case 1 and Case 2, respectively. These fetal DNA fractions were 4.65- and 2.86-fold higher than the fetal DNA fractions for LEP without PBS washing and DNase I treatment (Case 1: 16.57%, Case 2: 14.64%) and 4.28- and 2.33-fold higher than cell-free DNA obtained from FSN (Case 1: 17.98%, Case 2: 17.92%). These results indicated that LEP with PBS washing and DNase I treatment was beneficial for enriching fetal DNA from maternal plasma samples. In addition, such enrichment could be observed across the whole genome (FIG. 5B). The substantial increase for the LEP sample with wash and nuclease treatment is sustained for each chromosome, as is shown in FIG. 5B.

The enrichment of fetal DNA fraction in LEPs was also extended to first trimester pregnant women.

Figure 6A:
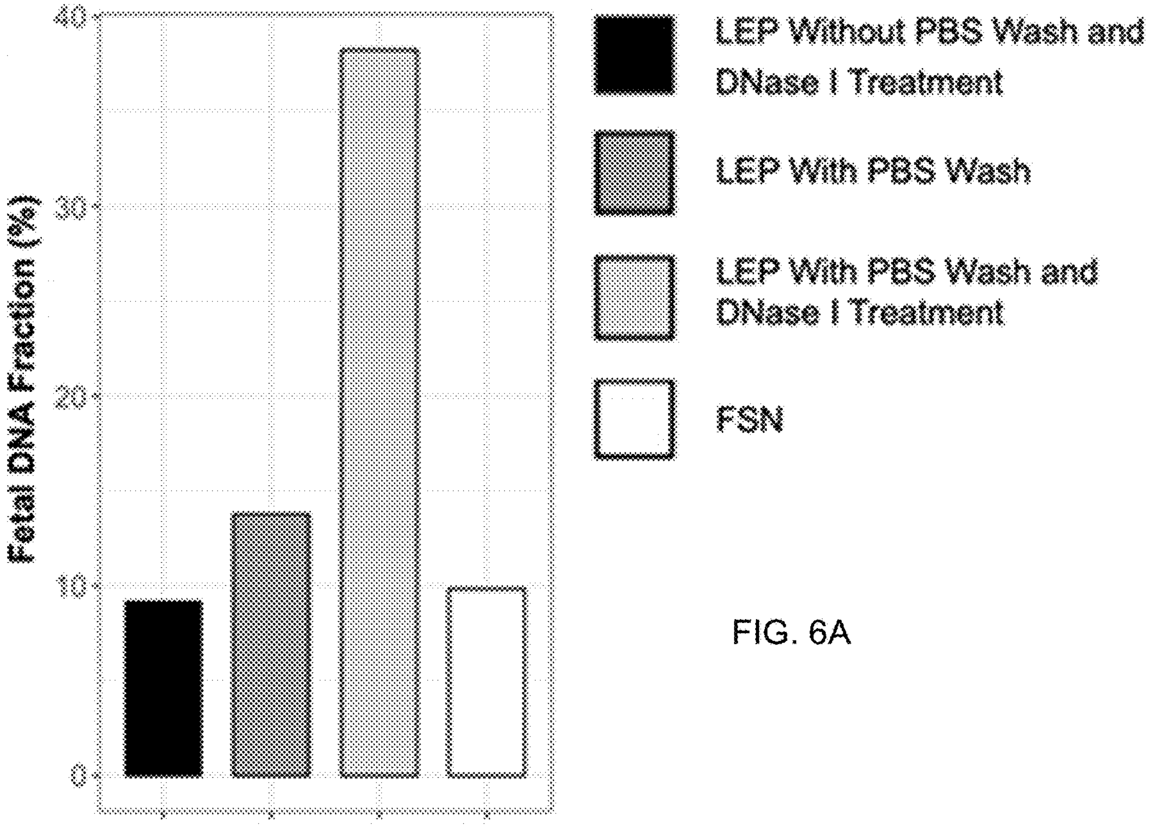
FIGS. 6A-6B show enrichment of fetal DNA in LEP-associated DNA in first trimester pregnant woman.
Figure 6B:
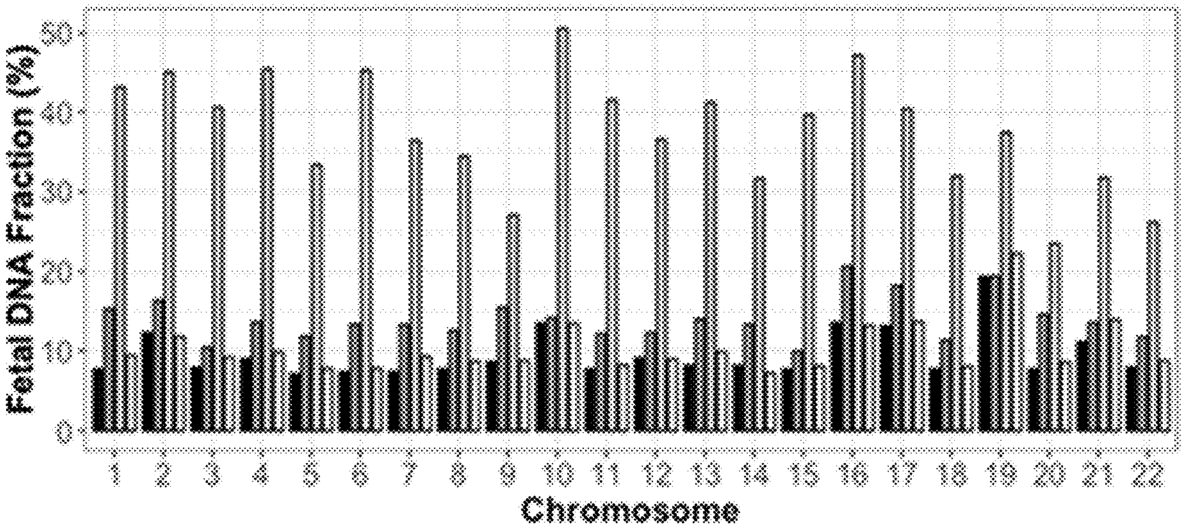

FIGS. 6A-6B shows enrichment of fetal DNA in LEP-associated DNA in first trimester pregnant woman. FIG. 6A shows overall fetal DNA fractions among (1) LEP without PBS washing and DNase I treatment, (2) LEP with PBS washing, (3) LEP with PBS washing and DNase I treatment, and (4) cell-free DNA obtained from the FSN in one first trimester case (Case 3). FIG. 6B shows the fetal DNA fractions across different chromosomes among (1) LEP without PBS washing and DNase I treatment, (2) LEP with PBS washing, (3) LEP with PBS washing and DNase I treatment, and (4) cell-free DNA obtained from FSN in one first trimester case (Case 3).

According to the analysis of the first trimester case (12 weeks), fetal DNA fractions in the LEP with PBS washing and DNase I treatment sample was found to be 38.25%, which was 4.18-fold higher than that of LEP without PBS washing and DNase I treatment (9.15%) and 3.89-fold higher than that of cell-free DNA obtained from FSN (9.83%) (FIG. 6A). These results indicated that LEP with PBS washing and DNase I treatment was helpful in enriching fetal DNA from maternal plasma samples, even in early pregnancy. In addition, such enrichment could be observed across the whole genome, even for the first trimester case (FIG. 6B). This shows that the enrichment is not biased to one or two chromosomes but instead applied to the whole genome.

B. Enriching for Long DNA Fragments

We further demonstrate that long fetal DNA fragments do exist in LEPs and corresponding reads could be obtained from LEP. We show that long DNA indeed exists in LEPs, counter to previous work. We use short read and long read sequencing techniques to show the existence of long DNA fragments in LEPs. We also show the enrichment of long DNA fragments from the fetus, e.g., the fetal fraction increases when only long DNA is analyzed. We also analyze the effect of treatment on the fetal fraction.

1. Presence of Long DNA in LEPs

To determine whether long DNA fragments exists in LEPs, we performed electrophoresis measurements. We performed such measurements with and without fragmentation of the DNA from an LEP sample. The samples were not washed or treated with a nuclease. The fragmentation helps to show whether short read sequencing can be used to analyze the resulting smaller fragments from the fragmenting of the long DNA fragments. TapeStation High Sensitivity D1000 results (TapeStation, Agilent Technologies) was used for the electrophoresis measurements.

Figure 7:
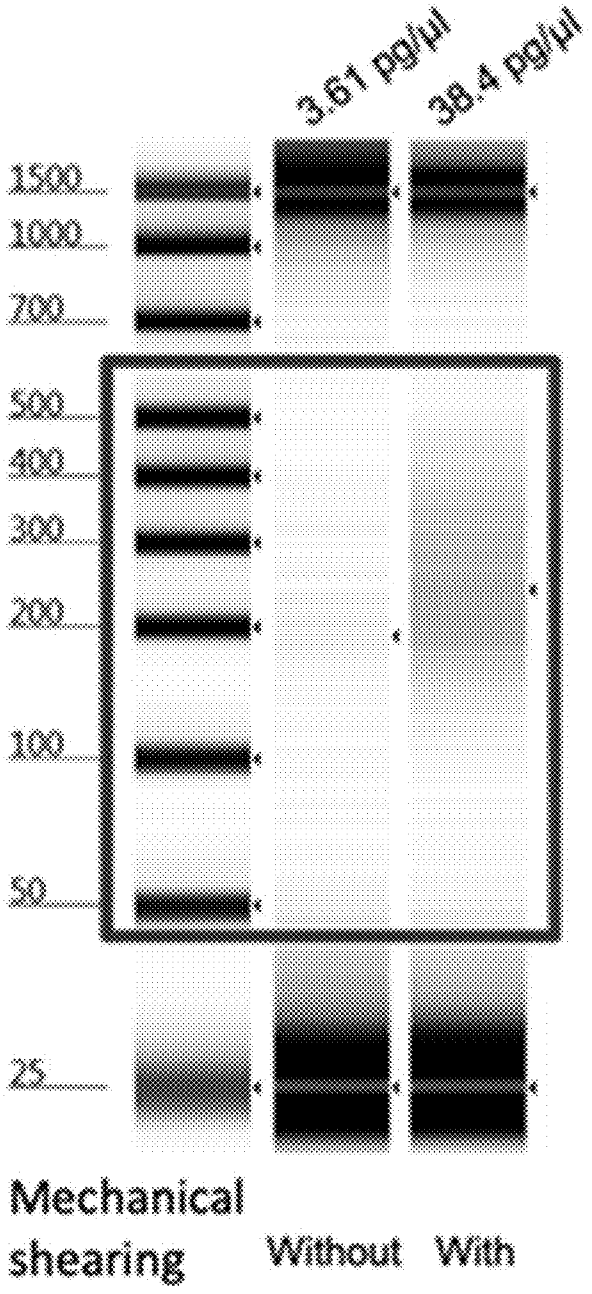
FIG. 7 shows the presence of long DNA in LEPs as revealed by mechanical shearing.

FIG. 7 shows the presence of long DNA in LEPs as revealed by mechanical shearing. The plot illustrates the TapeStation results of LEP-associated DNA with and without mechanical shearing. The DNA concentration between 50-600 bp (denoted by the rectangle) is quantified and shown at the top of each lane. The reference scale for different sizes is shown on the left.

The quantity of DNA molecules<600 bp obtained from LEPs without mechanical shearing (0.1 ng) was much smaller than that with mechanical shearing (Covaris; 1.2 ng). This result indicates that long DNA inside LEP exist and were fragmented by Covaris into a size range measurable by TapeStation HS D1000. The size range of the box (~50-600 bp) corresponds to the size range that can be sequenced using short read platforms. The fragmentation and increase of DNA fragments within this range shows that a fragmentation step can be used to sequence these unexpected long fragments, thereby increasing the amount of DNA that can be analyzed and possibly increasing the fetal fraction, as is shown later.

2. Enrichment of Long DNA in LEP

Given the existence of long DNA fragments in LEPs, we compared the amount of long DNA fragments among sample types, e.g., to see about an increase in long DNA in LEPs. To study the long DNA, fragmentation was used along with short read sequencing. Even with fragmentation was performed, the resulting DNA is around 200-400 bp, as shown in FIG. 7.

Figure 8A:
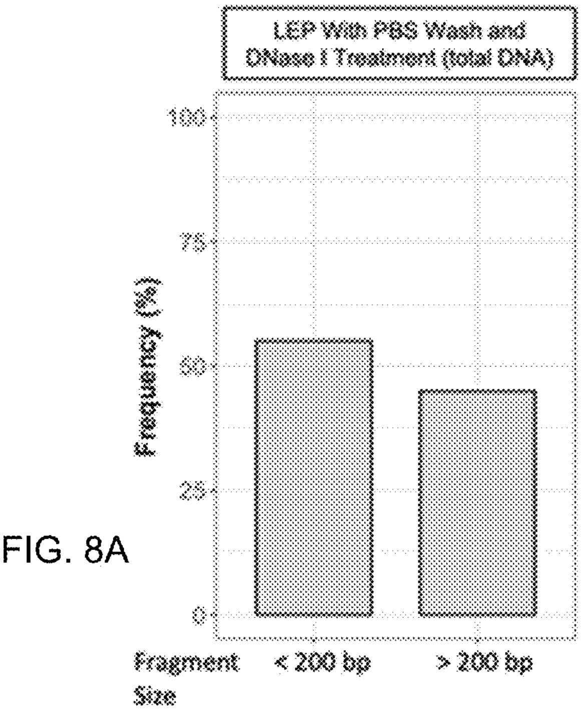
FIGS. 8A-8C show enrichment of long DNA in LEP-associated DNA.
Figure 8B:
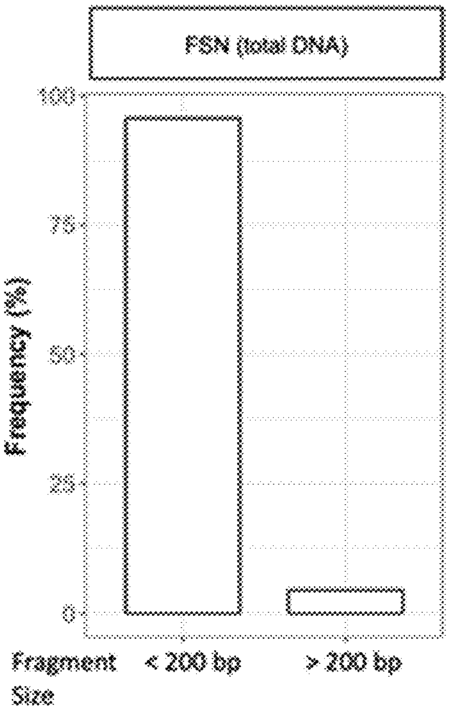
Figure 8C:
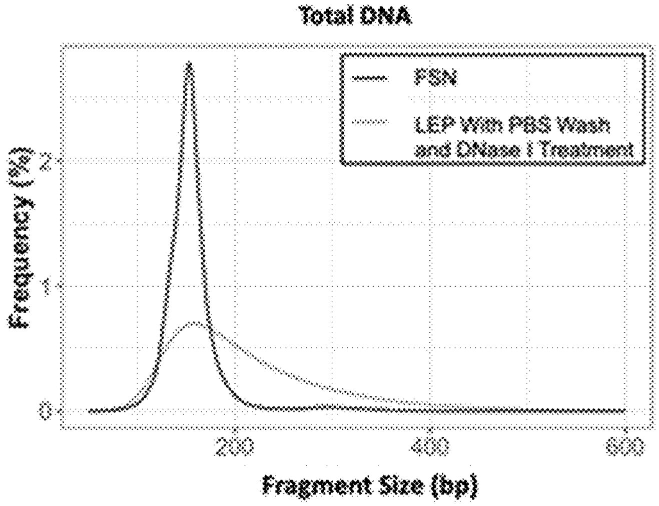

FIGS. 8A-8C show enrichment of long DNA in LEP-associated DNA. In FIGS. 8A-8B, the frequency refers to the percentage of DNA fragments in the sample that are below or above 200 bp. The two samples are FSN and LEP with PBS wash and DNase I treatment. The horizontal axis splits the data into two groups based on fragment size, namely above and below 200 bp.

The plots illustrate the enrichment of long DNA in LEP-associated DNA. For LEP wish PBS wash and DNase I digestion, 44.9% of DNA molecules were longer than 200 bp (FIG. 8A), whereas, for FSN, only 4.4% of the DNA molecules were longer than 200 bp (FIG. 8B). There is about a 10-fold increase in the percentage of long DNA molecules. Further, there is an increase in total long reads: 2,697,610 (LEP with wash and nuclease digestion) vs 410,646 (FSN). Thus, even when mechanically sheared to a target size of 200 bp, we still observed a substantial proportion of long molecules (i.e., 44.9% of DNA molecules>200 bp) in DNA obtained from LEP (Case 1), which was much higher than that of cell-free DNA obtained from the FSN (i.e., 4.4% of DNA molecules>200 bp).

FIG. 8C shows the size distribution of LEP-associated DNA and cell-free DNA from FSN. The plot shows the percentage of the DNA fragments in a sample that are at a particular size. The X-axis is fragment length, as measured in bp. The size distribution of DNA in LEP was substantially longer than that in FSN. As one can see, the FSN has a sharp peak at around 166 bp, which is typical of plasma. But the treated LEP sample has a long tail with appreciable DNA fragments up to 400 bp, and this is even after the fragmentation step. Thus, the overall size profile of LEP-associated DNA was shifted toward larger sizes relative to the cell-free DNA of FSN.

Given that fragmentation was performed, these results suggested that those DNA molecules more than 200 bp in length would be derived from even longer DNA molecules (e.g., a few kilobases).

Figure 9A:
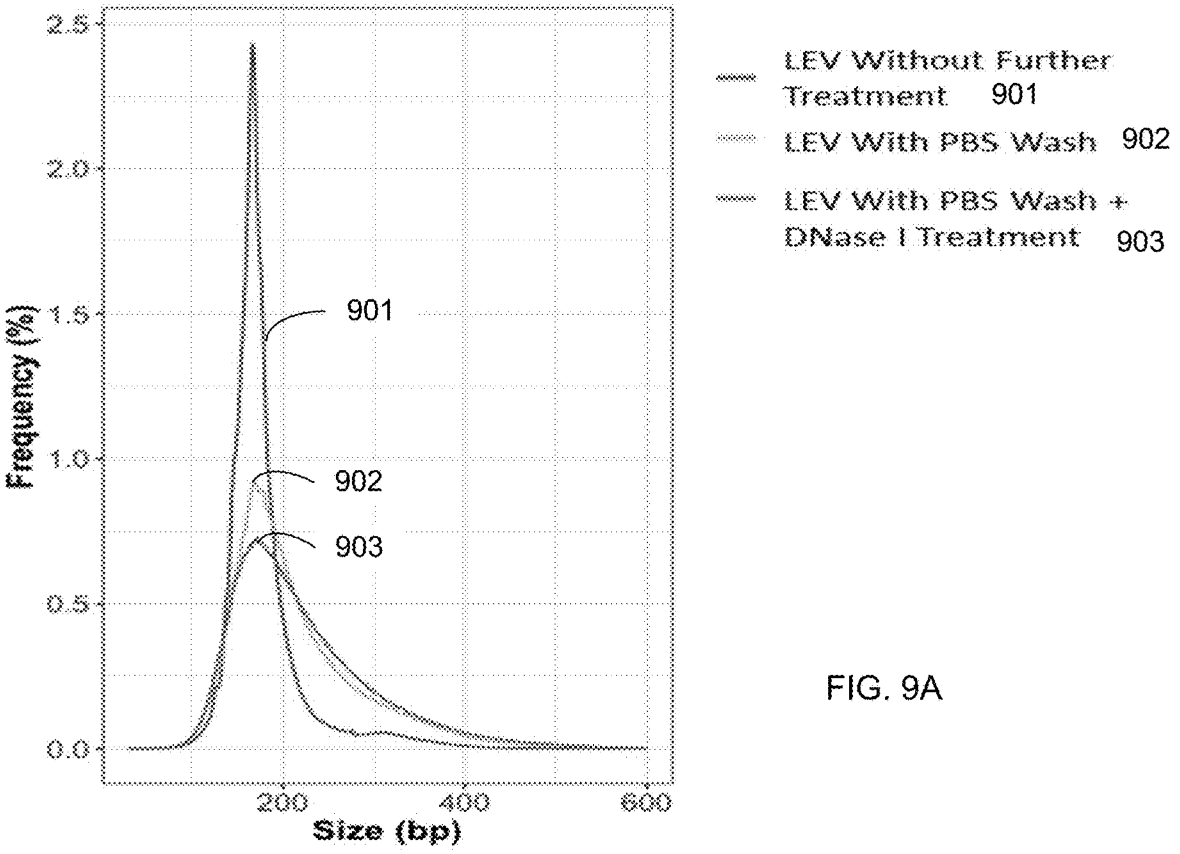
FIG. 9A shows the size profile of all DNA in various sample types corresponding to different treatments.

FIG. 9A shows the size profile of all DNA in various sample types corresponding to different treatments. The DNA was still fragmented, e.g., using mechanical shearing, light, or sonication. As shown, the size distribution 901 of DNA from LEV without further treatment remains similar to the typical distribution of plasma DNA. However, the size distribution 902 (profile) of LEV with PBS wash and the size distribution 903 of LEV with PBS wash and DNase I treatment indicated that the DNA inside of the LEPs have longer lengths on average than the untreated sample. Because DNA is fragmented to 200 bp, this size profile does not provide the natural size, which would be even longer. If a DNA fragment is shorter than 200 bp, it would not be fragmented.

Figure 9B:
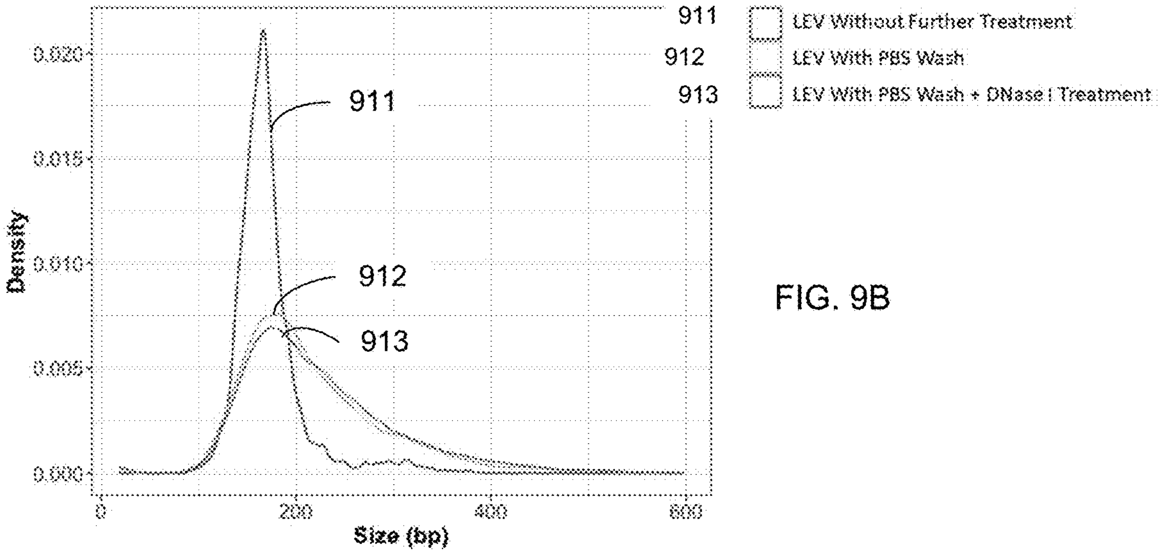
FIG. 9B shows the size profile of fetal DNA in various sample types corresponding to different treatments.

FIG. 9B shows the size profile of fetal DNA in various sample types corresponding to different treatments. Similar to the previous total nuclear DNA size distribution, the size distribution of fetal DNA showed the same trend. Without further treatment, the DNA size distribution 911 remains similar to typical plasma DNA distribution. The size distribution 912 (profile) of LEV with PBS wash and the size distribution 913 of LEV with PBS wash and DNase I treatment indicated that the DNA inside of them might have longer lengths on average than the untreated sample.

For both FIGS. 9A and 9B, many DNA fragments from the treated samples have a longer size over 200 BP. In contrast, the FSN in FIG. 8C has very few DNA fragments over 200 BP. The distribution of the LEPs (particularly treated) and the cell-free DNA is quite different because the treated LEV samples do not have a peak at 166 bp.

Instead of using fragmentation and a short-read sequencing platform, LEP-associated DNA can be sequenced with long read sequencing techniques, such as single molecule real-time sequencing (a pool of 2 third trimester pregnancy samples).

Figure 10:
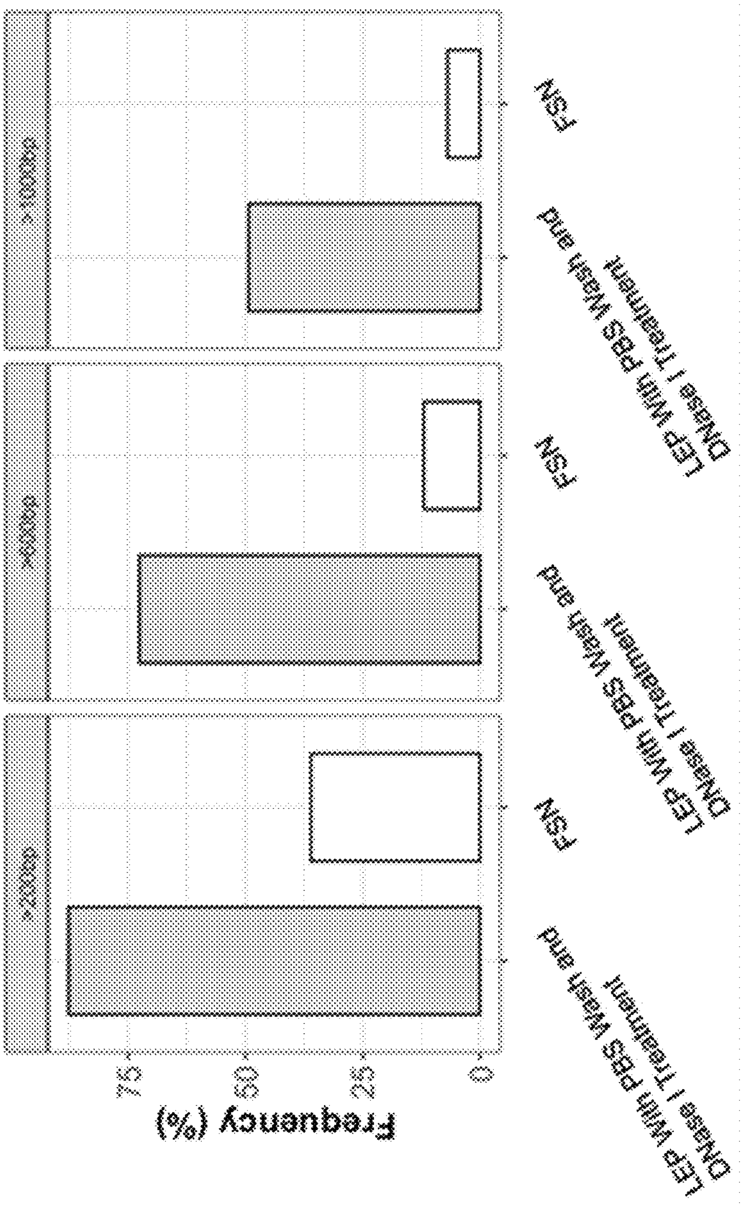
FIG. 10 illustrates how single molecule real-time sequencing reveals the enrichment of long DNA in LEP-associated DNA.

FIG. 10 illustrates how single molecule real-time sequencing reveals the enrichment of long DNA in LEP-associated DNA. The vertical axis shows the percentage of the DNA fragments in a sample that are above a certain size threshold. Three size thresholds are used: 200 bp, 600 bp, and 1000 bp. For each size threshold, two sample types were tested: FSN and LEP with wash a nuclease treatment. The LEP-associated DNA showed substantial increase of DNA molecules with a size of longer than 200 bp (87.67%), 600 bp (72.60%) and 1000 bp (49.32%) compared with cell-free DNA from FSN (percentage of cell-free DNA>200 bp: 36.05%; >600 bp: 11.93%; >1000 bp: 6.87%).

As shown in FIG. 10, the number of DNA molecules with a length of >600 bp was substantially higher in LEP-associated DNA (72.60%) compared with cell-free DNA from FSN (11.93%). This result confirmed the previous finding that a substantial proportion of DNA present in LEPs could not be sequenced directly on Illumina short-read sequencing platform. In addition, the LEP sample harbored a much higher amount of DNA molecules with a length of >1 kb (49.32%) than cell-free DNA from FSN (6.87%). These data further suggested that analyzing LEP-associated DNA according to the embodiments in this disclosure would enrich molecules of fetal origin and obtain more long DNA molecules, thus facilitating the improvement of NIPT.

The ability to obtain such a high percentage of long DNA fragments can provide various advantages. For example, the use of methylation information at CpG sites and/or variants in long DNA molecules would facilitate the determination of maternal inheritance of the fetus. One could determine whether an observed DNA fragment from LEP would be derived from the fetus (e.g., using a fetal-specific marker), thereby determining whether such DNA fragment linked genetic/epigenetic alterations, if present, would be transmitted to the fetus. In this way, the analysis of gene imprinting can be enabled using such long DNA fragments. Any use of a fetal-specific marker described herein can be performed in various ways, such as a genetic marker (e.g., a sequence allele) or an epigenetic marker (e.g., a methylation marker or a fragmentation pattern, such as an end motif or ending position.

Paramagnetic beads provides another way to analyze the length of DNA fragments. Based on solid-phase reversible immobilization technology, one could use paramagnetic beads to selectively enrich nucleic acids based on DNA molecule sizes. Such a bead comprised a polystyrene core, magnetite, and carboxylate-modified polymer coating. DNA molecules would selectively bind to beads in the presence of polyethylene glycol (PEG) and salt, depending on the concentration of PEG and salt in the reaction. PEG caused the negatively charged DNA to bind with the carboxyl groups on the bead surface, which would be collected in the presence of the magnetic field. The molecules with desired sizes were eluted from the magnetic beads using elution buffers, for example, 10 mM Tris-HCl, pH 8 buffer or water. The volumetric ratio of beads to sample would determine the sizes of DNA molecules that one could obtain. With lower beads to sample ratio, the longer molecules would be retained on the beads.

Figure 11:
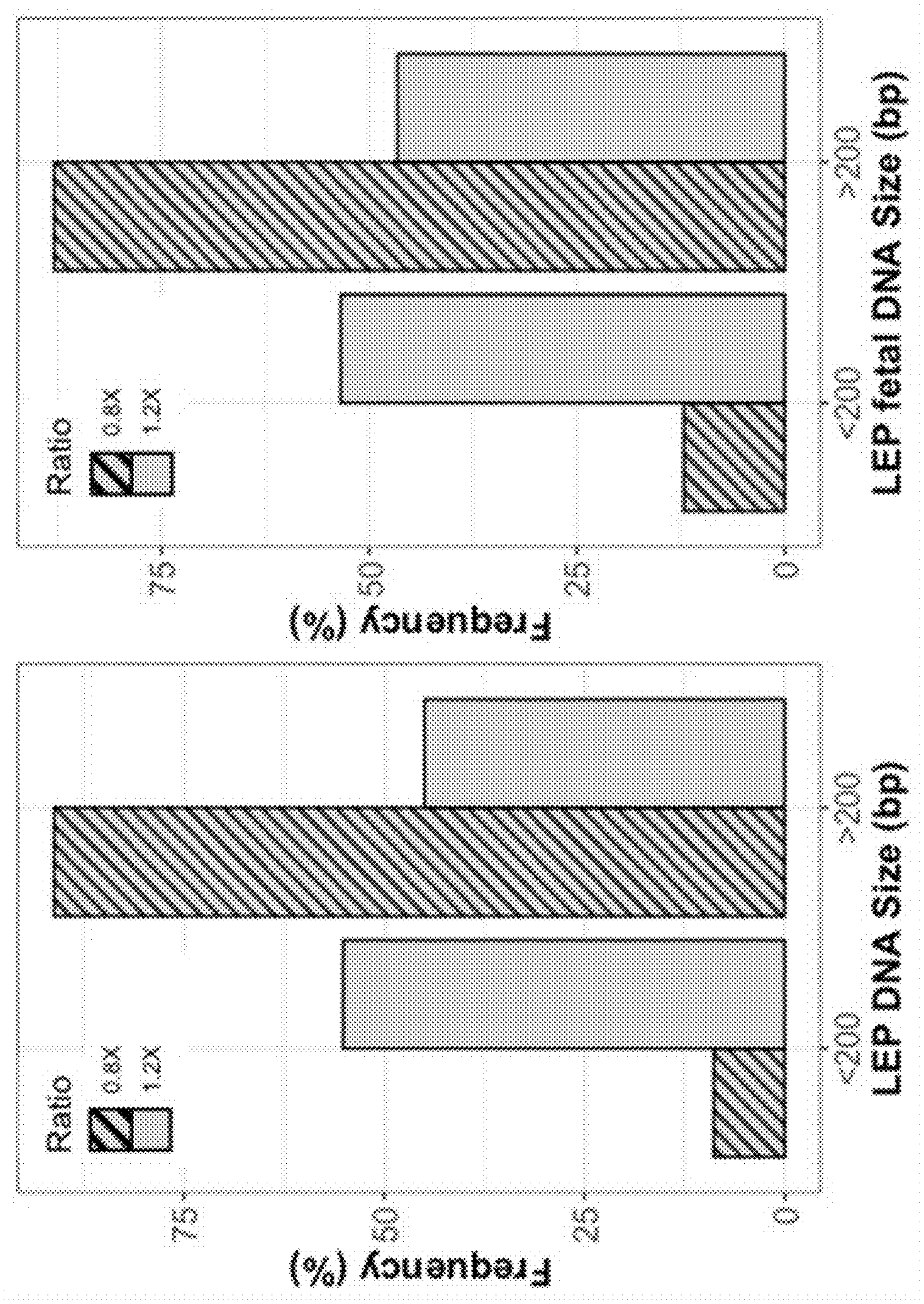
FIG. 11 shows long LEP-associated DNA could be enriched with paramagnetic beads.

FIG. 11 shows long LEP-associated DNA could be enriched with paramagnetic beads. The vertical axis shows the percentage of DNA fragments at a particular size using two different protocols 0.8× and 1.2×. The horizontal axis splits the DNA fragments into two size ranges (above and below 200 bp). The left plot is for all DNA in the sample, whereas the plot on the right is just for the fetal DNA. The fetal DNA used for the plot on the right was identified using a fetal-specific marker. The LEP samples were wash and subjected to a nuclease treatment.

As shown in FIG. 11, using a beads-to-sample ratio of 0.8× would enrich long DNA molecules in both maternal and fetal DNA population (DNA molecules>200 bp in size: 91.2%; fetal DNA molecules>200 bp in size: 87.9%), compared with using a ratio of 1.2× (DNA molecules>200 bp in size: 44.9%; fetal DNA molecules>200 bp in size: 46.6%). Accordingly, this plot illustrates the enrichment of long DNA (e.g., >200 bp) in LEP-associated total DNA (left panel) and LEP-associated fetal DNA (right panel) by using paramagnetic beads with a bead to sample ratio of 0.8×.

3. Enrichment of Long Fetal Fraction in LEP

A similar enrichment of long DNA can be found only when analyzing fetal DNA, as was showed with the paramagnetic bead data. The DNA was fragmented and subjected to short read sequencing. The fetal DNA was identified using a fetal-specific allele.

FIGS. 12A-12C shows enrichment of long fetal DNA in LEP-associated DNA. In FIGS. 12A-12B, the frequency refers to the percentage of DNA fragments in the sample that are below or above 200 bp. The two samples are FSN and LEP with PBS wash and DNase I treatment. The horizontal axis splits the data into two groups based on fragment size, namely above and below 200 bp. The fetal DNA was identified using a fetal-specific marker.

Similar to the plots when analyzing all DNA, the plots illustrate the enrichment of long fetal DNA in LEP-associated DNA. Such long DNA enrichment after the DNA shearing could also be observed in the fetal DNA population (i.e., DNA molecules>200 bp: 46.6% in LEP versus 4.3% in cell-free DNA). Again there is about a 10-fold increase in the percentage of long fetal DNA molecules. Additionally, there is an increase in the total number of long reads 2,155,708 vs 72,152.

FIG. 12C shows the size distribution of LEP-associated fetal DNA and cell-free fetal DNA from FSN. The size profile shows a similar behavior as previous other size profiles shown herein, with the LEP DNA being longer. The overall size profile of LEP-associated fetal DNA was relatively shifted toward the larger sizes relative to fetal cell-free DNA of FSN).

4. Effect of Treatment on Fetal Fraction for Long DNA Fragments

We also analyzed the effect of LEP purification and treatment steps on the fetal fraction for DNA fragments of different sizes, including above a size threshold (e.g., 200 bp, 600 bp, or 1000 bp). The fetal fraction stays steady for the LEP treated samples, with a significant increase in the fetal fraction for the LEP sample that is treated and washed. Thus, the long DNA fragments can be obtained without a corresponding decrease in the fetal fraction, as has been observed in a standard plasma sample.

Figure 13:
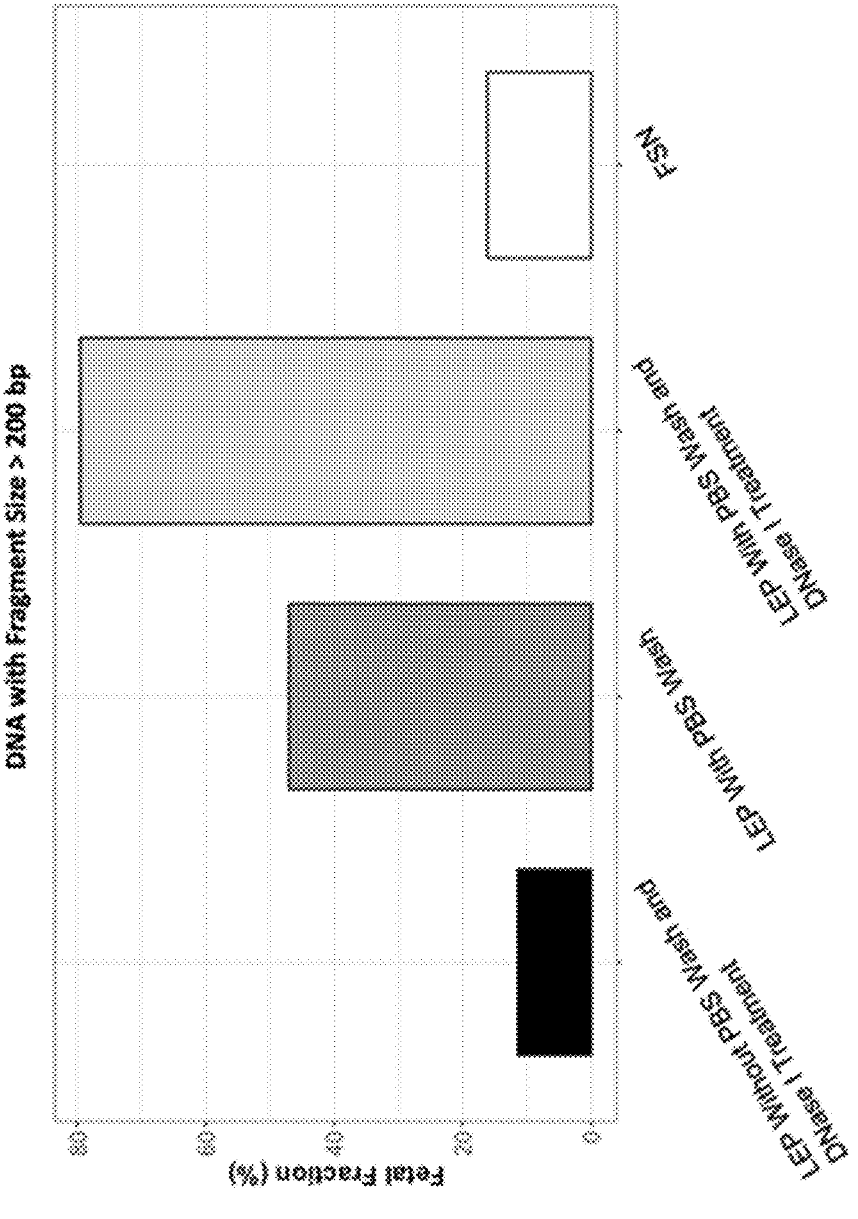
FIG. 13 shows fetal fraction in LEP with various treatments compared to FSN.

FIG. 13 shows a fetal fraction in LEP with various treatments compared to FSN. The results correspond to case 1 in FIG. 5A. The vertical axis is the fetal fraction as determined using a fetal-specific marker. The plot shows the fetal DNA fractions for those DNA molecules above 200 bp among LEP without PBS wash and DNase I treatment, LEP with PBS wash, LEP with PBS wash and DNase treatment, and cell-free DNA obtained from the FSN.

As shown in FIG. 13, the fetal DNA fraction in DNA molecules>200 bp obtained from LEP with only wash and with wash/treatment was higher than that in cell-free DNA obtained from the FSN. For the LEP sample with wash and treatment, the fetal fraction is near 80%. Thus, LEP-based analysis would facilitate the enrichment for those long DNA molecules of fetal origin.

Figure 14:
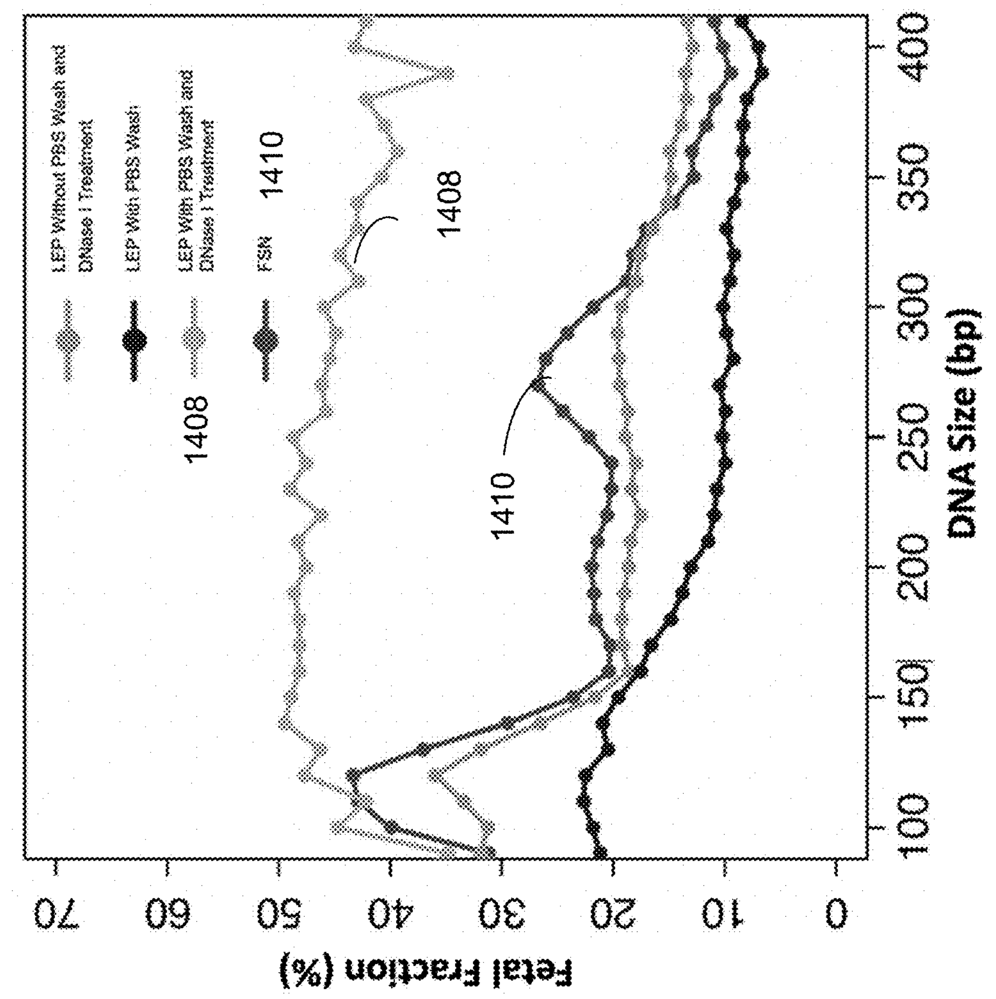
FIG. 14 shows the fetal fraction vs. fragment size for various sample types.

FIG. 14 shows the fetal fraction vs. fragment size for various sample types. The analysis used a pool of six 3rd trimester pregnancy cases. After fragmentation, the sequencing was performed on a short-read sequencing platform. The vertical axis is the fetal fraction, and the horizontal axis is the fragment size. The fetal fraction was determined using one or more fetal-specific markers at a set of one or more loci. A fragment is used in the determination if the fragment covers one of the loci corresponding to a fetal-specific marker. The fetal fraction is determined using a ratio of a number of fragments having a fetal-specific marker and the total number of fragments covering any one of the loci.

As one can see, the fetal DNA fraction in the DNA pool from washed-treated LEV sample 1408 appeared to be relatively steady, as the size of DNA fragments increased. In contrast, the fetal DNA fraction in the DNA pools from FSN sample 1410 (deemed to be equivalent to plasma) was dramatically reduced as the size of DNA fragments increased. These results indicate that embodiments can obtain more long fetal DNA with DNA from LEV with DNase treatment.

The combined ability to have high fetal fraction among long DNA fragments provides various advantages, e.g., allowing for more efficient techniques to determine genomic characteristics of the fetus. For example, with the fetal fraction near 50%, the fetal-specific alleles will comprise a significant proportion of the DNA fragments. The fetus would not need to be genotyped, e.g., as sequencing errors can be easily filtered out. Sequencing errors would be far fewer than the actual fetal-specific allele. Thus, if the number of rDNA fragment at a locus is at least 10-15% of the fragment at a given locus, then that allele (which is different from the maternal allele) can be identified as fetal-specific allele. And with long DNA fragments available, such a fetal-identified fragment has a higher likelihood to cover a CpG site, thereby enabling the detection of fetal epigenetic properties. Additionally, such long DNA fragments would have a higher likelihood of including multiple fetal-specific alleles, thereby allowing a determination of a fetal haplotype by stitching together fragments that have the fetal-specific allele. Similarly, for the long fetal DNA fragments, it is more likely that multiple fetal-specific epigenetic markers exist in a same fragment, thereby allowing fetal DNA to be identified and stitched together to identify both haplotypes.

C. SEPs

We also analyzed an SEP sample prepared in a manner described for FIGS. 1 and 2. The SEP would roughly have a size less than 200 nm. The analysis looked at the proportion of DNA fragments at different sizes for plasma and SEP sample, as well as the fetal fraction for these two sample types. We show that long fetal DNA molecules could be obtained through analysis of SEP-associated DNA.

To analyze long size DNA from SEP source, a pool of 5 SEP-associated DNA samples from third-trimester pregnant women and the paired untreated plasma DNA sample were subjected to single molecule real-time sequencing (Pacific Biosciences) with 0.87 million and 0.98 million circular consensus sequences (CCSs) generated, respectively. The length of fetal DNA molecules obtained from SEP (SEP-DNA) ranged from 50 bp to 23,026 bp.

Figure 15:
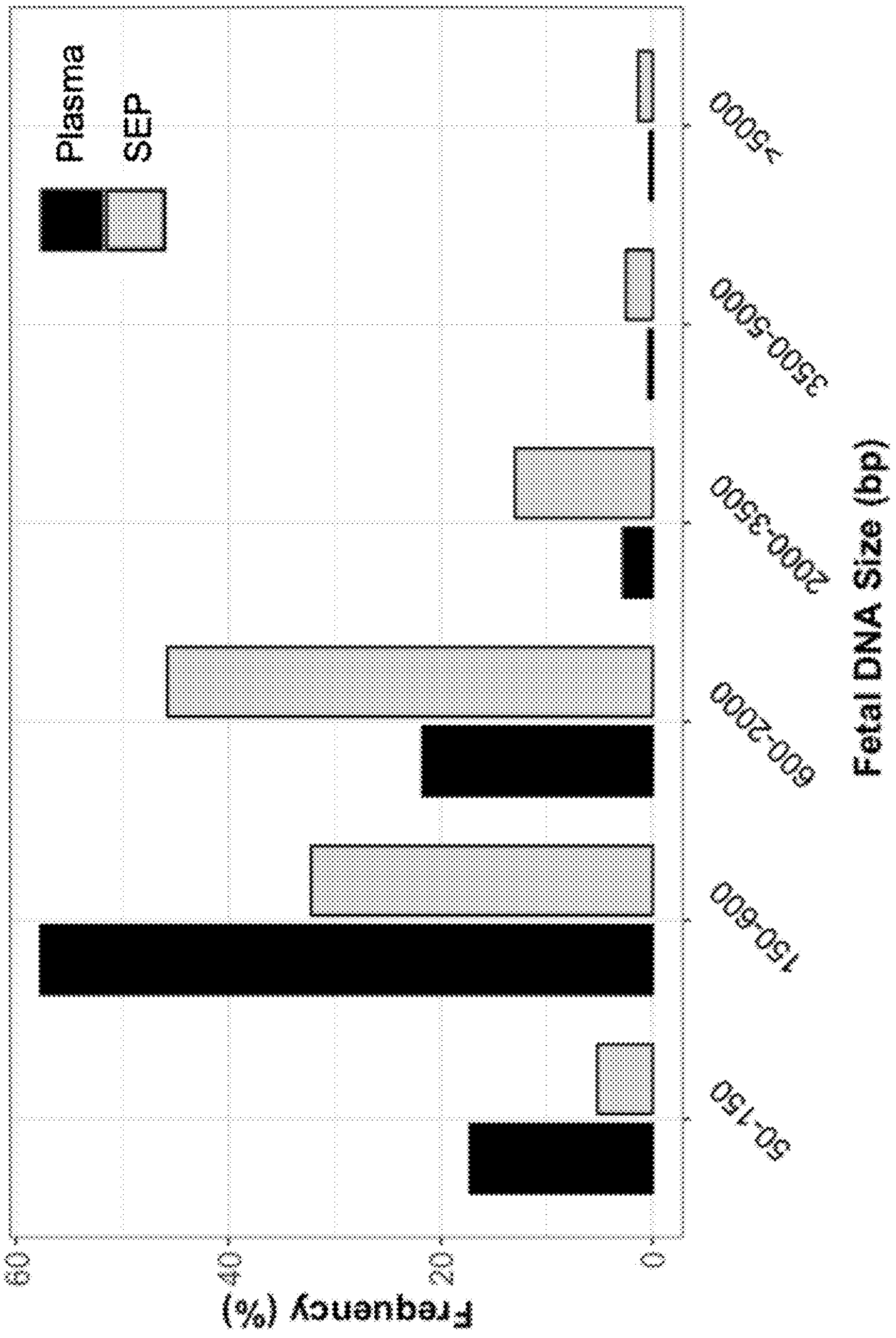
FIG. 15 shows size distributions of SEP-associated DNA and paired plasma DNA.

FIG. 15 shows size distributions of SEP-associated DNA and paired plasma DNA. The vertical axis is the percentage of the DNA fragment that occur within a given size range for each of the two sample (SEP and plasma).

FIG. 15 shows an increase in the long DNA fragments for the SEP sample. The size distribution of SEP-associated fetal DNA molecules was shifted toward the larger size, suggesting that SEP-associated fetal DNA enriched for long fetal DNA molecules. For example, DNA molecules>200 bp account for 86.9% and 56.3% of SEP-associated fetal DNA and plasma fetal DNA, respectively. The percentage of DNA fragments within a size range of 2,000 to 3,500 bp in SEP-associated fetal DNA (13.0%) was 4.6 times higher than that of plasma fetal DNA (2.8%).

Compared to plasma, the peak in the size distribution is switched from the main peak at around 150-600 bp to the size range of 600-2000 bp. This shows that long fragments are also enriched in the SEP sample relative to plasma. Importantly, the single molecule sequencing technique was able to detect these long fragments, which had been missed in previous studies.

Figure 16B:
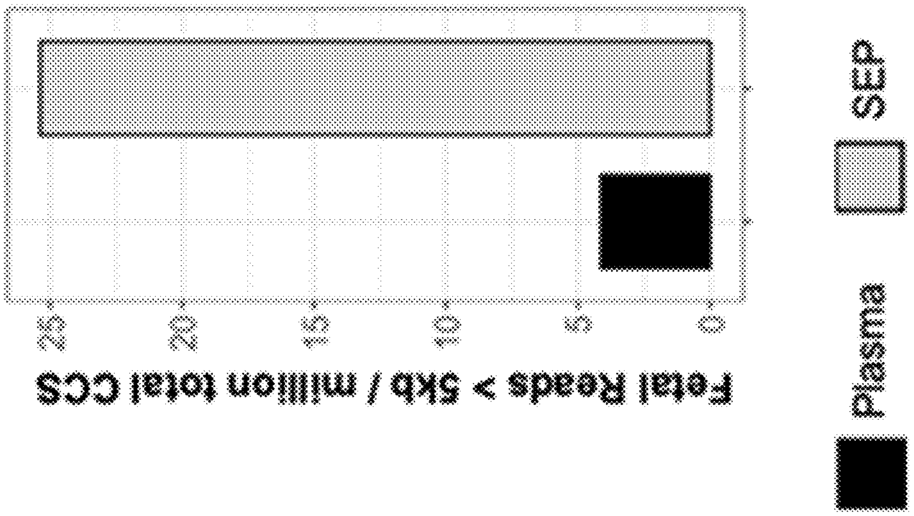
FIGS. 16A-16B show analysis of fetal DNA molecules in SEP-associated DNA using different size ranges.
Figure 16A:
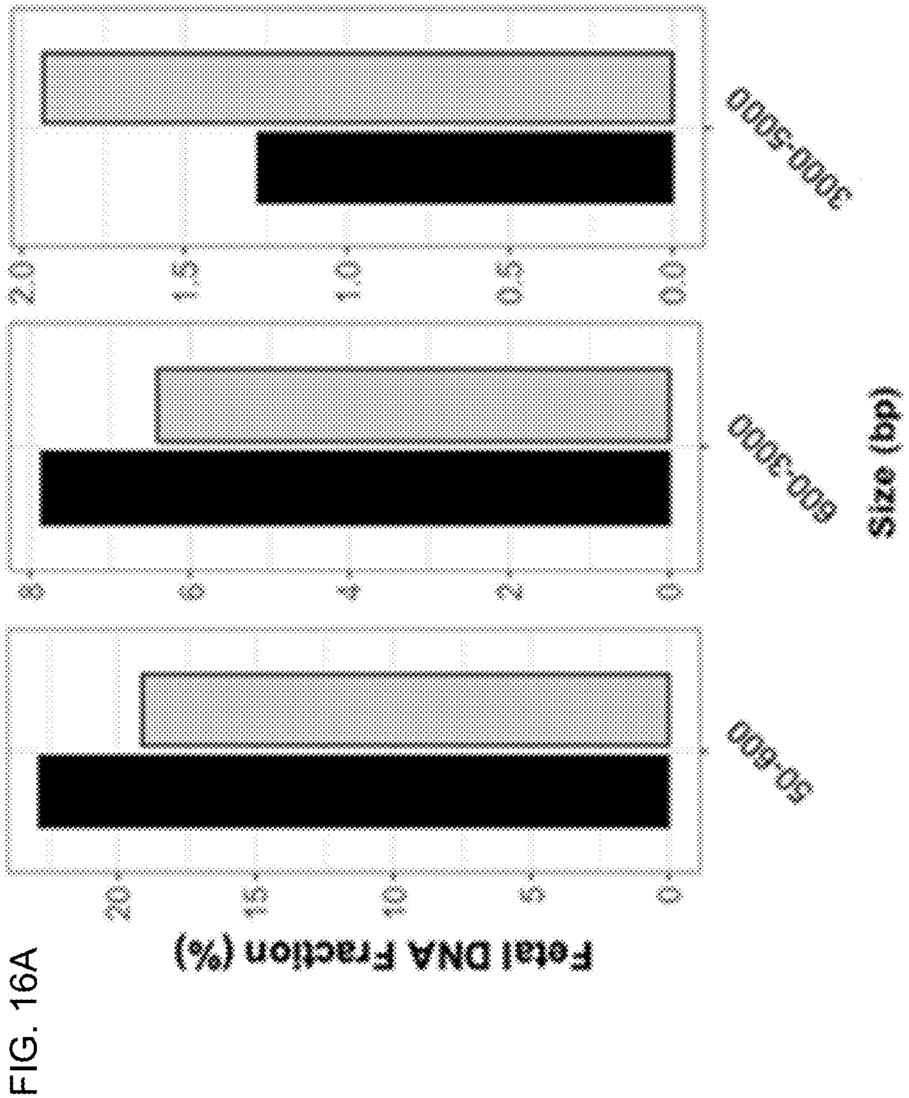

FIGS. 16A-16B shows analysis of fetal DNA molecules in SEP-associated DNA using different size ranges. FIG. 16A shows the fetal DNA fractions across different DNA size ranges for plasma and SEP samples. In FIG. 16A, the vertical axis is the fetal DNA fraction as measured using a fetal-specific marker. The horizontal axis shows three size ranges, each of which shows a fetal fraction for the plasma and SEP sample.

We envisioned that the fetal DNA fraction would be varied according to the different sizes in DNA molecules obtained from SEP. Indeed, in the smaller size ranges (50-600 bp and 600-3000 bp), the fetal fraction is a lower in the SEP sample than the plasma. But for the DNA in the 3000-5000 range, the fetal fraction is higher in the SEP compared to the plasma. Thus, for very long DNA, the decreasing of the fetal fraction in the plasma DNA is much dramatic than the SEP. Accordingly, for long DNA, the SEP can provide more fetal DNA and longer fetal DNA than plasma.

More specifically, in a fragment size range of 3,000 to 5,000 bp, the fetal DNA fraction was higher in SEP associated DNA than plasma DNA (1.9% versus 1.2%). In contrast, the fetal DNA fraction was lower in SEP associated DNA than plasma DNA for both fragment size ranges of 50 to 600 bp (19.1% versus 22.9%) and 600 to 3,000 bp 6.4% versus 7.8%).

FIG. 16B shows the amount of fetal DNA fragments with size>5 kb per million total CCSs from SEP-associated DNA and plasma DNA. A CCS can be considered equivalent to a DNA fragment. Such enrichment seen for fragments in 3000-5000 bp can be extended to DNA fragments with a size of >5 kb, in which the number of fetal DNA fragments with size>5 kb is was surprisingly times higher in the SEP-associated DNA compared with the paired plasma DNA. In plasma, there is less than five reads, but the SEP has about 25 reads, which is at least five times more. Long fetal DNA molecules were thus enriched in the SEP-associated DNA relative to plasma. This analysis of SEPs was different from the previous study by Zhang et al. in which the short-read sequencing was used, thus being only able to detect DNA molecules below 600 bp (Zhang et al. BMC Med Genomics. 2019; 12:151).

These data suggested that in some embodiments, one was also able to enrich long fetal DNA using SEP-associated DNA with fragment size selection. Fragment size selection could be performed in silico or physically (e.g., gel-based or bead-based DNA size selection).

V. Fetal Analysis

Various types of analyses can be performed using the DNA extracted from the particles, e.g., after purification of LEPs or SEPs and then disruption of the membranes to expose the DNA fragments. The DNA fragments can be analyzed using various assays, such as various types of sequencing and PCR, as described herein. Such assays can provide information about the DNA fragments, such as sequence (including end motifs), location in a reference genome of (e.g., after alignment, and including genomic positions of the ends of the DNA fragments), methylation statuses at various sites (e.g., CpG sites), and size (e.g., from length of entire sequence or determined from aligned of sequence at ends, as may be done from paired-end reads). Such information can provide properties at certain positions, sites, or regions, such as counts, size of DNA fragments, methylation level(s), ending positions in a genome, amount of overhand (jaggedness) at ends of a fragment, and motifs at the end of fragments, e.g., 3-mers or 4-mers at the end of the DNA fragments.

Various examples of bioinformatic analysis has already been discussed. For example, copy number aberrations (or other sequence imbalances) can be detected based on a count of DNA fragments at one region or haplotype can be compared to a reference value, such as a count of DNA fragments at a different region or on the other haplotype. Methylation levels or sizes and differences among regions/haplotypes can also be used. Additional examples are provided below.

A. Maternal Inheritance of the Fetus

The higher fetal DNA fraction present in LEP-associated DNA would improve the resolution and accuracy of the maternal inheritance analysis of the fetus. For example, one could use relative haplotype dosage (RHDO) analysis based on the sequential probability ratio test (SPRT) (Lo et al. Sci Transl Med. 2010; 2:61ra91 and U.S. Publication No. 2011/0105353) to deduce the maternal inheritance of the fetus, using sequencing results from LEP-associated DNA. Methylation haplotypes can also be used, as described in U.S. Publication No. 2017/0029900. As other examples besides SPRT, one could use RHDO analysis based on, but not limited to, binomial distribution, Poisson distribution, gamma distribution, beta distribution, Hidden Markov Model, etc.

The RHDO method can use the differences in allelic counts of heterozygous loci (e.g., SNPs) between the maternal haplotypes in the sample, namely, Hap I and Hap II, respectively. If the maternal Hap I is inherited by the fetus, the number of plasma DNA molecules originating from the maternal Hap I would be relatively over-represented compared with the maternal Hap II. Otherwise, the maternal Hap II would be relatively over-represented. NhapI and NhapII are the measured allelic counts of Hap I and Hap II, respectively, which can be assumed to follow the Poisson distributions.

$$N_{hapI} \sim \text{Poisson}(\lambda_1)$$

$$N_{hapII} \sim \text{Poisson}(\lambda_2)$$

Let f be the fetal DNA fraction, N be the total accumulated DNA fragments from Hap I and Hap II, and $\lambda_1$ and $\lambda_2$ be parameters based on the fetal DNA fraction and total DNA fragments. If the fetus inherits the maternal Hap I, $\lambda_1$ will be N*(0.5+f/2), and $\lambda_2$ will be N*(0.5−f/2) for those SNPs sites where the mother is heterozygous and the fetus is homozygous. When the fetal DNA fraction is higher, there will be more separation in the parameters $\lambda_1$ and $\lambda_2$, resulting in a larger separation in NhapI and NhapII, thereby allowing a classification using fewer heterozygous loci.

The difference in allelic counts between the maternal haplotypes, $N_{hapI}-N_{hapII}$, can approximately follow the normal distribution with the mean of N*f and the standard deviation of $\sqrt{N}$. The degree of the allelic count differences between the maternal Hap I and Hap II could be measured by z-score (Z):

$$Z = \frac{N_{Hap\,I} - N_{Hap\,II}}{\sqrt{N}}.$$

If Z is above 3, it will suggest the fetal inheritance of Hap I; if Z is below −3, it will suggest the fetal inheritance of Hap II. Other classification parameters (separation values) can be used, such as a ratio of NhapI and NhapII or more complex function involving a difference or ratio.

The fetus can inherit either haplotype I or II from the mother. Therefore, when Z is <3 but >−3, it would mean that there is inadequate statistical evidence to decide the fetal inheritance of that region. RHDO process could start from any genomic location, progressively accumulating the sequenced reads mapping to the SNPs present along with the maternal Hap I and Hap II, respectively. Once the classification of the maternal inheritance has been made during the accumulation of sequenced reads for RHDO analysis, the RHDO process can restart on the following heterozygous locus.

We applied RHDO analysis to 3 samples (i.e., DNA from FSN, LEP with PBS wash, and LEP with PBS wash and DNase I treatment) across the whole genome. We analyzed a median of 129,199 SNPs for which the maternal genotypes are heterozygous (range: 107,550-136,642), using 29 million sequenced results for each sample.

We obtained 678, 1033, and 1727 RHDO classifications for the sequencing results obtained from FSN, LEP with PBS wash, and LEP with PBS wash and DNase I treatment, respectively. There are more classifications for the LEP with PBS wash and DNase I treatment, and thus a higher resolution.

Figure 17A:
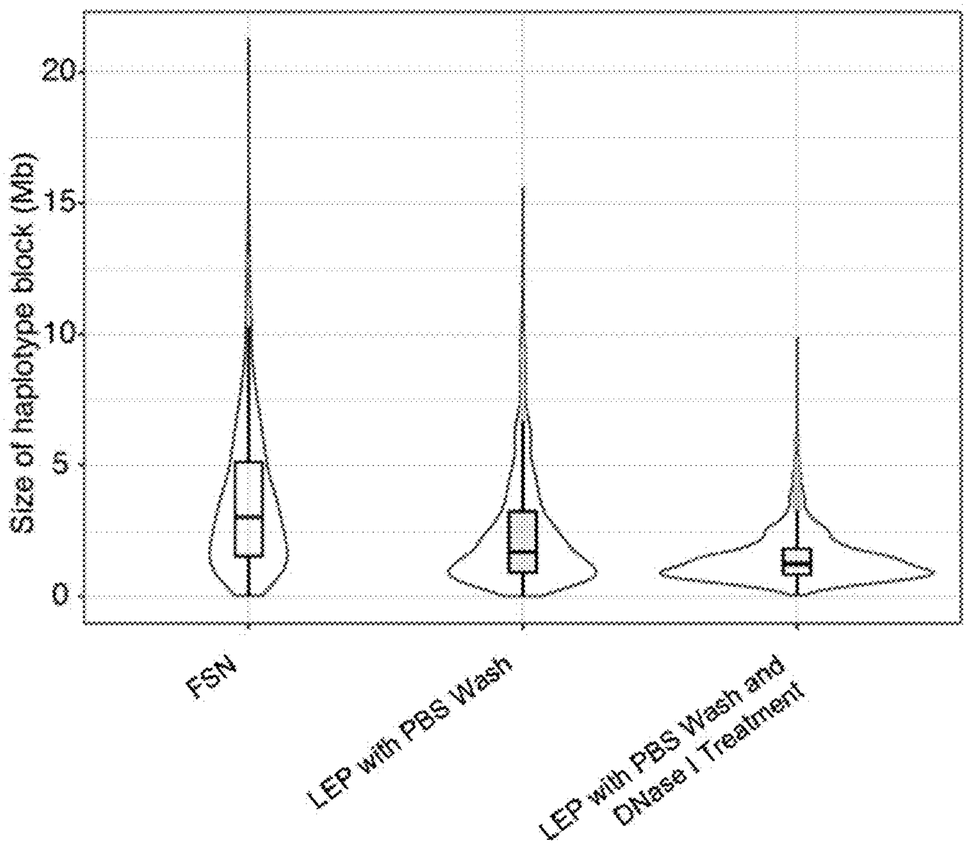
FIGS. 17A-17B show the analysis of LEP-associated DNA allowing for higher resolution of maternal inheritance determination.
Figure 17B:
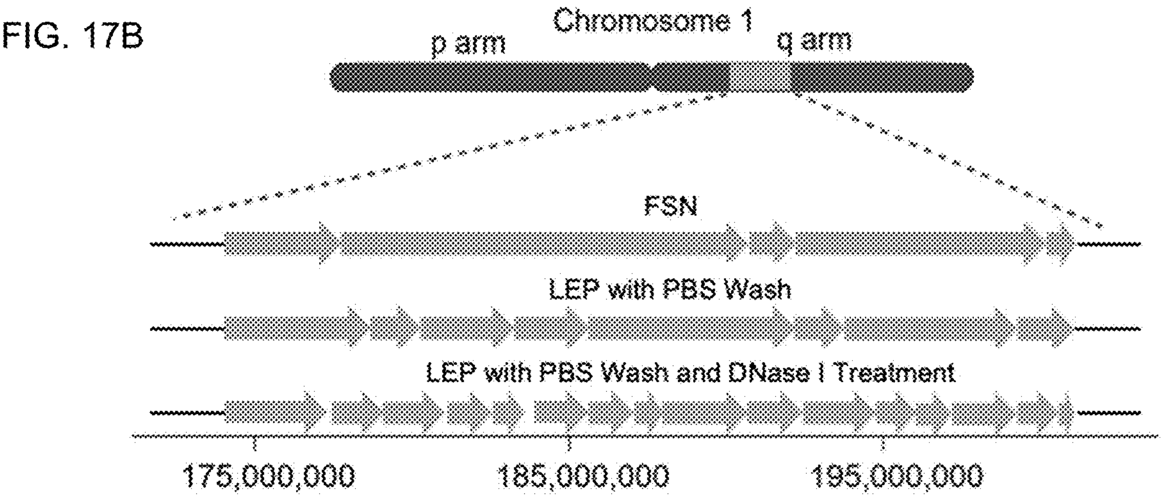

FIGS. 17A-17B shows the analysis of LEP-associated DNA allowing for higher resolution of maternal inheritance determination. FIG. 17A shows the haplotype block size distributions determined to be inherited by the fetus from the analysis of cell-free DNA (FSN), DNA from LEP with PBS wash and DNA from LEP with PBS wash and DNase I treatment, respectively. The vertical axis is the size of the haplotype block size, where the width of the lines shows more blocks at that size. FIG. 17B shows an example genomic region with maternal inheritance patterns from the analysis of cell-free DNA (FSN), DNA from LEP with PBS wash, and DNA from LEP with PBS wash and DNase I treatment, respectively.

As shown in the violin plots of FIG. 17A, the median maternal haplotype block size determined to be inherited by the fetus is significantly smaller in LEP with PBS wash and DNase I treatment (1.24 Mb), in comparison with FSN (3.03 Mb) and LEP with PBS wash (1.70 Mb). This result suggested that LEP-associated DNA enabled us to achieve higher resolution in determining the maternal inheritance of the fetus. The same conclusion was reached using N50 statistic (i.e., FSN: 5.26 Mb; LEP with PBS wash: 3.78 Mb, LEP with PBS wash and DNase I treatment: 1.73 Mb). N50 is defined as the length corresponding to the haplotype block at which the cumulative length of haplotype blocks reaches 50% of the total length of all blocks after ranking all haplotype blocks by their length in descending order.

FIG. 17B shows an example genomic region (chr1: 174,000,000-200,000,000) exhibiting a number of the maternal haplotype blocks determined to be inherited by the fetus by analyzing DNA sequencing data from FSN, LEP with PBS wash, and LEP with PBS wash and DNase I treatment, respectively, according to the embodiments in this disclosure. One can observe that the maternal inheritance of the fetus could be achieved in higher resolution in LEP-associated DNA.

Therefore, these results suggested that the analysis of LEP-associated DNA would enable better performance in detecting monogenic disorders in a non-invasive manner. For example, the high resolution of the RHDO analysis in FIG. 17B can enable pinpointing the recombination of the fetus if it is present. The recombination present in the fetus would confound the RHDO analysis with a low resolution RHDO analysis (i.e., using FSN). For example, a 100-Mb region would have a higher chance to contain a recombination than a 1 Mb region. Thus, the 100-Mb resolution RHDO analysis concludes maternal haplotype I with 100 Mb in size passed onto the fetus. But actually, there is a recombination within from 90 Mb to 100 Mb that harbors the disease-causing gene. Hence, a wrong interpretation for which the fetus is affected by the disease would occur.

On the other hand, if the 1 Mb resolution RHDO analysis (e.g., LEP with wash and nuclease treatment), one could see that there many blocks before the 90 Mb location that will be classified as Hap I passing onto the fetus, followed by a pattern where many blocks after 90 Mb location will be classified as Hap II passing onto the fetus. In this manner, we could achieve the correct interpretation as to whether the fetus is affected. The use of LEP DNA would enable the high resolution of RHDO analysis, thus improving the performance of the monogenetic disorder detection.

Haplotype inheritance and monogenic disorders are examples of genomic characteristics of the fetus. Other genomic characteristics of the fetus can be determined, such as a sequence imbalance, a genotype (e.g., an inherited allele), a haplotype (e.g., an inherited haplotype), a mutation (e.g., a mutated allele), and a methylation level.

B. Pregnancy Analysis

Besides genomic characteristics of the fetus, a genomic characteristic of a pregnancy can be determined. The diagnostic values of particle-associated DNA could be extended to pregnancy complications (e.g., preeclampsia). Increased plasma EPs were reported in preeclampsia patients (Orozco et al. Placenta. 2009; 30:10; Goswami et al. Placenta. 2006; 27:1), indicating that the EP-associated DNA level might be a promising biomarker for those diseases. Thus, DNA molecules obtained from LEP, SEP, and FSN could be used to inform the pregnancy complications, including but not limited to high blood pressure, gestational diabetes, infections, preeclampsia, preterm labour, pregnancy loss/miscarriage, fetal growth restriction (FGR). Subjects with preeclampsia can have lesser amounts of long cfDNA.

Additionally, methods can distinguish between RNA molecules contributed by the mother and fetus in an EP sample. The methods can thus identify changes in the contribution from one individual (i.e., the mother or fetus) to the mixture at a particular locus or for a particular gene, even if the contribution from the other individual does not change or moves in the opposite direction. Such changes cannot be easily detected when measuring the overall expression level of the gene without regard to the tissue or individual of origin.

C. Benefits of High Fetal Fraction

The ability to have high fetal fraction among DNA fragments provides various advantages, e.g., allowing for more efficient techniques to determine genomic characteristics of the fetus. For example, with the fetal fraction near 50%, the fetal-specific alleles will comprise a significant proportion (e.g., at least 10%, 15%, or 20%) of the DNA fragments. For example, when the fetal fraction is 50%, a fetal-specific allele at a heterozygous locus of the fetus would comprise about 25% of the DNA fragments.

As a result of the high fetal fraction, fetal cells would not need to be genotyped, e.g., as sequencing errors can be easily filtered out since they would occur at a much lower rate. Sequencing errors would be far fewer than the actual fetal-specific allele. Thus, if the number of DNA fragments at a locus is at least above a threshold (e.g., 10%, 15%, or 20%) of the fragment at a given locus, then that allele (which is different from the maternal allele) can be identified as a fetal-specific allele. Such genotyping of the fetus using a purified blood sample from the mother can provide information about fetal mutations, including de novo mutations since the significant portion of fragments with the mutation would exist.

Besides improved functionality, increased accuracy and efficiency (e.g., smaller sample or fewer assays reactions and/or reagents) can be used. For example, since there would be more fetal DNA fragments in a sample (e.g., after purification for LEPs and/or fragment size selection for LEPs or SEPs), there would be greater separation between two classifications of a genomic characteristics of the fetus. For instance, there would be greater separation between the two classifications of a sequence imbalance (e.g., indicating a copy number aberration) since the overrepresentation or underrepresentation would be larger.

Since the overrepresentation or underrepresentation would be larger, a threshold (cutoff) for making the classification would be reached sooner, i.e., with fewer DNA fragments. Thus, a smaller sample and/or less assay reactions (e.g., less sequencing or digital PCR) can be performed. Accordingly, the higher concentration of DNA molecules originating from the placenta can lead to a higher sensitivity approach in detecting the fetal abnormalities, including but not limited to the detection of chromosomal aneuploidies (e.g., trisomy 21, 18 or 13), and single-gene disorders (e.g., cystic fibrosis, hemochromatosis, Tay-Sachs, beta-/alpha-thalassemia, and sickle cell anemia).

D. Benefits of Using Long DNA

Surprisingly, the data herein shows an increase in long DNA fragments. This is contrast to previous work by Zhang et al., which found shorter and fewer DNA fragments. The techniques described herein provide for a preferential enrichment for LEPs, e.g., by using the pellet of large particles obtained after centrifuging at more than 10,000 g for at least 10 min. Further, the use of long read sequencing techniques (such as nanopore sequencing (e.g., Oxford Nanopore Technologies) and single-molecule real-time sequencing (e.g., Pacific Biosciences)) or fragmentation with short read sequencing techniques can provide sequence reads of the long DNA fragments.

1. Haplotype and Mutation Analysis

There are also benefits from having a higher amount (e.g., raw amount or percentage) of long DNA fragments in a sample (e.g., after purification for LEPs). In addition to RHDO analysis with the benefit of obtaining higher feta DNA fraction in LEV, the genetic and epigenetic analysis of long DNA fragments in LEV and SEV can be performed. For example, the use of methylation information at CpG sites and/or variants in long DNA molecules would facilitate the determination of maternal inheritance of the fetus. One could determine whether an observed DNA fragment from LEP would be derived from the fetus (e.g., using a fetal-specific allele, which can be identified via the techniques described above), thereby determining whether such DNA fragment linked genetic/epigenetic alterations, if present, would be transmitted to the fetus.

With long DNA fragments (e.g., 500 bp, 600 bp, 700 bp, 800 bp, 900 bp, 1000 bp, 5000 bp or longer), it is more likely to have both a SNP site and a CpG site together on the same fragment, or multiple SNP sites, or multiple CpG sites on the same fragment. The allele status and/or the methylation status at such positions can provide increase ability and accuracy for determining a haplotype. The multiple values (allele or methylation status) on a same fragment can be compared to parental haplotypes or other reference haplotypes (e.g., from a certain population). In this manner, a haplotype can be identified.

The longer DNA fragments can also help with de novo assembly, e.g., for determining a haplotype and/or de novo mutations. With a higher likelihood of multiple heterozygous loci (for allele with same sequence or for methylation status), there is an increased change of such fragments overlapping on one heterozygous locus. Such fragments can thus extend a haplotype, e.g., by identifying an identical allele on a fragment but where the fragment also extends to another heterozygous locus to which another overlapping fragments can be identified, and so on. Additionally, fetal vesicles can be identified (e.g., using fetal-specific proteins on the outside of the vesicles), and any of such DNA fragments (short or long) can be linked together or fill in gaps from haplotyping focused on the long DNA fragments.

There is also a benefit from having a higher amount (e.g., raw amount or percentage) of long DNA fragments in a sample that are fetal (e.g., after fragment size selection for LEPs or SEPs). For example, one can essentially determine three haplotypes for each region, i.e., two from the mother (one of which is shared with the fetus) and one that is paternal. And when de novo mutations exist, all four haplotypes can be determined. When the fetal DNA fraction is high, each branch (haplotyped) would have sufficient numbers of DNA fragments to support (determine) each haplotype. Or when the fetal DNA fraction is so high (e.g., above 70%), the two fetal haplotypes can be determined with confidence by determining just the two most prevalent haplotypes. Further, the haplotypes can be of higher resolution with the higher fetal DNA fraction, as shown in FIG. 17B.

2. Tissue of Origin Analysis

As a further illustration of the benefits of obtaining and analyzing long DNA fragments, the longer a DNA molecule is, the larger number of CpG sites it would likely contain. Different cell types carry different methylation patterns across CpG sites; for example, cells from placental tissues possess unique methylomic patterns compared with white blood cells and cells from tissues such as, but not limited to, the liver, lungs, esophagus, heart, pancreas, colon, small intestines, adipose tissues, adrenal glands, brain, etc.

The methylation patterns could serve as 'molecular barcode' for tracing the cell identity of a DNA molecule originating from LEPs in pregnant women. For instance, a methylation patterns could be expressed as '---M----U-------U-----M------' where the 'M' represents a methylated CpG site, the 'U' represents an unmethylated CpG site, the dashed lines represent different nucleotide distances between any two CpG sites or surrounding a CpG site. A long DNA molecule carrying more CpG sites increases the complexity of 'molecular barcode', enabling a higher specificity of tissue-of-origin analysis for a DNA molecule derived from LEPs in a pregnant woman, in comparison with a short DNA molecule.

For example, one cannot determine which organ contributes a DNA molecule containing 1 CpG site in a DNA mixture in pregnant subjects, e.g., where the mixture includes DNA from the placenta, the liver, the intestines, the lungs, the heart, the brain, T cells, B cells, neutrophiles, megakaryocytes, and erythroblasts based on its methylation status, as many tissues share the same methylation status. In contrast, one can have a higher likelihood (specificity) of accurately determining which organ contributes a DNA molecule containing sufficient CpG sites (e.g., >30 CpG sites) based on single-molecule methylation patterns across a series of CpG sites. The determination of the tissue of origin for LEP DNA molecules in pregnant women could be implemented by comparing the methylation patterns of LEP DNA greater than a certain size (e.g., >1000 bp) with the reference methylation patterns of various tissues including but not limited to the placenta, the liver, the intestines, the lungs, the heart, the brain, T cells, B cells, neutrophiles, megakaryocytes, and erythroblasts.

Comparing LEV DNA methylation with reference methylation patterns can comprise but not limited to the edit distance calculation (e.g., the minimal edit distance pointing to the tissue contributing such a molecule being analyzed), bitwise operation, naive Bayes classifier, random forest tree, support vector machine, gradient boosting, hidden Markov model, artificial intelligence-based algorithms such as convolutional neural network, and deep recurrent neural network.

Figure 18:
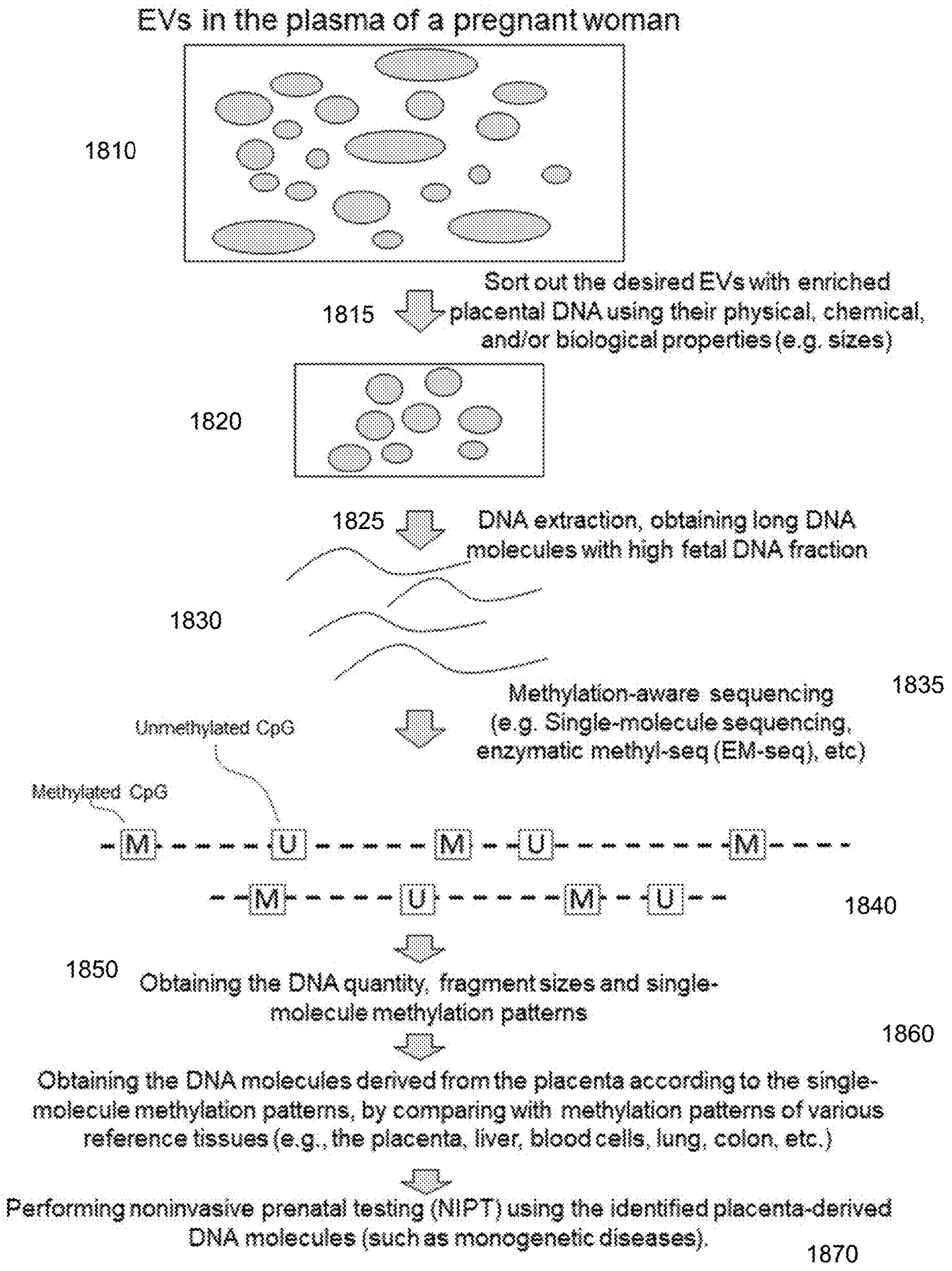
FIG. 18 shows an example of using EV DNA molecules for noninvasive prenatal testing.

FIG. 18 shows an example of using EV DNA molecules for noninvasive prenatal testing. The EV DNA molecules determined to be of placental origin based on the methylation patterns based on embodiments in this disclosure can be used for noninvasive prenatal testing (NIPT) for pregnant women. Examples of such NIPT can include the detection of fetal chromosomal aneuploidies, monogenetic disease detection, detection of fetal copy number aberrations, etc.

As depicted in FIG. 18, biological sample 1810 shows EVs in the plasma of a pregnant woman. Biological sample 1810 also includes particle-free DNA, which is not shown.

At step 1815, the desired EVs (e.g., small or large) are sorted out using physical, chemical, and/or biological properties (e.g., sizes), e.g., as described herein. Enriched sample 1820 shows EVs within a desired size range.

At step 1825, DNA is extracted from the EVs in enriched sample 1820, e.g., by disrupting a membrane of the EVs. The extracted DNA 1830 includes long DNA with a high fetal fraction, as shown herein.

After extraction, at step 1835, the DNA fragments can be analyzed. For example, methylation-aware sequencing, such as bisulfite treatment, single-molecule sequencing, enzymatic methyl-seq (EM-seq), etc. The sequence reads 1840 show methylated CpG sites (M) and unmethylated CpG sites (U).

At step 1850, the sequence reads are analyzed to obtain one or more properties, such as DNA quantity (potentially at certain locations or regions as may be determined by aligning to a reference genome), fragment sizes (e.g., by determining a length of a long read of a whole DNA molecule or aligning paired-end reads), fragmentation patterns (such as an end motif or ending position in a reference genome), and methylation patterns.

At step 1860, DNA fragments (particularly long DNA fragments, e.g., at least 600 bp or other lengths mentioned herein) are identified as corresponding to particular reference tissues. Different tissues have different methylation patterns. Such reference methylation patterns can be determined by analyzing cells of a particular reference tissue. A reference methylation pattern can be designated as methylated when the methylation level at a site is greater than a specified threshold (e.g., 70%, 75%, 80%, 85%, 90%, 95%, or 99%). A reference methylation pattern can be designated as unmethylated when the methylation level at a site is less than a specified threshold (e.g., 30%, 25%, 20%, 15%, 10%, 5%, or 1%). Certain locations in a genome can have a pattern than is unique to a particular tissue. Optionally, the reference methylation patterns of various tissues can be obtained from single-molecule sequencing, expressing as methylation patterns across individual molecules, wherein the methylation status can be a binary value (0 or 1, respectively represents unmethylated and methylated status).

When the long DNA fragments have multiple CpG sites (e.g., as shown in FIG. 18), the pattern at the aligned location in the reference genome can be compared to reference patterns of one or more reference tissues at the aligned location. Whether the methylation pattern (U and M at particular positions) is the same at each of the positions can be used to determine the closest matching reference tissue, or potentially only provide a match when the methylation pattern is exactly the same. Such an identification can be accurate due to the long DNA fragments covering a multiple CpG sites, e.g., greater than 4, 5, 6, 7, 8, 9, or 10 CpG sites. In some implementations, only reference fetal (placental) tissue needs to be used to identify fetal DNA fragments.

After fetal DNA fragments are identified using methylation patterns, the fetal DNA can be analyzed to perform NIPT. Since such identified DNA fragments have a high likelihood of being fetal DNA fragments, the fetal fraction will be very high (e.g., +90%). Thus, the sequences of such identified fetal fragments can be used to identify the presence of one or more sequences (e.g., alleles and/or mutations) that indicate disease, such as a monogenetic disease or involving more than one disease. Portions or the entire genome of the fetus could be determined, e.g., using assembly techniques with the identified fetal DNA.

Accordingly, the sequencing technique for methods described herein can include methylation-aware sequencing. Then, for each of a plurality of sequence reads, a methylation pattern at CpG sites of the sequence read can be determined. The sequence read can also be aligned to a genomic location within a reference genome. The methylation pattern can be compared to a reference methylation pattern of fetal tissue at the genomic location. In this manner, the sequence read can be identified as corresponding to a fetal DNA molecule based on the comparing.

Once the fetal DNA fragments are identified, the fetal DNA can be analyzed. For example, it can be determined whether the fetus has a genomic abnormality (e.g., copy number, mutations, epigenetic disorders, etc.) using the sequence reads identified as corresponding to fetal DNA molecules based on the methylation patterns. Such a determination can use various properties of fetal DNA fragments across a genome or for particular regions, e.g., counts, size, and fragmentation.

3. Combined Sequence and Methylation Analysis

The methylation patterns can be used to determine the tissue of origin (placental origin) of a LEP-associated DNA molecule. It can be determined whether a single nucleotide variation (SNV) linked to the said methylation patterns is inherited by the fetus. It can also be determined whether a de novo mutation present in the maternal plasma DNA would be derived from the fetus according to its linked methylation pattern. As a corollary, the inheritance can be determined based on SNVs, which can be used to determine whether the observed abnormal methylation patterns is inherited by the fetus. Accordingly, the genetic and epigenetic inheritance analyses of the fetus can be synergistic to each other.

Genotype(s) and/or haplotype(s) of the fetus can be determined by analyzing the fetal DNA. For example, one or more haplotypes of the fetus can be determined using the sequence reads identified as corresponding to fetal DNA molecules based on fetal methylation patterns. Determining the one or more haplotypes of the fetus can include determining a first maternal haplotype as being inherited by the fetus. Determining the one or more haplotypes of the fetus can include determining a first paternal haplotype as being inherited by the fetus.

Besides identifying fetal DNA using a fetal-specific methylation pattern, a fetal-specific allele can also be used. Accordingly, methods can identify a sequence read as having a fetal-specific allele, and a methylation pattern at CpG sites of the sequence read can be determined. It can then be determined whether the fetus has an epigenetic abnormality using the methylation pattern. For example, the methylation pattern of the identified fetal DNA molecule can have a pattern that matches a pattern that is known to correspond to an epigenetic abnormality. Such an epigenetic abnormality can include fragile X syndrome.

4. Increase in Length while Maintaining Fetal Fraction

Approaches disclosed herein allow the selective analysis of long DNA molecules from LEP without the reduction of fetal DNA fraction. As mentioned above, the higher concentration of DNA molecules originating the placenta can lead to higher accuracy (e.g., sensitivity and/or specificity). In contrast, for particle-free cfDNA, which is much more fragmented compared with LEP DNA molecules, the selective analysis of long DNA molecule is often at great expense of the reduction of fetal DNA fraction. Hence, the use of LEP DNA molecules according to the embodiments of this disclosure could lead to a higher performance of NIPT.

VI. Methods

Various methods are described above and described in this section. Purification and/or treatment of a blood sample for extracellular vesicles (e.g., LEPs and SEPs) can be performed, resulting in an increase of fetal fraction and/or of long DNA fragments. Nucleic acid fragments (DNA and/or RNA) of a certain length can be selected, e.g., greater than a size threshold, which can result in an increase in the fetal fraction. The analysis can involve different types of assays, including sequencing and probe-based techniques, such as digital PCR. When performing sequencing, long nucleic acid fragments can be analyzed by using long read techniques or by fragmenting the nucleic acid fragments further and then using short read techniques.

A. Enrichment for NIPT Analysis Using Wash and/or DNase Treatment

A blood sample can be purified for EPs, e.g., using a physical separation technique such as centrifuging and/or filtration. Then the sample can be treated, e.g., by an ionic wash and/or nuclease treatments. In this manner, the sample can be enriched for vesicles (particles), and thus enriched for fetal nucleic acids.

Figure 19:
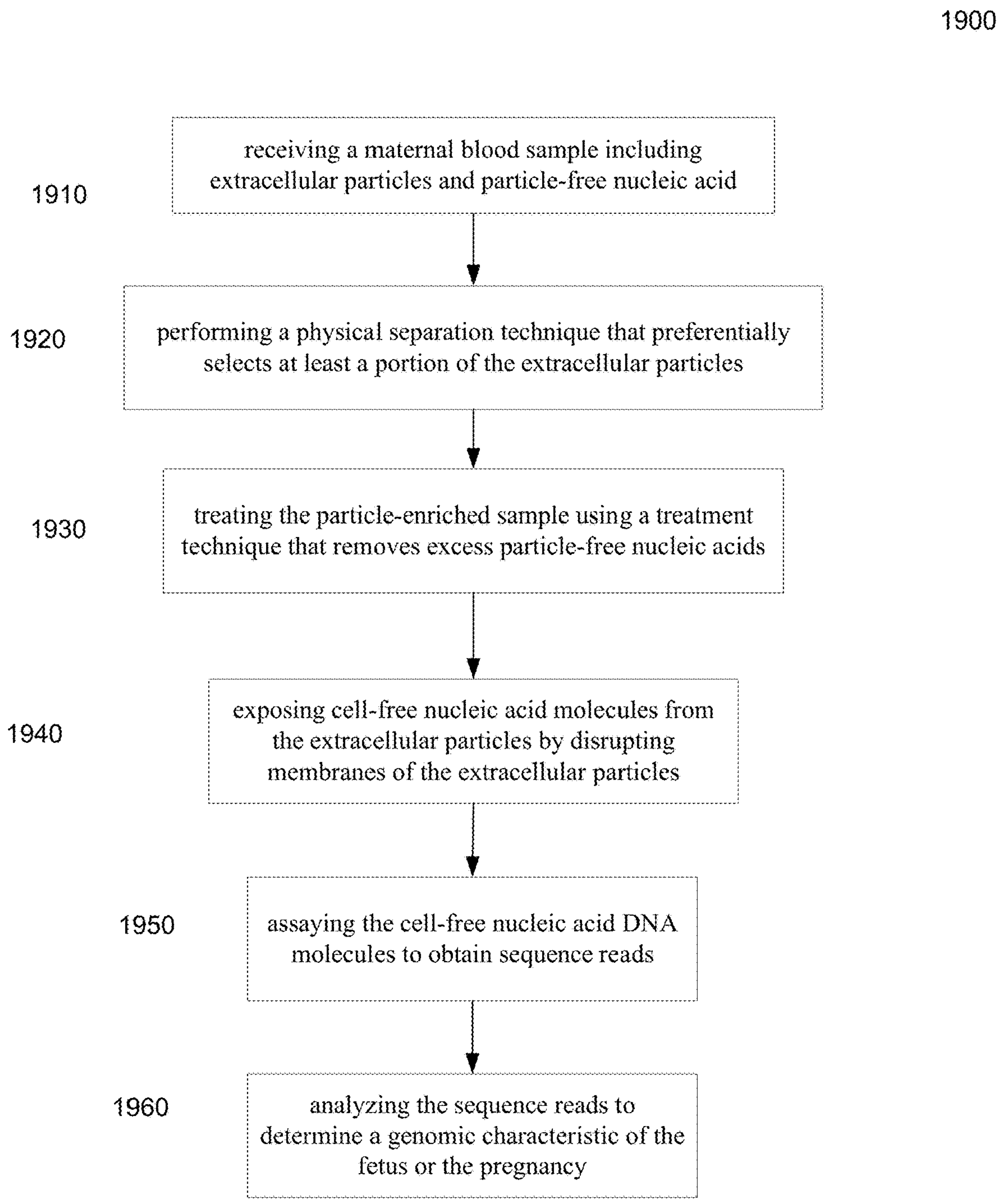
FIG. 19 is a flowchart illustrating a method of purifying and treating a blood sample of a female pregnant with a fetus.

FIG. 19 is a flowchart illustrating a method 1900 of purifying and treating a blood sample of a female pregnant with a fetus. The female may be pregnant with more than one fetus, which also applies to other techniques described herein. Method 1900 and other methods described herein can be performed partially using a computer system or entirely involving a computer system, e.g., that controls physical processes.

At block 1910, a blood sample of a female pregnant with a fetus is received. The blood sample includes extracellular particles and particle-free nucleic acids. The blood sample can be a plasma sample or can include other components, e.g., blood cells. The extracellular particles include cell-free nucleic acids inside of membranes. For example, each extracellular particle can include cell-free nucleic acids inside of a respective membrane. The blood sample may be received by a measurement system, which can perform physical steps as well as in silico steps.

At block 1920, a physical separation technique preferentially selects at least a portion of the extracellular particles, thereby obtaining a particle-enriched sample. For example, the physical separation technique can preferentially select particles below an upper threshold and/or above a lower threshold. Examples of such thresholds are provided in section II.A.1. For instance, an upper threshold can be 10 microns, 9 microns, 8 microns, 7 microns, 6 microns, 5 microns, or 4 microns, 3 microns, 2 microns. The lower threshold can be 200 nm, 300 nm, 400 nm, 500 nm, 600 nm, 700 nm, 800 nm, 900 nm, or 100 nm. As used herein, the term "preferentially" refers to a technique increasing a percentage of extracellular particles having a desired property (e.g., a specified size), thereby obtaining an enriched sample that has a higher percentage of extracellular particles with the desired property than the original sample.

Examples of the physical separation are provided herein, e.g., in section II.A and in FIGS. 1 and 2. For example, one or more stages of centrifugation can be performed. A pellet after the centrifugation can be extracted and later subjected to a treatment. The centrifuging parameters (e.g., force and time) can be selected to obtain particles of a desirable size, e.g., large or small. Examples of a force and time, as well as a number of centrifuging stages, are provided herein in other sections. Another example of physical separation is filtration, which is described in other sections.

One or more initial stages of centrifuging can be used to remove cells, e.g., by centrifuging at 500 g or more for at least 10 min. One or more subsequent centrifuging stages can be 10,000 g or more for at least 10 min, resulting in a pellet of LEPs, which can be removed. Thus, the one or more subsequent centrifuging stages can be used to remove LEPs. Further centrifuging can preferentially select for SEPs from the supernatant.

At block 1930, the particle-enriched sample is treated using a treatment technique that removes excess particle-free nucleic acids, thereby obtaining a treated particle-enriched sample. As examples, the treatment technique can include an ionic washing of the particle-enriched sample with an ionic solution (e.g., with phosphate buffered saline (PBS) or other saline solution) and/or applying a nuclease to the particle-enriched sample. Either one of these two treatments can be performed multiple times and may alternate, e.g., a washing can be performed first, then nuclease treatment, following by another wash. Centrifuging steps can also be performed in between any treatment steps.

The treatment technique can increase a fractional concentration of fetal nucleic acids in the treated particle-enriched sample relative to the particle-enriched sample. Such an increase is shown in various figures, such as FIGS. 4, 5A-5B, and 6A-6B. Examples of such washing and nuclease treatments are described herein. A washing can remove nucleic acids that are floating in the sample, and the nuclease treatments can remove nucleic acids that are bound to the membrane of a vesicle (particle).

At block 1940, cell-free nucleic acid molecules from the extracellular particles are exposed by disrupting (e.g., lysing) membranes of the extracellular particles. Such disrupting can be performed in various ways, e.g., by mechanical disruption, acoustic wave, enzymatic hydrolysis (e.g., proteinase K), detergents (e.g., ionic surfactants such as sodium dodecyl sulfate (SDS) or nonionic surfactants such as TritonX-100), osmatic shock method, and frozen-thaw method. As a result of the disrupting, the membrane can be broken, thereby releasing the nucleic acid molecules (fragments) inside. These cell-free nucleic acid molecules (fragments) can be DNA and/or RNA.

At block 1950, the cell-free nucleic acid molecules are assayed to obtain sequence reads. Different types of assays can be used, including sequencing and probe-based techniques, such as digital PCR. Various forms of sequencing can be performed, such as long read techniques or by fragmenting the nucleic acid fragments further and then using short read techniques, as described herein. Cell-free nucleic acid molecules from inside an EP and/or bound to a surface of the EP may be assayed.

At block 1960, the sequence reads are analyzed to determine a genomic characteristic of the fetus or of the pregnancy. Examples of such characteristics are described herein. For example, such sequence reads can be analyzed for a variety of properties at certain positions, sites, or regions, such as counts, size of nucleic acid fragments, methylation level(s), ending positions in a genome, amount of overhand (jaggedness) at ends of a fragment, and motifs at the end of fragments, e.g., 3-mers or 4-mers at the end of the nucleic acid fragments. Further details of such techniques are described in U.S. Publication Nos. 2011/0105353, 2014/0019064, 2013/0237431, 2014/0195164, 2014/0315200, 2016/0017419, 2016/0217251, 2017/0073774, 2017/0024513, 2018/0105807, 2018/0142300, 2019/0341127, 2020/0056245, and 2020/0199656.

Examples of such analysis for pregnancy can include techniques from U.S. Publication Nos. 2014/0243212 (RNA signatures specific to preeclampsia) and 2018/0372726 (e.g., using referentially expressed region of one or more expressed markers). The genomic characteristic of the pregnancy can relate to one or more complications that reduce the female carrying the fetus to full term.

In one example, analyzing the sequence reads can be used to determine a genotype. Determining a genotype of the fetus at a locus can include aligning the sequence reads to a reference genome; and determining the locus includes a first allele when at least a specified percentage (e.g., 10%, 15%, 20%, etc.) of the sequence reads include the first allele at the locus. The genotype can indicate a mutation. Other examples include determining an inherited haplotype, determining tissue of origin of nucleic acid molecules, and determining a fetal DNA percentage.

B. Enrichment of Fetal Fraction by Size Selection of Nucleic Acid Fragments

A blood sample can be purified for EPs, e.g., using centrifuging and/or filtration. After assaying the particle cell-free nucleic acid molecules (e.g., DNA and/or RNA), a size of the cell-free nucleic acid molecules can be determined, and only certain nucleic acid fragments (molecules) can be selected. In this manner, the sample can be enriched for fetal nucleic acids.

Figure 20:
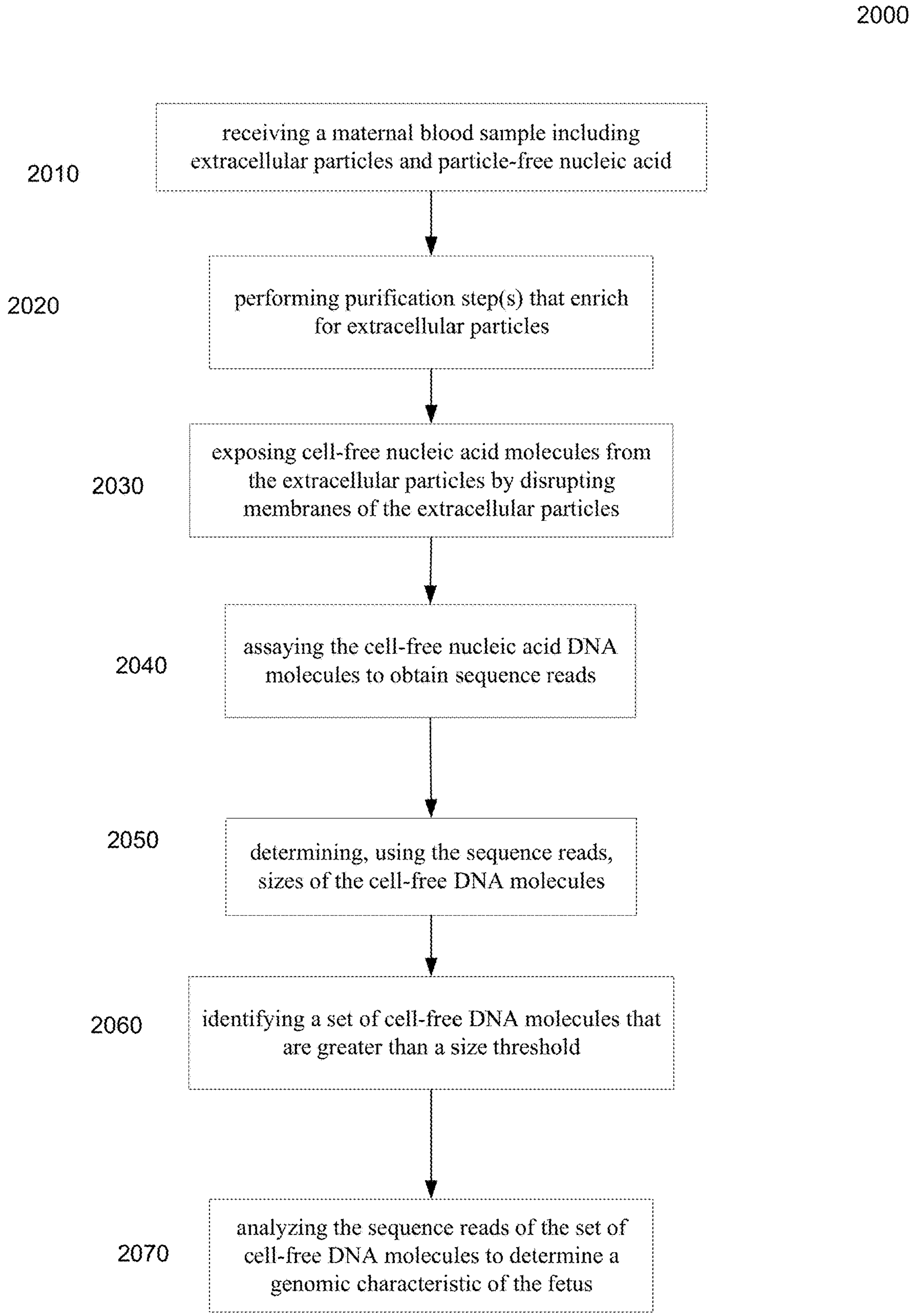
FIG. 20 is a flowchart illustrating a method of analyzing a blood sample of a female pregnant with a fetus, including selecting DNA fragments based on size.

FIG. 20 is a flowchart illustrating a method 2000 of analyzing a blood sample of a female pregnant with a fetus, including selecting nucleic acid molecules based on size.

At block 2010, a blood sample of a female pregnant with a fetus is received. The blood sample includes extracellular particles and particle-free nucleic acids. As with other methods, the blood sample can be a plasma sample or can include other components, e.g., blood cells. The extracellular particles include cell-free nucleic acids inside of membranes, as may occur with other methods described herein. The blood sample may be received by a measurement system, which can perform physical steps as well as in silico steps.

At block 2020, one or more purification steps that enrich for extracellular particles are performed, thereby producing an enriched sample. The one or more purification steps can include one or more physical separation techniques and/or treatment techniques. A physical separation technique can preferentially select at least a portion of the extracellular particles, thereby obtaining a particle-enriched sample. A physical separation technique can be performed in a similar manner as block 1920 of method 1900. A treatment technique can be performed in a similar manner as block 1930 of method 1900.

As an example, the one or more purification steps can include filtration using one or more filters or flow cytometry. As another example, the one or more purification steps can include centrifuging. The one or more purifications steps can preferentially select the extracellular particles above a specified size.

As other examples, the one or more purification steps can include performing a physical separation technique that preferentially selects at least a portion of the extracellular particles, thereby obtaining a particle-enriched sample; and treating the particle-enriched sample using a treatment technique that removes excess particle-free nucleic acid molecules, thereby obtaining a treated particle-enriched sample. As an example, the physical separation technique can include at least one stage of centrifuging, e.g., centrifuging at 16,000 g or more for at least 10 minutes. The treatment technique can include washing the particle-enriched sample with an ionic solution and/or applying a nuclease to the particle-enriched sample. The first treatment technique can increase a fractional concentration of fetal DNA in the treated particle-enriched sample relative to the particle-enriched sample.

At block 2030, cell-free nucleic acid molecules from the extracellular particles are exposed by disrupting membranes of the extracellular particles. Block 2030 can be performed in a similar manner as block 1940 of method 1900.

At block 2040, the cell-free nucleic acid molecules are assayed to obtain sequence reads. As examples, the assaying can include sequencing or digital PCR. Block 2040 can be performed in a similar manner as block 1950 of method 1900. Cell-free nucleic acid molecules from inside an EP and/or bound to a surface of the EP may be assayed.

At block 2050, sizes of the cell-free nucleic acid molecules are determined. The sizes may be determined in various ways, e.g., using the sequence reads or a physical technique, such as an electrophoresis technique or differential amplification. A size can correspond to a length, mass, or weight of a nucleic acid molecule. A size may be a size range. The size may be determined in various ways. For example, the length of an entire sequence (as may be determined using long read sequencing, such as single molecule sequencing) can be used as the size. Thus, the assaying can include sequencing an entirety of each of the cell-free nucleic acid molecules, thereby generating one sequence read for each of the cell-free nucleic acid molecules, and determining the sizes of the cell-free nucleic acid molecules can include counting the nucleotides in the sequence reads of the cell-free nucleic acid molecules.

As another example, the size can be determined by aligning the end sequences of a fragment, as may be done using paired-end reads, so that the entire fragment does not need to be sequenced. Thus, determining the sizes of the cell-free nucleic acid molecules can include: for each of the cell-free nucleic acid molecules, aligning one or more sequence reads to a reference genome.

In some implementations, sizes of nucleic acid molecules can be determined using a physical technique, such as electrophoresis. In such an implementation, the physical size measurement can be performed before the assaying of the nucleic acid molecules. Thus, the sequence reads might not be used to determine the size in such an implementation.

In yet another example, determining the sizes of the cell-free nucleic acid molecules can include performing digital PCR with different amplicon sizes. For example, different primers can amplify molecules of different lengths resulting in amplicons of different length across the digital reactions. And different probes can detect the existence of amplicons of various sizes.

At block 2060, a set of cell-free nucleic acid molecules that are greater than a size threshold is identified. The size threshold can be 200 bp or more. As described herein, other example size thresholds are 200 bp, 300 bp, 400 bp, 500 bp, 600 bp, 700 bp, 800 bp, 900 bp, 1 kb, 2 kb, 3 kb, 4 kb, 5 kb, 10 kb, 20 kb, 30 kb, 40 kb, 50 kb, 100 kb, 500 kb, and 1 Mb.

When the sizes are determined using a physical separation technique, the set of cell-free nucleic acid molecules can be identified before the assaying is performed. For example, the cell-free nucleic acid molecules within a certain range of sizes can be captured, and then those nucleic acids can assayed. When the sizes are determined using the sequence reads, the cell-free nucleic acids that are of the desired range can be identified, and their sequence information can be used.

At block 2070, sequence reads of the set of cell-free nucleic acid molecules are analyzed to determine a genomic characteristic of the fetus. Block 2070 can be performed in a similar manner as block 1960 of method 1900.

C. Sequencing for Long Reads

A blood sample can be purified for EPs, e.g., using centrifuging and/or filtration. In order to capture the long nucleic acid fragments that are surprisingly in the EPs, long read sequencing techniques can be performed. In this manner, the sample can be enriched for fetal nucleic acids, and the long cell-free fetal nucleic acid molecules (e.g., DNA and/or RNA) can be sequenced. Since cell-free nucleic acid molecules in plasma are known to be short (as they are naturally fragmented), it would be unconventional to perform long read sequencing of cell-free nucleic acid molecules.

Figure 21:
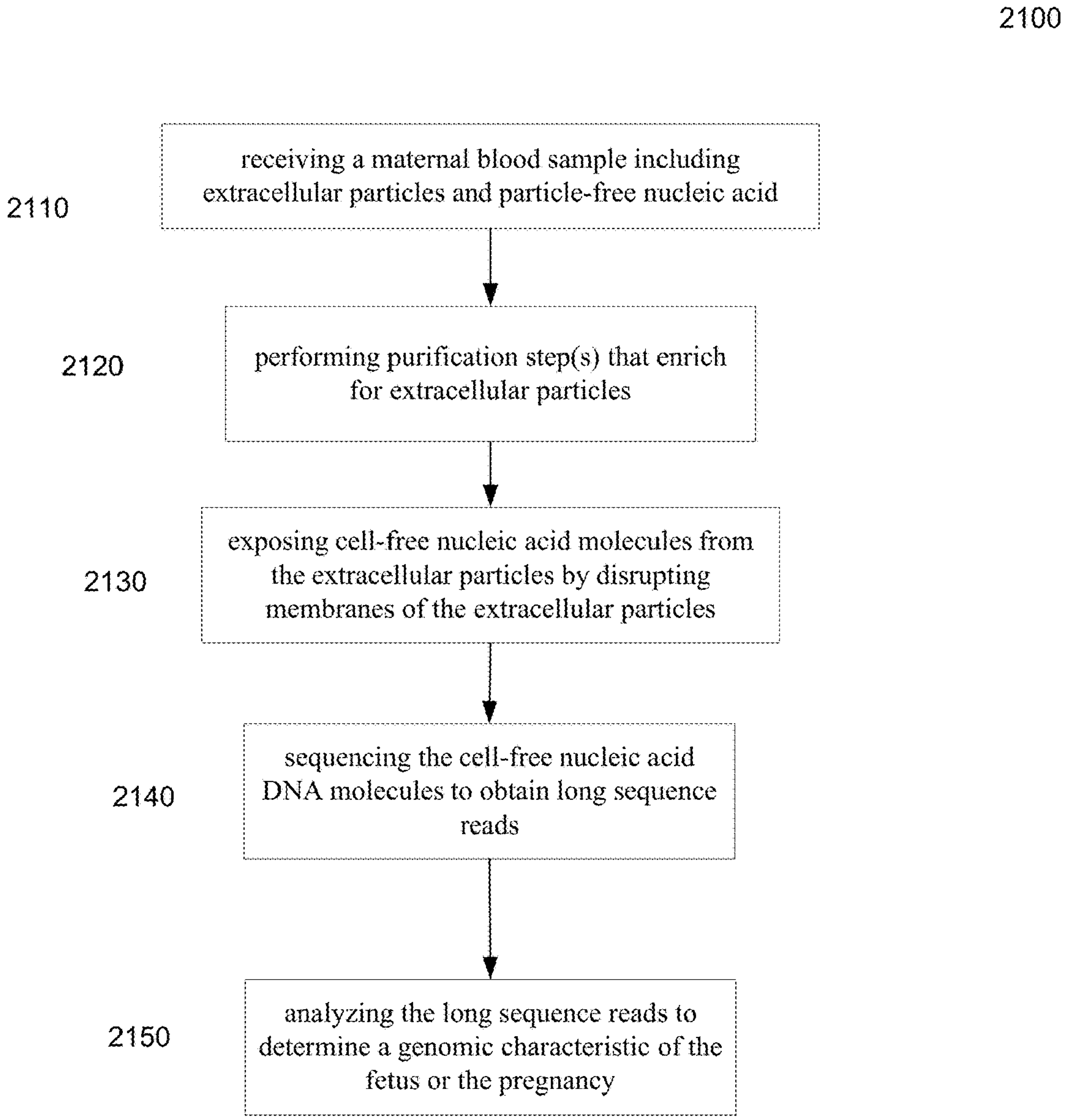
FIG. 21 is a flowchart illustrating a method of analyzing a blood sample of a female pregnant with a fetus, including performing long read sequencing.

FIG. 21 is a flowchart illustrating a method 2100 of analyzing a blood sample of a female pregnant with a fetus, including performing long read sequencing.

At block 2110, a blood sample of a female pregnant with a fetus is received. The blood sample includes extracellular particles and particle-free nucleic acid molecules. The extracellular particles include cell-free nucleic acid molecules inside of membranes.

At block 2120, one or more purification steps that enrich for the extracellular particles are performed, thereby producing an enriched sample. Block 2120 can be performed in a similar manner as block 1920 of method 1900.

At block 2130, cell-free nucleic acid molecules from the extracellular particles are exposed by disrupting membranes of the extracellular particles. Block 2130 can be performed in a similar manner as block 1930 of method 1900.

At block 2140, the cell-free nucleic acid molecules are sequenced, using a sequencing technique, to obtain sequence reads. The sequencing technique is such that at least a portion of the sequence reads are more than a size threshold, e.g., 600 bp. Other such size thresholds can be 700 bp, 800 bp, 900 bp, or 1000 bp, or other size thresholds described herein. As an example, the sequencing technique can include single molecule sequencing, such as nanopore sequencing (e.g., Oxford Nanopore Technologies) and single-molecule real-time sequencing (e.g., Pacific Biosciences). The sequencing technique can sequence short and long reads. Cell-free nucleic acid molecules from inside an EP and/or bound to a surface of the EP may be sequenced.

Other examples of long read sequencing techniques include synthetic long-read sequencing (Illumina) and linked-read technology (10× genomics, Tell-seq). In such implementations, long nucleic acid molecules are fragmented in a partition and its subsequences are tagged with the same barcode sequence (i.e. molecular barcode). Different long nucleic acid molecule are allocated in different partitions and are tagged with different molecular barcodes. Thus, the fragments derived from the long nucleic acid molecules can be assembled back to the original long nucleic acid molecules based on the same molecular barcodes. As examples, the partitions can be implemented using droplets, beads, serial dilutions, or wells.

At block 2150, the sequence reads are analyzed to determine a genomic characteristic of the fetus. All of the nucleic acid fragments can be sequenced, and thus the analyzed sequence reads can be of various lengths, including the sequence reads from the long DNA fragments. A sequence read can be of the entire nucleic acid fragment or of just the ends. Block 2150 can be performed in a similar manner as block 1970 of method 1900.

As an example, analyzing the sequence reads can include determining a haplotype of the fetus by aligning sequence reads longer than 600 bp to each other, e.g., as part of de novo assembly. At least a portion of the aligned sequence reads can include a plurality of heterozygous locus. The aligned sequence reads can share a heterozygous locus with a same allele, thereby allowing alignment, with difference sequence reads overlapping different amounts and at different loci.

D. Performing Fragmentation for Short Read Platforms

A blood sample can be purified for EPs, e.g., using centrifuging and/or filtration. In order to capture the long nucleic acid fragments that are surprisingly in the EPs, the cell-free nucleic acid fragments (e.g., DNA and/or RNA) extracted from the EPs can be further fragmented and sequenced using a short-read sequencing platform. In this manner, the sample can be enriched for fetal nucleic acids, and the long cell-free fetal nucleic acid molecules can be sequenced. Since cell-free nucleic acid molecules in plasma are known to be short (as they are naturally fragmented), it would be unconventional to perform a fragmentation step.

Figure 22:
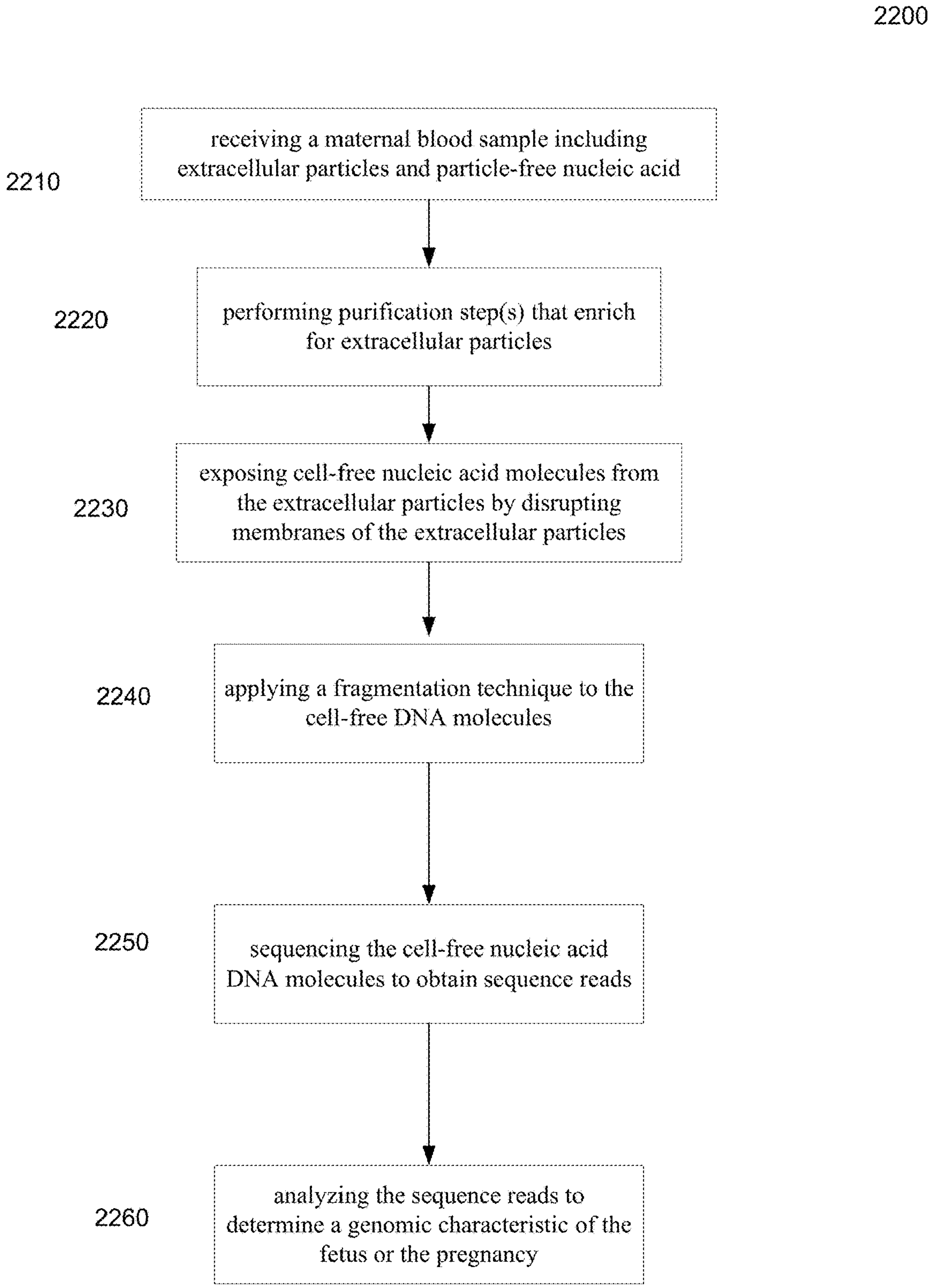
FIG. 22 is a flowchart illustrating a method of analyzing a blood sample of a female pregnant with a fetus, including performing fragmentation and short read sequencing.

FIG. 22 is a flowchart illustrating a method 2200 of analyzing a blood sample of a female pregnant with a fetus, including performing fragmentation and short read sequencing.

At block 2210, a blood sample of a female pregnant with a fetus is received. The blood sample includes extracellular particles and particle-free nucleic acid molecules. The extracellular particles include cell-free nucleic acid molecules inside of a membrane.

At block 2220, one or more purification steps that enrich for the extracellular particles are performed, thereby producing an enriched sample. Block 2220 can be performed in a similar manner as block 1920 of method 1900.

At block 2230, cell-free nucleic acid molecules from the extracellular particles are exposed by disrupting membranes of the extracellular particles. At least a portion of the cell-free nucleic acid molecules from the extracellular particles are at least 600 bp. Block 2230 can be performed in a similar manner as block 1930 of method 1900.

At block 2240, a fragmentation technique is applied to the cell-free nucleic acid molecules. The fragmentation can reduce the length of long nucleic acid fragments so that they can be sequenced using a short-read sequencing platform, such as Illumina. Mechanical shearing, enzymatic fragmentation such as Tn5 transposase based tagmentation; DNASE1, DNASE1L3, and/or DFFB treatments; light; sonication; or chemical DNA fragmentation using a combination of divalent metal cations such as magnesium or zinc and heat to break nucleic acids. In some embodiment, bisulfate treatment could be used for fragmenting nucleic acid molecules.

At block 2250, after applying the fragmentation technique, the cell-free nucleic acid molecules are sequenced to obtain sequence reads. Since at least some of the long nucleic acid molecules are fragmented, the resulting fragments can be sequenced with a short-read sequencing platform. Cell-free nucleic acid molecules from inside an EP and/or bound to a surface of the EP may be sequenced.

At block 2260, the sequence reads are analyzed to determine a genomic characteristic of the fetus or pregnancy of the female. Block 2260 can be performed in a similar manner as block 1970 of method 1900.

For any of the methods described herein, the analysis can determine an inherited haplotype, e.g., from the mother. As an example, analyzing the sequence reads can include determining, using the sequence reads, a difference in allelic counts at heterozygous loci of two maternal haplotypes; and determining an inherited haplotype for each of a plurality of regions using the difference in the allelic counts. As shown in FIG. 17B, an average haplotype block size can be below 2 Mb or 1.5 Mb.

VII. Example Systems

Figure 23:
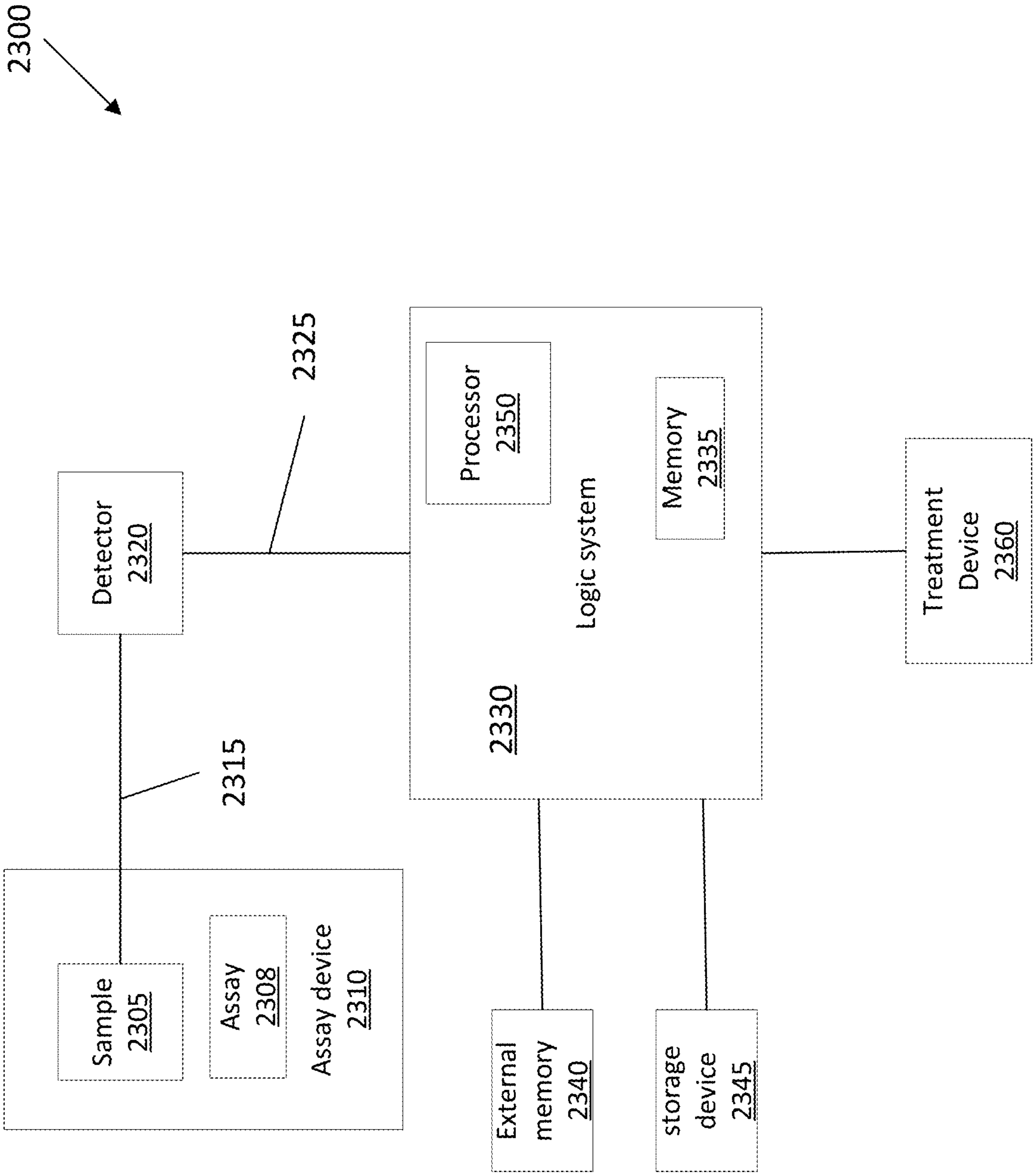
FIG. 23 illustrates a measurement system according to an embodiment of the present invention.

FIG. 23 illustrates a measurement system 2300 according to an embodiment of the present disclosure. The system as shown includes a sample 2305, such as cell-free nucleic acid molecules (e.g., DNA and/or RNA) within an assay device 2310, where an assay 2308 can be performed on sample 2305. For example, sample 2305 can be contacted with reagents of assay 2308 to provide a signal of a physical characteristic 2315 (e.g., sequence information of a cell-free nucleic acid molecule). An example of an assay device can be a flow cell that includes probes and/or primers of an assay or a tube through which a droplet moves (with the droplet including the assay). Physical characteristic 2315 (e.g., a fluorescence intensity, a voltage, or a current), from the sample is detected by detector 2320. Detector 2320 can take a measurement at intervals (e.g., periodic intervals) to obtain data points that make up a data signal. In one embodiment, an analog-to-digital converter converts an analog signal from the detector into digital form at a plurality of times. Assay device 2310 and detector 2320 can form an assay system, e.g., a sequencing system that performs sequencing according to embodiments described herein. A data signal 2325 is sent from detector 2320 to logic system 2330. As an example, data signal 2325 can be used to determine sequences and/or locations in a reference genome of nucleic acid molecules (e.g., DNA and/or RNA). Data signal 2325 can include various measurements made at a same time, e.g., different colors of fluorescent dyes or different electrical signals for different molecule of sample 2305, and thus data signal 2325 can correspond to multiple signals. Data signal 2325 may be stored in a local memory 2335, an external memory 2340, or a storage device 2345.

Logic system 2330 may be, or may include, a computer system, ASIC, microprocessor, graphics processing unit (GPU), etc. It may also include or be coupled with a display (e.g., monitor, LED display, etc.) and a user input device (e.g., mouse, keyboard, buttons, etc.). Logic system 2330 and the other components may be part of a stand-alone or network connected computer system, or they may be directly attached to or incorporated in a device (e.g., a sequencing device) that includes detector 2320 and/or assay device 2310. Logic system 2330 may also include software that executes in a processor 2350. Logic system 2330 may include a computer readable medium storing instructions for controlling measurement system 2300 to perform any of the methods described herein. For example, logic system 2330 can provide commands to a system that includes assay device 2310 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Measurement system 2300 may also include a treatment device 2360, which can provide a treatment to the subject. Treatment device 2360 can determine a treatment and/or be used to perform a treatment. Examples of such treatment can include surgery, radiation therapy, chemotherapy, immunotherapy, targeted therapy, hormone therapy, and stem cell transplant. Logic system 2330 may be connected to treatment device 2360, e.g., to provide results of a method described herein. The treatment device may receive inputs from other devices, such as an imaging device and user inputs (e.g., to control the treatment, such as controls over a robotic system).

Figure 24:
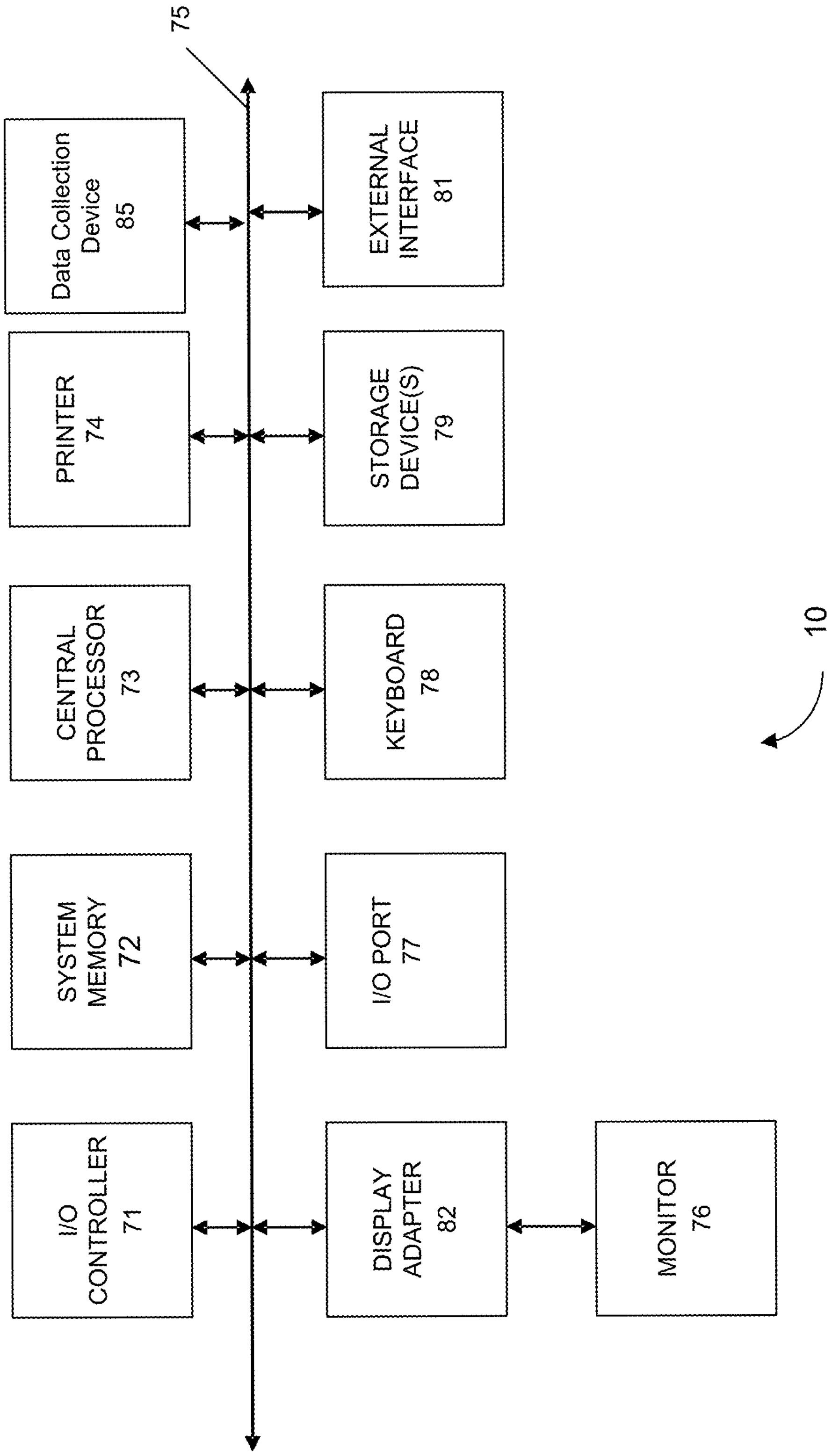
FIG. 24 illustrates example subsystems that implement a measurement system according to an embodiment of the present invention.

Any of the computer systems mentioned herein may utilize any suitable number of subsystems. Examples of such subsystems are shown in FIG. 24 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 24 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g., Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g., an application specific integrated circuit or field programmable gate array) and/or using computer software stored in a memory with a generally programmable processor in a modular or integrated manner, and thus a processor can include memory storing software instructions that configure hardware circuitry, as well as an FPGA with configuration instructions or an ASIC. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such devices. In addition, the order of operations may be re-arranged. A process can be terminated when its operations are completed but could have additional steps not included in a figure. A process may correspond to a method, a function, a procedure, a subroutine, a subprogram, etc. When a process corresponds to a function, its termination may correspond to a return of the function to the calling function or the main function.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device (e.g., as firmware) or provided separately from other devices (e.g., via Internet download). Any such computer readable medium may reside on or within a single computer product (e.g., a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Any operations performed with a processor (e.g., aligning, determining, comparing, computing, calculating) may be performed in real-time. The term "real-time" may refer to computing operations or processes that are completed within a certain time constraint. The time constraint may be 1 minute, 1 hour, 1 day, or 7 days. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

The claims may be drafted to exclude any element which may be optional. As such, this statement is intended to serve as antecedent basis for use of such exclusive terminology as "solely", "only", and the like in connection with the recitation of claim elements, or the use of a "negative" limitation.

All patents, patent applications, publications, and descriptions mentioned herein are incorporated by reference in their entirety for all purposes. None is admitted to be prior art. Where a conflict exists between the instant application and a reference provided herein, the instant application shall dominate.

What is claimed is:

1. A method comprising:

receiving a blood sample of a female having a pregnancy with a fetus;

performing one or more purification steps that enrich for extracellular particles, thereby producing an enriched sample, wherein the extracellular particles include cell-free nucleic acids inside of membranes;

exposing cell-free nucleic acid molecules from the extracellular particles by disrupting membranes of the extracellular particles;

assaying the cell-free nucleic acid molecules to obtain sequence reads;

determining sizes of the cell-free nucleic acid molecules;

identifying a set of cell-free nucleic acid molecules that are greater than a size threshold, the size threshold being 200 bp or more; and analyzing sequence reads of the set of cell-free nucleic acid molecules to determine a genomic characteristic of the fetus.

2. A method comprising:

receiving a blood sample of a female having a pregnancy with a fetus, the blood sample including extracellular particles and particle-free nucleic acids, wherein the extracellular particles include cell-free nucleic acids inside of membranes;

performing a physical separation technique that preferentially selects at least a portion of the extracellular particles, thereby obtaining a particle-enriched sample;

treating the particle-enriched sample using a treatment technique that removes excess particle-free nucleic acids, thereby obtaining a treated particle-enriched sample, the treatment technique including washing the particle-enriched sample with an ionic solution and applying a nuclease to the particle-enriched sample, wherein the treatment technique increases a fractional concentration of fetal nucleic acids in the treated particle-enriched sample relative to the particle-enriched sample;

exposing cell-free nucleic acid molecules from the extracellular particles by disrupting membranes of the extracellular particles;

assaying the cell-free nucleic acid molecules to obtain sequence reads; and analyzing the sequence reads to determine a genomic characteristic of the fetus or of the pregnancy of the female.

3. The method of claim 2, wherein the assaying includes sequencing using a sequencing technique or digital PCR.

4. The method of claim 2, wherein the ionic solution is phosphate buffered saline (PBS).

5. A method comprising:

receiving a blood sample of a female having a pregnancy with a fetus, the blood sample including extracellular particles and particle-free nucleic acids, wherein the extracellular particles include cell-free nucleic acids inside of membranes;

performing one or more purification steps that enrich for the extracellular particles, thereby producing an enriched sample;

exposing cell-free nucleic acid molecules from the extracellular particles by disrupting membranes of the extracellular particles;

sequencing, using a sequencing technique, the cell-free nucleic acid molecules to obtain sequence reads, wherein at least a portion of the sequence reads are more than 600 bp; and analyzing the sequence reads to determine a genomic characteristic of the fetus or of the pregnancy of the female.

6. The method of claim 2, wherein the genomic characteristic is of the pregnancy, and wherein the genomic characteristic of the pregnancy relates to one or more complications that reduce the female carrying the fetus to full term.

7. The method of claim 2, wherein the treatment technique includes washing the particle-enriched sample with the ionic solution and applying the nuclease to the particle-enriched sample.

8. The method of claim 2, wherein the treatment technique includes the washing with the ionic solution, and wherein the ionic solution is PBS.

9. The method of claim 8, wherein the treatment technique includes applying the nuclease to the particle-enriched sample.

10. The method of claim 2, wherein the nuclease is selected from the group consisting of: DNase I, TREX1 (Three Prime Repair Exonuclease 1), AEN (Apoptosis Enhancing Nuclease), EXO1 (Exonuclease 1), DNASE2 (Deoxyribonuclease 2), ENDOG (Endonuclease G), APEX1 (Apurinic/Apyrimidinic Endodeoxyribonuclease 1), FEN1 (Flap Structure-Specific Endonuclease 1), DNASEIL1 (Deoxyribonuclease 1 Like 1), DNASEIL2 (Deoxyribonuclease 1 Like 2) and EXOG (Exo/Endonuclease G).

11. The method of claim 2, wherein the physical separation technique preferentially selects particles below an upper threshold and above a lower threshold.

12. The method of claim 2, wherein the physical separation technique includes at least one stage of centrifuging.

13. The method of claim 12, wherein the centrifuging is at 16,000 g or more for at least 10 minutes.

14. The method of claim 2, wherein filtration using one or more filters or flow cytometry is used to enrich or select the extracellular particles of a specified size.

15. The method of claim 2, wherein the extracellular particles above a specified size are preferentially selected or enriched, wherein the specified size is at least 200 nm.

16. The method of claim 2, wherein analyzing the sequence reads includes:
- determining, using the sequence reads, a difference in allelic counts at heterozygous loci of two maternal haplotypes; and
- determining an inherited haplotype for each of a plurality of regions using the difference in the allelic counts, wherein an average haplotype block size is below 2 Mb.

17. The method of claim 2, wherein analyzing the sequence reads includes:
- determining a genotype of the fetus at a locus by:
  - aligning the sequence reads to a reference genome; and
  - determining the locus includes a first allele when at least 15% of the sequence reads include the first allele at the locus.

18. The method of claim 17, wherein the genomic characteristic is of the fetus, and wherein the genotype indicates a mutation.

19. The method of claim 2, wherein analyzing the sequence reads includes:
- determining a haplotype of the fetus by aligning sequence reads longer than 600 bp to each other, the haplotype being the genomic characteristic of the fetus, wherein aligned sequence reads share a heterozygous locus with a same allele, and wherein at least a portion of the aligned sequence reads includes a plurality of heterozygous locus.

20. The method of claim 2, wherein the genomic characteristic of the fetus is a sequence imbalance at a locus or a region of a fetal genome of the fetus.

21. The method of claim 2, wherein disrupting the membranes of the extracellular particles includes mechanical disruption, acoustic wave, enzymatic hydrolysis, detergents, osmatic shock, or frozen-thaw.

22. The method of claim 2, wherein the sequence reads are also obtained from cell-free nucleic acid molecules that are bound to the membranes of the extracellular particles.

23. The method of claim 3, wherein the sequencing technique includes single molecule sequencing.

24. The method of claim 23, wherein the sequencing technique uses a nanopore.

25. The method of claim 3, wherein the sequencing technique includes linked-read sequencing.

26. The method of claim 3, wherein the sequencing technique includes methylation-aware sequencing.

27. The method of claim 26, wherein the analyzing includes:
- for each of a plurality of sequence reads:
  - determining a methylation pattern at CpG sites of the sequence read, thereby determining methylation patterns;
  - aligning the sequence read to a genomic location within a reference genome; and
  - comparing the methylation pattern to a reference methylation pattern of fetal tissue at the genomic location; and
  - identifying the sequence read as corresponding to a fetal nucleic acid molecule based on the comparing.

28. The method of claim 27, wherein the analyzing further includes:
- determining whether the fetus has a genomic abnormality using the sequence reads identified as corresponding to fetal nucleic acid molecules based on the methylation patterns.

29. The method of claim 27, wherein the analyzing further includes:
- determining one or more haplotypes of the fetus using the sequence reads identified as corresponding to fetal nucleic acid molecules based on the methylation patterns.

30. The method of claim 29, wherein determining the one or more haplotypes of the fetus includes determining a first maternal haplotype as being inherited by the fetus.

31. The method of claim 29, wherein determining the one or more haplotypes of the fetus includes determining a first paternal haplotype as being inherited by the fetus.

32. The method of claim 26, further comprising:
- identifying a sequence read as having a fetal-specific allele;
- determining a methylation pattern at CpG sites of the sequence read; and
- determining whether the fetus has an epigenetic abnormality using the methylation pattern.

33. The method of claim 32, wherein the epigenetic abnormality is fragile X syndrome.

* * * * *